United States Patent
Raftery et al.

(10) Patent No.: US 9,739,780 B2
(45) Date of Patent: Aug. 22, 2017

(54) METABOLITE BIOMARKERS FOR THE DETECTION OF LIVER CANCER

(71) Applicant: Purdue Research Foundation, West Lafayette, IN (US)

(72) Inventors: Michael Daniel Raftery, Seattle, WA (US); Jeremiah Bowers, DePere, WI (US); Siwei Wei, Richland, WA (US); Hamid Reza Baniasadi, West Lafayette, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 237 days.

(21) Appl. No.: 14/401,135

(22) PCT Filed: May 21, 2013

(86) PCT No.: PCT/US2013/042109
§ 371 (c)(1),
(2) Date: Nov. 14, 2014

(87) PCT Pub. No.: WO2013/177222
PCT Pub. Date: Nov. 28, 2013

(65) Prior Publication Data
US 2015/0133331 A1    May 14, 2015

Related U.S. Application Data

(60) Provisional application No. 61/649,655, filed on May 21, 2012, provisional application No. 61/663,995, filed on Jun. 25, 2012, provisional application No. 61/711,371, filed on Oct. 9, 2012.

(51) Int. Cl.
*G01N 33/48* (2006.01)
*G01N 33/574* (2006.01)

(52) U.S. Cl.
CPC .......................... *G01N 33/57438* (2013.01)

(58) Field of Classification Search
None
See application file for complete search history.

(56) References Cited

PUBLICATIONS

Chen, T. et al. Serum and Urine Metabolite Profiling Reveals Potential Biomarkers of Human Hepatocellular Carcinoma, 2011, Molecular & Cellular Proteaomics, vol. 10(7), pp. 1-13.*

(Continued)

*Primary Examiner* — Robert Xu
(74) *Attorney, Agent, or Firm* — Purdue Research Foundation; Yonghao Hou

(57) ABSTRACT

Methods for the detection and screening of hepatocellular carcinoma (HCC) patients and for the monitoring of HCC treatment using a panel or panels of small molecule metabolite biomarkers are disclosed. In other aspects, methods for detection and screening for the progression of high-risk conditions, such as HCV infections, to HCC and to monitoring treatment using a panel or panels of small molecule metabolite biomarkers are disclosed. The biomarkers are sensitive and specific for the detection of HCC, and can also be used to classify HCV infections that are regarded as precursors of HCC.

9 Claims, 25 Drawing Sheets

(56) References Cited

PUBLICATIONS

Hidayat, S., et al., Inhibition of amino acid-mTOR signaling by a leucine derivative induces G1 arrest in Jurkat cells. Biochemical and Biophysical Research Communications 301 (2003) 417-423.

Chen, C., et al., Risk of Hepatocellular Carcinoma Across a Biological Gradient of Serum Hepatitis B Virus DNA LevelJAMA. 2006;295:65-73.

El-Serag, H. B., Hepatocellular Carcinoma, An Epidemiologic View. J Clin Gastroenterol 2002;35(Suppl. 2): S72-S78.

Hickman, I. J., et al., Effect of weight reduction on liver histology and biochemistry in patients with chronic hepatitis C. Gut 2002;51:89-94.

Gerlach, J. T., et al., Acute Hepatitis C: High Rate of Both Spontaneous and Treatment-Induced Viral Clearance. Gastroenterology 2003;125:80-88.

Amstrong, G. L., et al., The Prevalence of Hepatitis C Virus Infection in the United States, 1999 through 2002. Ann Intern Med. 2006;144:705-714.

Seeff, L. B., et al., Natural History of Chronic Hepatitis C. Hepatology 2002;36:S35-S46.

Alter, M. J., et al., Epidemiology of hepatitis C virus infection. World J Gastroenterol May 7, 2007; 13(17): 2436-2441.

Wilkins, T., et al., Hepatitis C: Diagnosis and Treatment. Am Fam Physician. 2010;81(11):1351-1357.

Strader, D. B., et al., Diagnosis, Management, and Treatment of Hepatitis C. Hepatology, 2004, 39(4), 1147-1171.

Maylin, S., et al., Eradication of Hepatitis C Virus in Patients Successfully Treated for Chronic Hepatitis C. Gastroenterology 2008;135:821-829.

Everson, G. T., et al., Quantitative Tests of Liver Function Measure Hepatic Improvement after Sustained Virologic Response: Results from the HALT-C Trial. Aliment Pharmacol Ther. Mar. 1, 2009; 29(5): 589-601.

Ward, R. P., et al., Management of Hepatitis C: Evaluating Suitability for Drug Therapy. Am Fam Physician 2004;69:E1429-E38,1439-40.

Craxi, A., Acute Hepatitis C: in Search of the Optimal Approach to Cure. Hepatology, 43(2), 221-224.

Sreekumar, A., et al., Metabolomic Profiles Delineate Potential Role for Sarcosine in Prostate Cancer Progression. Nature. Feb. 12, 2009; 457(7231): 910-914.

Tiziani, S. et al., Early Stage Diagnosis of Oral Cancer Using 1H NMR-Based Metabolomics. Neoplasia (2009) 11, 269-276.

Spratlin, J. L., et al., Clinical Applications of Metabolomics in Oncology: A Review. Clin Cancer Res. Jan. 15, 2009; 15(2): 431-440.

Thysell, E. et al., Metabolomic Characterization of Human Prostate Cancer Bone Metastases Reveals Increased Levels of Cholesterol. PLoS One 5(12): e14175.

Asiago, V. M., et al., Early Detection of Recurrent Breast Cancer Using Metabolite Profiling. Cancer Res. Nov. 1, 2010; 70(21): 8309-8318.

Wang, Z., et al., Gut flora metabolism of phosphatidylcholine promotes cardiovascular disease. Nature, 2011, 472, 57-64.

Nicholson, J. K., et al., 'Metabonomics': understanding the metabolic responses of living systems to pathophysiological stimuli via multivariate statistical analysis of biological NMR spectroscopic data. x e n o b i o t i c a, 1999, vol. 29, No. 11, 1181-1189.

Gowda, N. et al., Metabolomics-Based Methods for Early Disease Diagnostics: A Review. Expert Rev Mol Diagn. Sep. 2008 ; 8(5): 617-633.

Crews, B., et al., Variability analysis of human plasma and cerebral spinal fluid reveals statistical significance of changes in mass spectrometry-based metabolomics data. Anal Chem. Oct. 15, 2009; 81(20): 8538-8544.

Fiehn, O., Metabolomics—the link between genotypes and phenotypes. Plant Molecular Biology 48: 155-171, 2002.

Sabatini, D. M., mTOR and cancer: insights into a complex relationship. Nature Reviews | Cancer, vol. 6, 2006, 729-734.

Davis, V. W., et al., Metabolomics and Surgical Oncology: Potential Role for Small Molecule Biomarkers. Journal of Surgical Oncology 2011;103:451-459.

Tan, Y., et al., Metabolomics Study of Stepwise Hepatocarcinogenesis From the Model Rats to Patients: Potential Biomarkers Effective for Small Hepatocellular Carcinoma Diagnosis. Molecular & Cellular Proteomics 11: 10.1074/mcp.M111. 010694, 1-12, 2012.

Patterson, A. D., et al., Aberrant Lipid Metabolism in Hepatocellular Carcinoma Revealed by Plasma Metabolomics and Lipid Profiling. Cancer Res; 71(21); 6590-600.

Tserng, K. et al., Metabolic Origin of Urinary 3-Hydroxy Dicarboxylic Acids. Biochemistry, vol. 30, No. 9, 1991 2508-2514.

Hille, R. Molybdenum-containing hydroxylases. Archives of Biochemistry and Biophysics 433 (2005) 107-116.

Harrison, R., Structure and Function of Xanthine Oxidoreductase: Where Are We Now? Free Radical Biology & Medicine, 2002, vol. 33, No. 6, pp. 774-797.

Weber, G., Enzymes of Purine Metabolism in Cancer. Clin. Biochem. 1983, 16(1): 57-63.

Tanggo, Y., Clinical usefulness of serum cholylglycine determination in various liver diseases. Gastroentrol Jpn 1982, 17(5): 447-452.

Gilmore, T., Kinetics of 14C-glychocholic acid clearance in normal man and in patients with liver disease. Gut. 1978, 19(12): 1110-1115.

Niwa, T., 3-Hydroxyhexanoic acid: an abnormal metabolite in urine and serum of diabetic ketoacidotic patients. J. Chrom. B. Biom. Sci. App. 1985, 333: 1-7.

\* cited by examiner

METABOLITE BIOMARKERS FOR THE DETECTION OF LIVER CANCER

PRIORITY

This application claims the priority and benefit of, and is a U.S. §371 national stage entry of, International Patent Application Serial No. PCT/US2013/042109 filed May 21, 2013 which is related to and claims the benefit of and priority to U.S. Provisional Patent Application No. 61/649,655, filed May 21, 2012, U.S. Provisional Patent Application No. 61/663,995, filed Jun. 25, 2012, and U.S. Provisional Patent Application No. 61/711,371, filed Oct. 9, 2012, the contents of each of which is hereby incorporated by reference herein in its entirety.

STATEMENT REGARDING FEDERALLY SPONSORED RESEARCH OR DEVELOPMENT

This invention was made with government support under CA133770 awarded by the National Institutes of Health. The government has certain rights in the invention.

TECHNICAL FIELD

The present disclosure generally relates to small molecule biomarkers comprising panels of molecular species that are useful for the early detection of liver cancer, as well as methods of identifying such panels of metabolic biomarkers within biological samples, and methods of using such panels of metabolic biomarkers.

BACKGROUND

Hepatocellular carcinoma (HCC) is the most common type of liver cancer, and is responsible for an estimated 660,000 deaths worldwide. It is believed that HCC develops upon significant damage to the cellular machinery in the liver after sustained viral infections or cirrhosis. Hepatitis C virus (HCV) infection is of particular interest since an estimated 130-170 million people are infected with the virus. It is believed that HCV infection causes 25% of all reported cases of HCC. HCV viral infections can be currently diagnosed with an HCV antibody enzyme immunoassays but such testing cannot distinguish between acute and chronic infections. If a set of reliable biomarkers were available that can effectively identify HCV infected individuals who are in the early stages of HCC and potentially more receptive to treatments.

Metabolomics, in which a large number of small molecule metabolites are detected quantitatively, often in easily accessible biofluids such as blood and urine, can provide useful information regarding early biomarkers and altered metabolic pathways. As metabolites are the downstream products of genes and gene expression, they integrate many of the alterations caused by disease or other biological stresses. Metabolites are exquisitely sensitive to different biological states and therefore represent a promising approach to identify potential biomarkers. Several analytical techniques such as nuclear magnetic resonance (NMR), liquid chromatography-mass spectrometry (LC-MS) and gas chromatography-mass spectrometry (GC-MS) have been used to detect metabolic changes in a number of cancers including liver cancer. Several studies using a variety of analytical techniques have reported discovery of potential biomarkers in biological samples such as serum, plasma and urine of subjects with HCC relative to healthy controls. However, none of the studies have focused exclusively on altered metabolic pathways between HCV patients, who have high risk of developing HCC, and those who have developed HCC.

Metabolomics thus provides a powerful approach to identify small molecule biomarkers associated with cancer and other diseases. By focusing on the concentrations and fluxes of low molecular weight metabolites (<~1000 m/z) in biofluids, detailed information on biological systems and their concordant correlations across related disease states can be obtained.

The Human Metabolome Database (HMDB) is a freely available electronic database containing detailed information about small molecule metabolites found in the human body. It is intended to be used for applications in metabolomics, clinical chemistry, biomarker discovery and general education. The database is designed to contain or link three kinds of data: 1) chemical data, 2) clinical data, and 3) molecular biology/biochemistry data. The database (version 3.5) contains 40,446 metabolite entries including both water-soluble and lipid soluble metabolites as well as metabolites that would be regarded as either abundant (>1 µM) or relatively rare (<1 nM). Additionally, 5,235 protein (and DNA) sequences are linked to these metabolite entries. See Wishart, D. S., Tzur, D., Knox, C., et al., HMDB: the Human Metabolome Database, Nucleic Acids Res. 2007 January; 35(Database issue):D521-6; Wishart, D. S., Knox, C., Guo, A. C., et al., HMDB: a knowledgebase for the human metabolome, Nucleic Acids Res. 2009 37(Database issue):D603-610; Wishart, D. S., Jewison, T., Guo, A. C., Wilson, M., Knox, C., et al., HMDB 3.0—The Human Metabolome Database in 2013, Nucleic Acids Res. 2013. January 1; 41(D1):D801-7.

SUMMARY OF THE INVENTION

The present disclosure provides small molecule metabolic biomarkers comprising panels of metabolite species that are useful for the early detection of liver cancer, especially the early detection of hepatocellular carcinoma in the presence of hepatitis C virus (HCV) infection. Also included are methods of identifying such panels of metabolic biomarkers within biological samples, and methods of using such panels of metabolic biomarkers.

In certain aspects, a method of determining evidence of hepatocellular carcinoma in a sample of biofluid is provided, comprising the step of measuring the concentration of a selected metabolite species in a sample of a biofluid from a subject, wherein each metabolite species is a component of an identified panel of three to sixteen metabolite species, wherein a change in the concentration of at least one metabolite species is characteristic of a transition from infection with hepatitis C virus to hepatocellular carcinoma thereby determining evidence of hepatocellular carcinoma. In certain embodiments the method further comprising the step of: comparing the measured concentrations in the biofluid sample of each metabolite species to the prediction of a statistical model. In embodiments, the selected metabolite species of the identified panel is selected from the group consisting of 5-hydroxymethyl-2'-deoxyuridine, $N^2,N^2$-dimethylguanosine, methionine, uric acid, 1-methylinosine, 1-methylguanosine, 1-methyladenosine, xanthine, phenylalanine, 2-deoxyguanosine, tyrosine, N-carbamoyl-beta alanine, glycerol, aconitic acid, creatine, homocysteine, valine, cholyglycine, D-leucic acid, creatinine, 3-hydroxycapric acid and identifiable parts thereof.

In certain embodiments, the panel is selected from the group consisting of:
a. the panel consisting of uric acid; cholylglycine, 3-hydroxycapric acid, D-leucic acid, and xanthine;
b. the panel consisting of choline, creatinine and valine
c. the panel consisting of 5-hydroxymethyl-2'-deoxyuridine, $N^2,N^2$-dimethylguanosine, methionine, uric acid;
d. the panel consisting of 5-hydroxymethyl-2'-deoxyuridine, $N^2,N^2$-dimethylguanosine, methionine, 1-nethylguanosine;
e. the panel consisting of 5-hydroxymethyl-2'-deoxyuridine, N $N^2,N^2$-dimethylguanosine, methionine, 1-methylinosine;
f. the panel consisting of 5-hydroxymethyl-2'-deoxyuridine, $N^2,N^2$-dimethylguanosine, methionine, xanthine;
g. the panel consisting of 5-hydroxymethyl-2'-deoxyuridine, $N^2,N^2$-dimethylguanosine, methionine, 1-methyladenosine;
h. the panel consisting of 5-hydroxymethyl-2'-deoxyuridine, $N^2,N^2$-dimethylguanosine, methionine, phenylalanine;
i. the panel consisting of $N^2,N^2$-dimethylguanosine, methionine, uric acid, 1-methylinosine;
j. the panel consisting of $N^2,N^2$-dimethylguanosine, methionine, uric acid, 1-methylguanosine;
k. the panel consisting of 5-hydroxymethyl-2'-deoxyuridine, $N^2,N^2$-dimethylguanosine, methionine, phenylalanine;
l. the panel consisting of 5-hydroxymethyl-2'-deoxyuridine, $N^2,N^2$-dimethylguanosine, methionine, 2-deoxyguanosine;
m. the panel consisting of 5-hydroxymethyl-2'-deoxyuridine, $N^2,N^2$-dimethylguanosine, methionine, tyrosine;
n. the panel consisting of 5-hydroxymethyl-2'-deoxyuridine, $N^2,N^2$-dimethylguanosine, methionine, n-carbamoyl-beta alanine;
o. the panel consisting of $N^2,N^2$-dimethylguanosine, methionine, uric acid, 1-methyladenosine;
p. the panel consisting of $N^2,N^2$-dimethylguanosine, methionine, uric acid, xanthine;
q. the panel consisting of 5-hydroxymethyl-2'-deoxyuridine, $N^2,N^2$-dimethylguanosine, methionine, glycerol;
r. the panel consisting of $N^2,N^2$-dimethylguanosine, methionine, uric acid, phenylalanine;
s. the panel consisting of $N^2,N^2$-dimethylguanosine, methionine, uric acid, 2-deoxyguanosine;
t. the panel consisting of $N^2,N^2$-dimethylguanosine, methionine, uric acid, tyrosine; and
u. the panel consisting of $N^2,N^2$-dimethylguanosine, methionine, uric acid, N-carbamoyl-beta alanine.
v. the panel consisting of $N^2,N^2$-dimethylguanosine, methionine, uric acid, glycerol;
w. the panel consisting of 5-hydroxymethyl-2'-deoxyuridine, 2-deoxyguanosine, N-carbamoyl-beta alanine, $N^2,N^2$-dimethylguanosine;
x. the panel consisting of methionine, uric acid, xanthine, phenylalanine;
y. the panel consisting of 5-hydroxymethyl-2'-deoxyuridine, $N^2,N^2$-dimethylguanosine, methionine, aconitic acid;
z. the panel consisting of 5-hydroxymethyl-2'-deoxyuridine, $N^2,N^2$-dimethylguanosine, methionine, creatine;
aa. the panel consisting of 5-hydroxymethyl-2'-deoxyuridine, 2-deoxyguanosine, N-carbamoyl-beta alanine, methionine;
bb. the panel consisting of methionine, uric acid, phenylalanine, 2-deoxyguanosine;
cc. the panel consisting of 5-hydroxymethyl-2'-deoxyuridine, 2-deoxyguanosine, N-carbamoyl-beta alanine, uric acid;
dd. the panel consisting of methionine, uric acid, phenylalanine, tyrosine;
ee. the panel consisting of $N^2,N^2$-dimethylguanosine, methionine, uric acid, aconitic acid;
ff. the panel consisting of $N^2,N^2$-dimethylguanosine, methionine, uric acid, creatine;
gg. the panel consisting of 5-hydroxymethyl-2'-deoxyuridine, $N^2,N^2$-dimethylguanosine, methionine, homocysteine;
hh. the panel consisting of 5-hydroxymethyl-2'-deoxyuridine, 2-deoxyguanosine, N-carbamoyl-beta alanine, 1-methyladenosine;
ii. the panel consisting of 5-hydroxymethyl-2'-deoxyuridine, 2-deoxyguanosine, N-carbamoyl-beta alanine, xanthine;
jj. the panel consisting of $N^2,N^2$-dimethylguanosine, methionine, uric acid, homocysteine;
kk. the panel consisting of 5-hydroxymethyl-2'-deoxyuridine, 2-deoxyguanosine, N-carbamoyl-beta alanine, tyrosine;
ll. the panel consisting of 5-hydroxymethyl-2'-deoxyuridine, 2-deoxyguanosine, N-carbamoyl-beta alanine, glycerol; mm the panel consisting of 5-hydroxymethyl-2'-deoxyuridine, 2-deoxyguanosine, N-carbamoyl-beta alanine, creatine;
nn. the panel consisting of methionine, uric acid, phenylalanine, homocysteine
oo. the panel consisting of 5-hydroxymethyl-2'-deoxyuridine, 2-deoxyguanosine, N-carbamoyl-beta alanine, aconitic acid;
pp. the panel consisting of 5-hydroxymethyl-2'-deoxyuridine, 2-deoxyguanosine, N-carbamoyl-beta alanine, homocysteine;
qq. the panel consisting of methionine, uric acid, xanthine, phenylalanine, tyrosine.
rr. the panel consisting of 5-hydroxymethyl-2'-deoxyuridine, $N^2,N^2$-dimethylguanosine, methionine, uric acid, 1-methylguanosine
ss. the panel consisting of 5-hydroxymethyl-2'-deoxyuridine, $N^2,N^2$-dimethylguanosine, methionine, uric acid, 1-methylinosine;
tt. the panel consisting of 5-hydroxymethyl-2'-deoxyuridine, $N^2,N^2$-dimethylguanosine, methionine, uric acid, 1-methylinosine, 1-methylguanosine;
uu. the panel consisting of 5-hydroxymethyl-2'-deoxyuridine, $N^2,N^2$-dimethylguanosine, methionine, uric acid, 1-methylinosine, 1-methylguanosine, 1-methyladenosine;
vv. the panel consisting of 5-hydroxymethyl-2'-deoxyuridine, $N^2,N^2$-dimethylguanosine, methionine, uric acid, 1-methylinosine, 1-methylguanosine, 1-methyladenosine, xanthine;
ww. the panel consisting of 5-hydroxymethyl-2'-deoxyuridine, $N^2,N^2$-dimethylguanosine, methionine, uric acid, 1-methylinosine, 1-methylguanosine, 1-methyladenosine, xanthine, phenylalanine;
xx. the panel consisting of 5-hydroxymethyl-2'-deoxyuridine, $N^2,N^2$-dimethylguanosine, methionine, uric acid, 1-methylinosine, 1-methylguanosine, 1-methyladenosine, xanthine, phenylalanine, 2-deoxyguanosine;
yy. the panel consisting of methionine, uric acid, xanthine, phenylalanine, tyrosine, n-carbamoyl-beta alanine, glycerol, aconitic acid, creatine, homocysteine;

zz. the panel consisting of 5-hydroxymethyl-2'-deoxyuridine, $N^2,N^2$-dimethylguanosine, methionine, uric acid, 1-methylinosine, 1-methylguanosine, 1-methyladenosine, xanthine, phenylalanine, 2-deoxyguanosine, tyrosine;

aaa. the panel consisting of 5-hydroxymethyl-2'-deoxyuridine, $N^2,N^2$-dimethylguanosine, methionine, uric acid, 1-methylinosine, 1-methylguanosine, 1-methyladenosine, xanthine, phenylalanine, 2-deoxyguanosine, tyrosine, N-carbamoyl-beta alanine;

bbb. the panel consisting of 5-hydroxymethyl-2'-deoxyuridine, $N^2,N^2$-dimethylguanosine, methionine, uric acid, 1-methylinosine, 1-methylguanosine, 1-methyladenosine, xanthine, phenylalanine, 2-deoxyguanosine, tyrosine, N-carbamoyl-beta alanine, glycerol;

ccc. 5-hydroxymethyl-2'-deoxyuridine, $N^2,N^2$-dimethylguanosine, methionine, uric acid, 1-methylinosine, 1-methylguanosine, 1-methyladenosine, xanthine, phenylalanine, 2-deoxyguanosine, tyrosine, N-carbamoyl-beta alanine, glycerol, aconitic acid;

ddd. the panel consisting of methionine, uric acid, 1-methylinosine, 1-methylguanosine, 1-methyladenosine, xanthine, phenylalanine, 2-deoxyguanosine, tyrosine, N-carbamoyl-beta alanine, glycerol, aconitic acid, creatine, homocysteine;

eee. the panel consisting of 5-hydroxymethyl-2'-deoxyuridine, $N^2,N^2$-dimethylguanosine, methionine, uric acid, 1-methylinosine, 1-methylguanosine, 1-methyladenosine, xanthine, phenylalanine, 2-deoxyguanosine, tyrosine, N-carbamoyl-beta alanine, glycerol, aconitic acid, creatine;

fff. the panel consisting of 5-hydroxymethyl-2'-deoxyuridine, $N^2,N^2$-dimethylguanosine, methionine, uric acid, 1-methylinosine, 1-methylguanosine, 1-methyladenosine, xanthine, phenylalanine, 2-deoxyguanosine, tyrosine, N-carbamoyl-beta alanine, glycerol, aconitic acid, creatine, homocysteine;

ggg. the panel consisting of 5-hydroxymethyl-2'-deoxyuridine, $N^2,N^2$-dimethylguanosine, methionine, uric acid, 1-methylinosine, 1-methylguanosine, 1-methyladenosine, xanthine, phenylalanine, 2-deoxyguanosine, tyrosine, N-carbamoyl-beta alanine, glycerol, aconitic acid, creatine, homocysteine, valine, cholyglycine, d-leucic acid, creatinine, 3-hydroxycapric acid.

Typically, the panel comprises metabolite species that have been identified by a plurality of methods selected from nuclear magnetic resonance (NMR) spectrometry, gas chromatography-mass spectrometry (GC-MS), liquid chromatography-mass spectrometry (LC-MS), correlation spectroscopy (COSy), nuclear Overhauser effect spectroscopy (NOESY), rotating frame nuclear Overhauser effect spectroscopy (ROESY), LC-TOF-MS, LC-MS/MS, capillary electrophoresis-mass spectrometry, nuclear magnetic resonance (NMR) spectrometry and liquid chromatography-mass spectrometry (LC-MS).

In certain embodiments, the components of the panel are selected by the steps of identifying metabolite species that are present in the biofluid samples from hepatocellular carcinoma (HCC) subjects and the samples from subjects infected with hepatitis C virus (HCV); selecting the identified metabolite species the difference in concentration in the biofluid samples from the HCC subjects and the biofluid samples from the HCV subjects is significant at the level of $p<0.05$; and grouping the identified metabolite species to produce an identified panel of metabolite species wherein the average p-value of the metabolite species of a panel is in the range of 0.003 to 0.03.

Generally, the sample comprises a biofluid selected from blood, plasma, serum, sweat, saliva, sputum or urine. In certain embodiments, the biofluid is serum.

In other embodiments, a panel of metabolic species is provided, which is selected from the group consisting of:

a. the panel consisting of uric acid; cholylglycine, 3-hydroxycapric acid, D-leucic acid, and xanthine, b. the panel consisting of choline, creatinine and valine c. the panel consisting of 5-hydroxymethyl-2'-deoxyuridine, $N^2,N^2$-dimethylguanosine, methionine, uric acid;

d. the panel consisting of 5-hydroxymethyl-2'-deoxyuridine, $N^2,N^2$-dimethylguanosine, methionine, 1-nethylguanosine;

e. the panel consisting of 5-hydroxymethyl-2'-deoxyuridine, N $N^2,N^2$-dimethylguanosine, methionine, 1-methylinosine;

f. the panel consisting of 5-hydroxymethyl-2'-deoxyuridine, $N^2,N^2$-dimethylguanosine, methionine, xanthine;

g. the panel consisting of 5-hydroxymethyl-2'-deoxyuridine, $N^2,N^2$-dimethylguanosine, methionine, 1-methyladenosine;

h. the panel consisting of 5-hydroxymethyl-2'-deoxyuridine, $N^2,N^2$-dimethylguanosine, methionine, phenylalanine;

i. the panel consisting of $N^2,N^2$-dimethylguanosine, methionine, uric acid, 1-methylinosine;

j. the panel consisting of $N^2,N^2$-dimethylguanosine, methionine, uric acid, 1-methylguanosine;

k. the panel consisting of 5-hydroxymethyl-2'-deoxyuridine, $N^2,N^2$-dimethylguanosine, methionine, phenylalanine;

l. the panel consisting of 5-hydroxymethyl-2'-deoxyuridine, $N^2,N^2$-dimethylguanosine, methionine, 2-deoxyguanosine;

m. the panel consisting of 5-hydroxymethyl-2'-deoxyuridine, $N^2,N^2$-dimethylguanosine, methionine, tyrosine;

n. the panel consisting of 5-hydroxymethyl-2'-deoxyuridine, $N^2,N^2$-dimethylguanosine, methionine, n-carbamoyl-beta alanine;

o. the panel consisting of $N^2,N^2$-dimethylguanosine, methionine, uric acid, 1-methyladenosine;

p. the panel consisting of $N^2,N^2$-dimethylguanosine, methionine, uric acid, xanthine;

q. the panel consisting of 5-hydroxymethyl-2'-deoxyuridine, $N^2,N^2$-dimethylguanosine, methionine, glycerol;

r. the panel consisting of $N^2,N^2$-dimethylguanosine, methionine, uric acid, phenylalanine;

s. the panel consisting of $N^2,N^2$-dimethylguanosine, methionine, uric acid, 2-deoxyguanosine;

t. the panel consisting of $N^2,N^2$-dimethylguanosine, methionine, uric acid, tyrosine; and u. the panel consisting of $N^2,N^2$-dimethylguanosine, methionine, uric acid, N-carbamoyl-beta alanine.

v. the panel consisting of $N^2,N^2$-dimethylguanosine, methionine, uric acid, glycerol;

w. the panel consisting of 5-hydroxymethyl-2'-deoxyuridine, 2-deoxyguanosine, N-carbamoyl-beta alanine, $N^2,N^2$-dimethylguanosine;

x. the panel consisting of methionine, uric acid, xanthine, phenylalanine;

y. the panel consisting of 5-hydroxymethyl-2'-deoxyuridine, $N^2,N^2$-dimethylguanosine, methionine, aconitic acid;

z. the panel consisting of 5-hydroxymethyl-2'-deoxyuridine, $N^2,N^2$-dimethylguanosine, methionine, creatine;

aa. the panel consisting of 5-hydroxymethyl-2'-deoxyuridine, 2-deoxyguanosine, N-carbamoyl-beta alanine, methionine;
bb. the panel consisting of methionine, uric acid, phenylalanine, 2-deoxyguanosine;
cc. the panel consisting of 5-hydroxymethyl-2'-deoxyuridine, 2-deoxyguanosine, N-carbamoyl-beta alanine, uric acid;
dd. the panel consisting of methionine, uric acid, phenylalanine, tyrosine;
ee. the panel consisting of $N^2,N^2$-dimethylguanosine, methionine, uric acid, aconitic acid;
ff. the panel consisting of $N^2,N^2$-dimethylguanosine, methionine, uric acid, creatine;
gg. the panel consisting of 5-hydroxymethyl-2'-deoxyuridine, $N^2,N^2$-dimethylguanosine, methionine, homocysteine;
hh. the panel consisting of 5-hydroxymethyl-2'-deoxyuridine, 2-deoxyguanosine, N-carbamoyl-beta alanine, 1-methyladenosine;
ii. the panel consisting of 5-hydroxymethyl-2'-deoxyuridine, 2-deoxyguanosine, N-carbamoyl-beta alanine, xanthine;
jj. the panel consisting of $N^2,N^2$-dimethylguanosine, methionine, uric acid, homocysteine;
kk. the panel consisting of 5-hydroxymethyl-2'-deoxyuridine, 2-deoxyguanosine, N-carbamoyl-beta alanine, tyrosine;
ll. the panel consisting of 5-hydroxymethyl-2'-deoxyuridine, 2-deoxyguanosine, N-carbamoyl-beta alanine, glycerol;
mm. the panel consisting of 5-hydroxymethyl-2'-deoxyuridine, 2-deoxyguanosine, N-carbamoyl-beta alanine, creatine;
nn. the panel consisting of methionine, uric acid, phenylalanine, homocysteine
oo. the panel consisting of 5-hydroxymethyl-2'-deoxyuridine, 2-deoxyguanosine, N-carbamoyl-beta alanine, aconitic acid;
pp. the panel consisting of 5-hydroxymethyl-2'-deoxyuridine, 2-deoxyguanosine, N-carbamoyl-beta alanine, homocysteine;
qq. the panel consisting of methionine, uric acid, xanthine, phenylalanine, tyrosine;
rr. the panel consisting of 5-hydroxymethyl-2'-deoxyuridine, $N^2,N^2$-dimethylguanosine, methionine, uric acid, 1-methylguanosine
ss. the panel consisting of 5-hydroxymethyl-2'-deoxyuridine, $N^2,N^2$-dimethylguanosine, methionine, uric acid, 1-methylinosine;
tt. the panel consisting of 5-hydroxymethyl-2'-deoxyuridine, $N^2,N^2$-dimethylguanosine, methionine, uric acid, 1-methylinosine, 1-methylguanosine;
uu. the panel consisting of 5-hydroxymethyl-2'-deoxyuridine, $N^2,N^2$-dimethylguanosine, methionine, uric acid, 1-methylinosine, 1-methylguanosine, 1-methyladenosine;
vv. the panel consisting of 5-hydroxymethyl-2'-deoxyuridine, $N^2,N^2$-dimethylguanosine, methionine, uric acid, 1-methylinosine, 1-methylguanosine, 1-methyladenosine, xanthine;
ww. the panel consisting of 5-hydroxymethyl-2'-deoxyuridine, $N^2,N^2$-dimethylguanosine, methionine, uric acid, 1-methylinosine, 1-methylguanosine, 1-methyladenosine, xanthine, phenylalanine;
xx. the panel consisting of 5-hydroxymethyl-2'-deoxyuridine, $N^2,N^2$-dimethylguanosine, methionine, uric acid, 1-methylinosine, 1-methylguanosine, 1-methyladenosine, xanthine, phenylalanine, 2-deoxyguanosine;
yy. the panel consisting of methionine, uric acid, xanthine, phenylalanine, tyrosine, n-carbamoyl-beta alanine, glycerol, aconitic acid, creatine, homocysteine;
zz. the panel consisting of 5-hydroxymethyl-2'-deoxyuridine, $N^2,N^2$-dimethylguanosine, methionine, uric acid, 1-methylinosine, 1-methylguanosine, 1-methyladenosine, xanthine, phenylalanine, 2-deoxyguanosine, tyrosine;
aaa. the panel consisting of 5-hydroxymethyl-2'-deoxyuridine, $N^2,N^2$-dimethylguanosine, methionine, uric acid, 1-methylinosine, 1-methylguanosine, 1-methyladenosine, xanthine, phenylalanine, 2-deoxyguanosine, tyrosine, N-carbamoyl-beta alanine;
bbb. the panel consisting of 5-hydroxymethyl-2'-deoxyuridine, $N^2,N^2$-dimethylguanosine, methionine, uric acid, 1-methylinosine, 1-methylguanosine, 1-methyladenosine, xanthine, phenylalanine, 2-deoxyguanosine, tyrosine, N-carbamoyl-beta alanine, glycerol;
ccc. 5-hydroxymethyl-2'-deoxyuridine, $N^2,N^2$-dimethylguanosine, methionine, uric acid, 1-methylinosine, 1-methylguanosine, 1-methyladenosine, xanthine, phenylalanine, 2-deoxyguanosine, tyrosine, N-carbamoyl-beta alanine, glycerol, aconitic acid;
ddd. the panel consisting of methionine, uric acid, 1-methylinosine, 1-methylguanosine, 1-methyladenosine, xanthine, phenylalanine, 2-deoxyguanosine, tyrosine, N-carbamoyl-beta alanine, glycerol, aconitic acid, creatine, homocysteine;
eee. the panel consisting of 5-hydroxymethyl-2'-deoxyuridine, $N^2,N^2$-dimethylguanosine, methionine, uric acid, 1-methylinosine, 1-methylguanosine, 1-methyladenosine, xanthine, phenylalanine, 2-deoxyguanosine, tyrosine, N-carbamoyl-beta alanine, glycerol, aconitic acid, creatine;
fff. the panel consisting of 5-hydroxymethyl-2'-deoxyuridine, $N^2,N^2$-dimethylguanosine, methionine, uric acid, 1-methylinosine, 1-methylguanosine, 1-methyladenosine, xanthine, phenylalanine, 2-deoxyguanosine, tyrosine, N-carbamoyl-beta alanine, glycerol, aconitic acid, creatine, homocysteine;
ggg. the panel consisting of 5-hydroxymethyl-2'-deoxyuridine, $N^2,N^2$-dimethylguanosine, methionine, uric acid, 1-methylinosine, 1-methylguanosine, 1-methyladenosine, xanthine, phenylalanine, 2-deoxyguanosine, tyrosine, N-carbamoyl-beta alanine, glycerol, aconitic acid, creatine, homocysteine, valine, cholyglycine, d-leucic acid, creatinine, 3-hydroxycapric acid.

In other embodiments, a kit for testing a sample, is provided, the kit including aliquots of standards of each component of a panel of metabolic species, an aliquot of an internal standard; and an aliquot of a control biofluid wherein the kit is used for detecting evidence of hepatocellular carcinoma in a sample of biofluid from a subject. Generally, the control biofluid is a biofluid corresponding to the sample of biofluid to be tested from a control source that belongs to the same biological species as the subject. Generally, the biofluid is selected from blood, plasma, serum, sweat, saliva, sputum or urine. Usually the kit further includes instructions for use.

BRIEF DESCRIPTION OF THE DRAWINGS

The above-mentioned aspects of the present teachings and the manner of obtaining them will become more apparent and the teachings will be better understood by reference to the following description of the embodiments taken in conjunction with the accompanying drawings, in which corresponding reference characters indicate corresponding parts throughout the several views.

FIG. 1A, uric acid; FIG. 1B, cholylglycine; FIG. 1C, 3-hydroxycapric acid; FIG. 1D, D-leucic acid; FIG. 1E, xanthine.

FIG. 2A shows PLS-DA predicted model denoted with a dashed line (sensitivity=0.92, specificity=0.62) between individuals with HCC (triangles) on the left and individuals with HCV infection (asterisks) on the right. FIG. 2B shows the ROC curve for the cross-validated predicted class values (AUROC=0.89).

FIG. 3A, tyrosine; FIG. 3E, 1-methylguanosine; FIG. 3J, 1-methyladenosine; FIG. 3P, uric acid.

DETAILED DESCRIPTION OF EXEMPLARY EMBODIMENTS

Figure 1A:
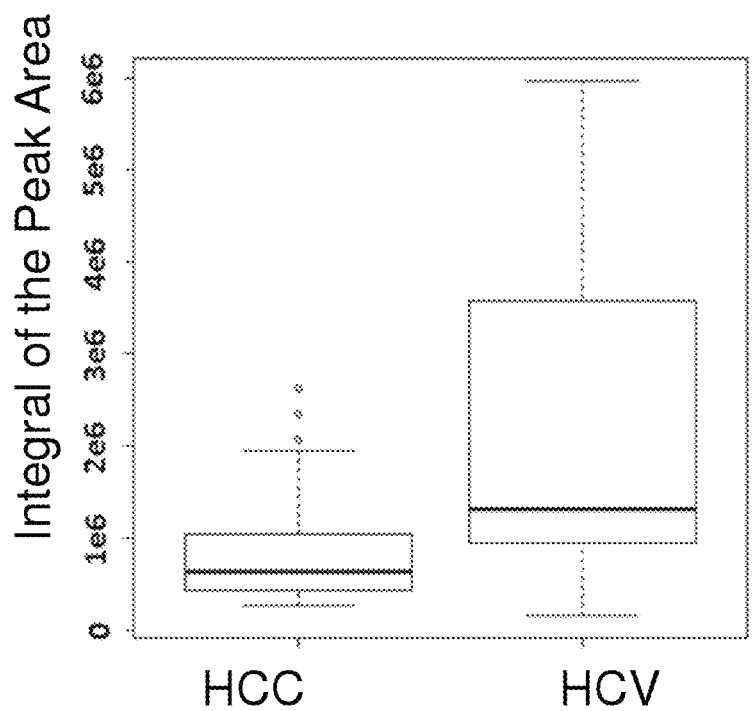
FIG. 1A-FIG. 1E show box-and-whisker plots comparing the groups "HCC" and "HCV" for several biomarkers, in which the y axis for each plot indicates the integral of the peak area for that compound. The horizontal line in the middle portion of the box represents the median value; upper and lower whiskers, show 95th and 5th and percentiles, respectively. The top and bottom boundaries of each box, show 75th percentiles and 25th, respectively.
Figure 1B:
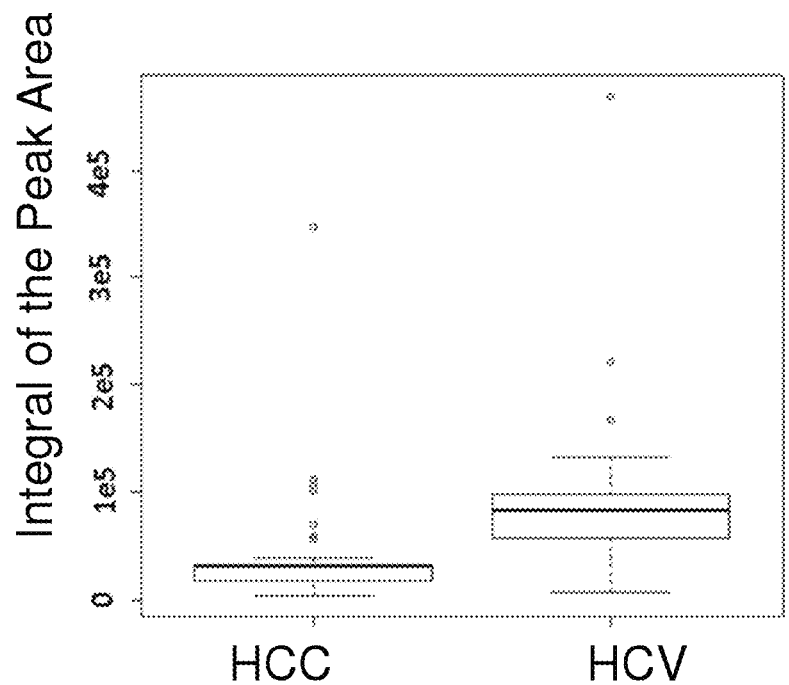
Figure 1C:
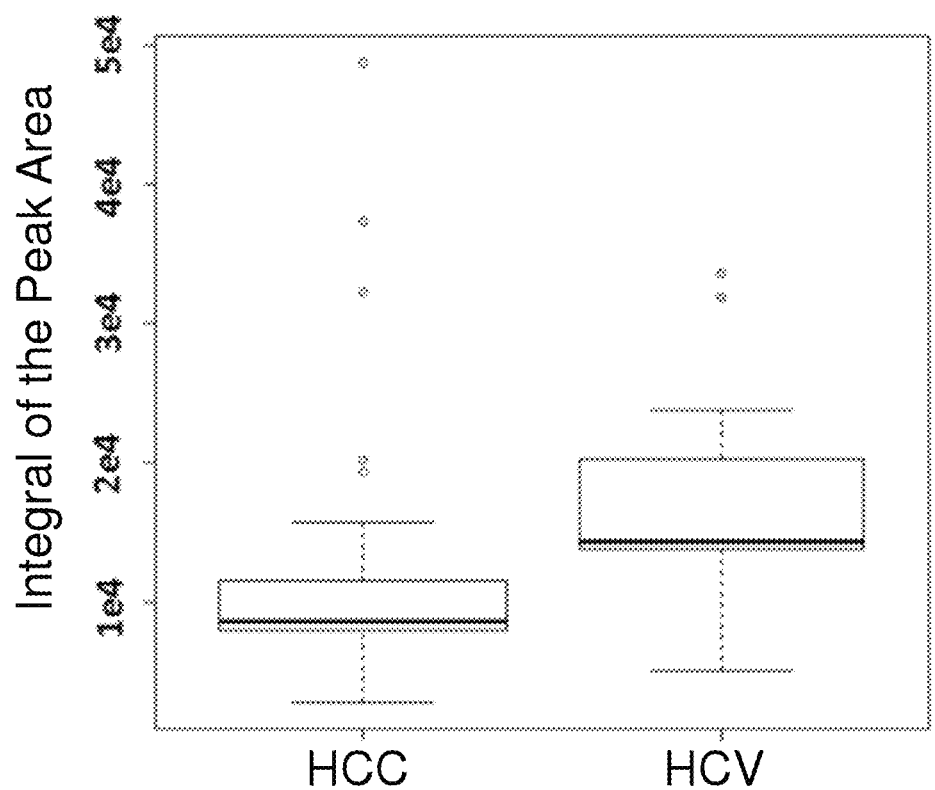
Figure 1D:
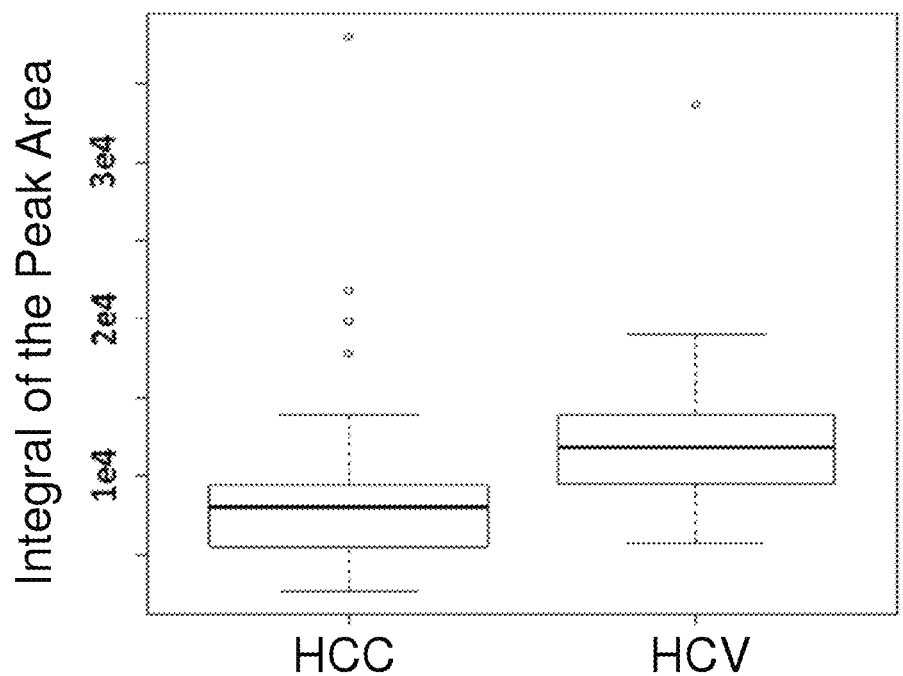
Figure 1E:
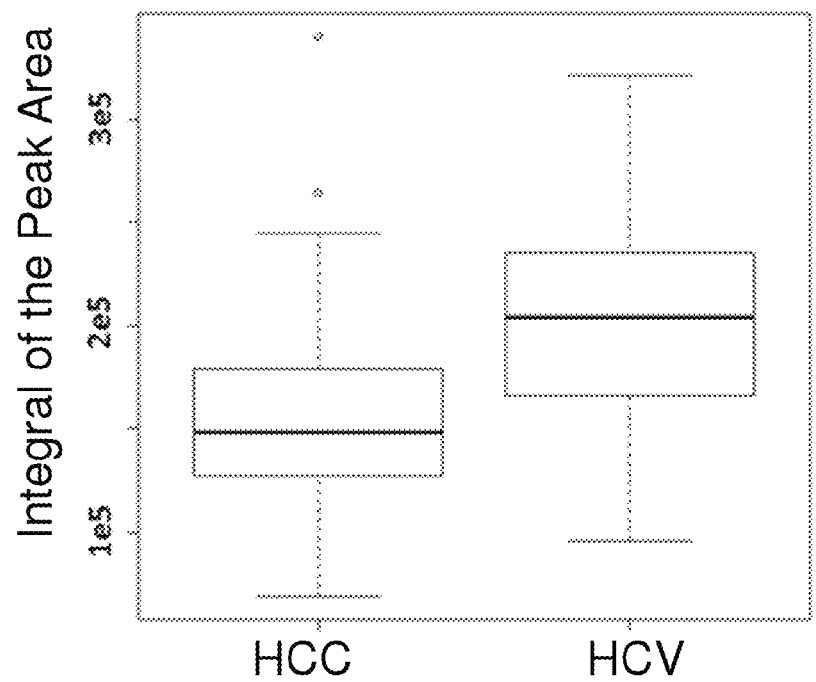

The present disclosure describes the use of LC-MS and multivariate statistical analysis to detect molecular changes in human blood serum samples by comparing the metabolic profiles of patients with HCV infection, and patients with HCC, to identify a metabolite profile of HCC, and biomarkers for HCC, as well as methods for monitoring the progression of HCC.

The present disclosure provides monitoring tests based on panels of selected biomarkers that have been selected as being effective in detecting HCV infection and HCC, as well as the progression of HCC. The tests have high degrees of clinical sensitivity and clinical specificity. The tests are based on biological sample classification methods that use a combination of mass spectrometry ("MS") techniques. More particularly, the present teachings take advantage of liquid chromatography-mass spectrometry ("LC-MS") to identify small molecule biomarkers comprising a set of metabolite biomarker compounds found in patient serum samples.

Unless defined otherwise, all technical and scientific terms used herein have the meaning commonly understood by a person skilled in the art to which this invention belongs. Numbers in scientific notation are expressed as product of a coefficient between 1 and 10 and ten raised to an integer power (e.g., $9.6 \times 10^{-4}$), or abbreviated as the coefficient followed by "E," followed by the exponent (e.g., 9.6E−04).

As used herein, "metabolite" refers to any substance produced or used during all the physical and chemical processes within the body that create and use energy, such as: digesting food and nutrients, eliminating waste through urine and feces, breathing, circulating blood, and regulating temperature. The term "metabolic precursors" refers to compounds from which the metabolites are made. The term "metabolic products" refers to any substance that is part of a metabolic pathway (e.g. metabolite, metabolic precursor). The term "metabolite species" includes metabolites and identifiable parts or moieties of metabolites, such as lipid, unsaturated lipid or glycoprotein.

As used herein, "biological sample" refers to a sample obtained from a subject. In preferred embodiments, biological sample can be selected, without limitation, from the group of biological fluids ("biofluids") consisting of blood, plasma, serum, sweat, saliva, including sputum, urine, and the like. As used herein, "serum" refers to the fluid portion of the blood obtained after removal of the fibrin clot and blood cells, distinguished from the plasma in circulating blood. As used herein, "plasma" refers to the fluid, non-cellular portion of the blood, as distinguished from the serum, which is obtained after coagulation.

As used herein, "subject" refers to any warm-blooded animal, particularly including a member of the class Mammalia such as, without limitation, humans and non-human primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex and, thus, includes adult and newborn subjects, whether male or female. As used herein, "normal control subjects" or "normal controls" means healthy subjects who are clinically free of cancer. "Normal control sample" or "control sample" refers to a sample of biofluid that has been obtained from a normal control subject.

As used herein, "detecting" refers to methods which include identifying the presence or absence of substance(s) in the sample, quantifying the amount of substance(s) in the sample, and/or qualifying the type of substance. "Detecting" likewise refers to methods which include identifying the presence or absence of HCV infection and HCC or the progression of HCC.

"Mass spectrometer" refers to a gas phase ion spectrometer that measures a parameter that can be translated into mass-to-charge ratios of gas phase ions. Mass spectrometers generally include an ion source and a mass analyzer. Examples of mass spectrometers are time-of-flight, magnetic sector, quadrupole filter, ion trap, ion cyclotron resonance, electrostatic sector analyzer and hybrids of these. "Mass spectrometry" refers to the use of a mass spectrometer to detect gas phase ions.

It is to be understood that this invention is not limited to the particular component parts of a device described or process steps of the methods described, as such devices and methods may vary. It is also to be understood that the terminology used herein is for purposes of describing particular embodiments only, and is not intended to be limiting. As used in the specification and the appended claims, the singular forms "a," "an," and "the" include plural referents unless the context clearly indicates otherwise. The terms "comprises," "comprising," and the like are intended to have the broad meaning ascribed to them in U.S. Patent Law and can mean "includes," "including" and the like.

Metabolite profiling uses high-throughput analytical methods such as nuclear magnetic resonance spectroscopy and mass spectroscopy for the quantitative analysis of hundreds of small molecules (less than ~1000 Daltons) present in biological samples. Owing to the complexity of the metabolic profile, multivariate statistical methods are extensively used for data analysis. The high sensitivity of metabolite profiles to even subtle stimuli can provide the means to detect the early onset of various biological perturbations in real time.

While these metabolite profiles were discovered using LC-MS methods, one of ordinary skill in the art will recognize that these identified biomarkers can be detected by alternative methods of suitable sensitivity, such as HPLC, immunoassays, enzymatic assays or clinical chemistry methods.

In one embodiment of the invention, samples may be collected from individuals over a longitudinal period of time. Obtaining numerous samples from an individual over a period of time can be used to verify results from earlier detections and/or to identify an alteration in marker pattern as a result of, for example, pathology. In preferred embodiments, the present disclosure provides methods of monitoring the progression of HCV infection and HCC. In certain embodiments, the present disclosure provides methods of assessing the effectiveness of the treatment of HCV infection and HCC.

In one embodiment of the invention, the samples are analyzed without additional preparation and/or separation procedures. In another embodiment of the invention, sample preparation and/or separation can involve, without limitation, any of the following procedures, depending on the type of sample collected and/or types of metabolic products searched: removal of high abundance polypeptides or proteins (e.g., albumin, and transferrin); addition of preservatives and calibrants, desalting of samples; concentration of sample substances; protein digestions; and fraction collection. In yet another embodiment of the invention, sample preparation techniques concentrate information-rich metabolic products and deplete polypeptides and proteins or other substances that would carry little or no information such as those that are highly abundant in serum.

In another embodiment of the invention, sample preparation takes place in a manifold or preparation/separation device. Such a preparation/separation device may, for example, be a microfluidics device, such as a cassette. In yet another embodiment of the invention, the preparation/separation device interfaces directly or indirectly with a detection device. Such a preparation/separation device may, for example, be a fluidics device.

In another embodiment of the invention, the removal of undesired polypeptides (e.g., high abundance, uninformative, or undetectable polypeptides) can be achieved using high affinity reagents, high molecular weight filters, column purification, ultracentrifugation and/or electrodialysis. High affinity reagents include antibodies that selectively bind to high abundance polypeptides or reagents that have a specific pH, ionic value, or detergent strength. High molecular weight filters include membranes that separate molecules on the basis of size and molecular weight. Such filters may further employ reverse osmosis, nanofiltration, ultrafiltration and microfiltration.

Ultracentrifugation constitutes another method for removing undesired polypeptides. Ultracentrifugation is the centrifugation of a sample at about 60,000 rpm while monitoring with an optical system the sedimentation (or lack thereof) of particles. Finally, electrodialysis is an electromembrane process in which ions are transported through ion permeable membranes from one solution to another under the influence of a potential gradient. Since the membranes used in electrodialysis have the ability to selectively transport ions having positive or negative charge and reject ions of the opposite charge, electrodialysis is useful for concentration, removal, or separation of electrolytes.

In another embodiment of the invention, the manifold or microfluidics device performs electrodialysis to remove high molecular weight polypeptides or undesired polypeptides. Electrodialysis can be used first to allow only molecules under approximately 35-30 kD to pass through into a second chamber. A second membrane with a very small molecular weight cutoff (roughly 500 D) allows smaller molecules to exit the second chamber.

Upon preparation of the samples, metabolic products of interest may be separated in another embodiment of the invention. Separation can take place in the same location as the preparation or in another location. In one embodiment of the invention, separation occurs in the same microfluidics device where preparation occurs, but in a different location on the device. Samples can be removed from an initial manifold location to a microfluidics device using various means, including an electric field. In another embodiment of the invention, the samples are concentrated during their migration to the microfluidics device using reverse phase beads and an organic solvent elution such as 50% methanol. This elutes the molecules into a channel or a well on a separation device of a microfluidics device.

Chromatography constitutes another method for separating subsets of substances. Chromatography is based on the differential absorption and elution of different substances. Liquid chromatography (LC), for example, involves the use of fluid carrier over a non-mobile phase. Conventional LC columns have an in inner diameter of roughly 4.6 mm and a flow rate of roughly 1 ml/min Micro-LC has an inner diameter of roughly 1.0 mm and a flow rate of roughly 40 µl/min Capillary LC utilizes a capillary with an inner diameter of roughly 300 µm and a flow rate of approximately 5 µl/min Nano-LC is available with an inner diameter of 50 µm-1 mm and flow rates of 200 nl/min. The sensitivity of nano-LC as compared to HPLC is approximately 3700 fold. Other types of chromatography suitable for additional embodiments of the invention include, without limitation, thin-layer chromatography (TLC), reverse-phase chromatography, high-performance liquid chromatography (HPLC), and gas chromatography (GC).

In another embodiment of the invention, the samples are separated using capillary electrophoresis separation. This will separate the molecules based on their electrophoretic mobility at a given pH (or hydrophobicity). In another embodiment of the invention, sample preparation and separation are combined using microfluidics technology. A microfluidic device is a device that can transport liquids including various reagents such as analytes and elutions between different locations using microchannel structures.

Suitable detection methods are those that have a sensitivity for the detection of an analyte in a biofluid sample of at least 50 µM. In certain embodiments, the sensitivity of the detection method is at least 1 µM. In other embodiments, the sensitivity of the detection method is at least 1 nM.

In one embodiment of the invention, the sample may be delivered directly to the detection device without preparation and/or separation beforehand. In another embodiment of the invention, once prepared and/or separated, the metabolic products are delivered to a detection device, which detects them in a sample. In another embodiment of the invention, metabolic products in elutions or solutions are delivered to a detection device by electrospray ionization (ESI). In yet another embodiment of the invention, nanospray ionization (NSI) is used. Nanospray ionization is a miniaturized version of ESI and provides low detection limits using extremely limited volumes of sample fluid.

In another embodiment of the invention, separated metabolic products are directed down a channel that leads to an electrospray ionization emitter, which is built into a microfluidic device (an integrated ESI microfluidic device). Such integrated ESI microfluidic device may provide the detection device with samples at flow rates and complexity levels that are optimal for detection. Furthermore, a microfluidic device may be aligned with a detection device for optimal sample capture.

Suitable detection devices can be any device or experimental methodology that is able to detect metabolic product presence and/or level, including, without limitation, IR (infrared spectroscopy), NMR (nuclear magnetic resonance), including variations such as correlation spectroscopy (COSy), nuclear Overhauser effect spectroscopy (NOESY), and rotating frame nuclear Overhauser effect spectroscopy (ROESY), and Fourier Transform (FT), 2-D PAGE technology, Western blot technology, tryptic mapping, in vitro biological assay, immunological analysis, LC-MS (liquid chromatography-mass spectrometry), LC-TOF-MS, LC-QTOF, LC-MS/MS, and MS (mass spectrometry).

For analysis relying on the application of NMR spectroscopy, the spectroscopy may be practiced as one-, two-, or multidimensional NMR spectroscopy or by other NMR spectroscopic examining techniques, among others also coupled with chromatographic methods (for example, as LC-NMR). In addition to the determination of the metabolic product in question, $^1$H-NMR spectroscopy offers the possibility of determining further metabolic products in the same investigative run. Combining the evaluation of a plurality of metabolic products in one investigative run can be employed for so-called "pattern recognition". Typically, the strength of evaluations and conclusions that are based on a profile of selected metabolites, i.e., a panel of identified biomarkers, is improved compared to the isolated determination of the concentration of a single metabolite.

For immunological analysis, for example, the use of immunological reagents (e.g. antibodies), generally in conjunction with other chemical and/or immunological reagents, induces reactions or provides reaction products which then permit detection and measurement of the whole group, a subgroup or a subspecies of the metabolic product(s) of interest. Suitable immunological detection methods with high selectivity and high sensitivity (10-1000 pg, or 0.02-2 pmoles), e.g., Baldo, B. A., et al. 1991, A Specific, Sensitive and High-Capacity Immunoassay for PAF, Lipids 26(12): 1136-1139), that are capable of detecting 0.5-21 ng/ml of an analyte in a biofluid sample (Cooney, S. J., et al., Quantitation by Radioimmunoassay of PAF in Human Saliva), Lipids 26(12): 1140-1143).

In one embodiment of the invention, mass spectrometry is relied upon to detect metabolic products present in a given sample. In another embodiment of the invention, an ESI-MS detection device is relied upon to detect metabolic products present in a given sample. Such an ESI-MS may utilize a time-of-flight (TOF) mass spectrometry system. Quadrupole mass spectrometry, ion trap mass spectrometry, and Fourier transform ion cyclotron resonance (FT-ICR) are likewise contemplated in additional embodiments of the invention.

In another embodiment of the invention, the detection device interfaces with a separation/preparation device or microfluidic device, which allows for quick assaying of many, if not all, of the metabolic products in a sample. A mass spectrometer may be utilized that will accept a continuous sample stream for analysis and provide high sensitivity throughout the detection process (e.g., an ESI-MS). In another embodiment of the invention, a mass spectrometer interfaces with one or more electrosprays, two or more electrosprays, three or more electrosprays or four or more electrosprays. Such electrosprays can originate from a single or multiple microfluidic devices.

In another embodiment of the invention, the detection system utilized allows for the capture and measurement of most or all of the metabolic products introduced into the detection device. In another embodiment of the invention, the detection system allows for the detection of change in a defined combination ("profile," "panel," "ensemble, or "composite") of metabolic products.

Profiles of metabolites in blood serum were constructed using NMR spectroscopy, LC-MS, and statistical analysis methods. The metabolite biomarkers discovered were selected to build a predictive model that was then used to test the classification accuracy.

EXAMPLE 1

As noted above, hepatocellular carcinoma (HCC) accounts for most cases of liver cancer worldwide, and infection with hepatitis C virus (HCV) is considered a major risk factor for liver cancer even when individuals have not developed clinical cirrhosis. Unbiased global metabolic profiling methods were applied to serum samples from patients with HCC and HCV infection in order to identify metabolite based biomarkers associated with the early stages of liver cancer for improved prognosis.

Serum metabolite profiles from patients with HCC (n=37) and HCV infected patients (n=21) were obtained using high performance liquid chromatography-mass spectrometry (HPLC-MS) methods. Five characteristic metabolites that differed significantly ($p<0.05$) and had sufficient fold change differences (FC<0.7 or FC>1.3) between HCC and HCV infection were identified. A partial least-squares discriminant analysis (PLS-DA) model created using the characteristic metabolites resulted in a good model with 92% sensitivity, 62% specificity, and a receiver operative characteristic curve area (AUROC) of 0.89. The observed means of the integral peak area abundances for each characteristic metabolite showed consistent trends toward higher values for individuals with HCV infection compared to HCC. Two metabolically linked metabolites were observed as well others that have previously been reported as being associated with active liver metabolic perturbations.

Chemicals: HPLC-grade methanol and acetic acid were purchased from Fisher Scientific (Pittsburgh, Pa.). Deionized water was obtained from an EASYpure II UV water purification system (Barnstead International, Dubuque, Iowa).

Serum sample collection and storage: Fasting blood samples from patients with histologically proven HCC (n=37) and HCV infection (n=21) were collected at the Indiana University School of Medicine (Indianapolis, Ind.). Demographic characteristics of the patients are presented in Table 1. Each blood sample was allowed to clot for 45 min and then centrifuged at 2,000 rpm for 10 min. The sera were collected, aliquoted in separate vials, frozen, and shipped over dry ice to Purdue University (West Lafayette, Ind.) where they were stored at −80° C. until use. All samples were collected following the protocol approved by Indiana University School of Medicine and Purdue University Institutional Review Boards. All subjects included in the study were provided written informed consent according to institutional guidelines.

TABLE 1

Summary of clinical and demographic characteristics of the patients studied

| Clinical Diagnosis | HCV Infection | Hepatocellular Carcinoma |
|---|---|---|
| Samples (Patients) | 21 (14 male, 7 female) | 37 (29 male, 8 female) |
| Age, Mean [Range] | 50 (Range 37-71 years old) | 55 (Range 21-72 years old) |

Sample preparation and data acquisition. Frozen serum samples were thawed and proteins were precipitated by adding 200 µL of cold methanol to 100 µL of serum. The mixture was then centrifuged at 14,000 rpm for 10 min after which the supernatant was removed. An additional 200 µL of cold methanol was added to the recovered supernatant and the new mixture was centrifuged at 14,000 rpm for 10 min. The supernatant solution obtained after this second protein removal step was then dried under vacuum and the obtained residue was reconstituted in 7.5 µL methanol and vortexed for 5 sec. An additional 7.5 µL 0.4% acetic acid solution in water was added to bring the total volume to 15 µL which was then vortexed for 5 sec. This final 15 µL solution was again centrifuged at 14000 rpm for 10 min to remove residual particulate matter and the supernatant was transferred to an LC vial for analysis. A separate pooled sample was created by mixing together 3 µL aliquots from 15 serum samples randomly selected from all the sample vials. This pooled sample, referred to as the quality control (QC) matrix sample, was subjected to analysis periodically between every 10 samples. QC sample data also served as technical replicates throughout the data set to assess process reproducibility.

LC-MS analysis was performed using an Agilent LC-QTOF system (Agilent Technologies, Santa Clara, Calif.) consisting of an Agilent 1200 liquid chromatography system coupled online with an Agilent 6520 time-of-flight mass spectrometer. A 3 µL aliquot of reconstituted sample was injected on to a 2.1×50 mm Agilent Zorbax Extend-C18 1.8 µM particle column with a 2.1×30 mm Agilent Zorbax SB-C8 3.5 µm particle guard column, both of which were heated to 60° C. Serum metabolites were gradient-eluted at 0.6 mL/min using mobile phase A: 0.2% acetic acid in water and mobile phase B: 0.2% acetic acid in methanol (2% to 98% B in 13 min, 98% B for 6 min) Electrospray ionization (ESI) was used in positive mode at 3.5 kV with a concurrent 35 psig emitter nebulization pressure. The interface capillary was maintained at 325° C., with a curtain gas flow of 8 L/min Agilent MassHunter Workstation LC-TOF and QTOF Acquisition software (B.02.01) were used for automatic peak detection and mass spectrum deconvolution.

Data analysis. LC-MS data was processed using Agilent's MassHunter Qualitative Analysis software (version B.03.01) for compound identification. A list of ion intensities for each detected peak was generated using a retention time (RT) index and m/z data as the identifiers for each ion. Agilent MassHunter Workstation Mass Profiler Professional software (version B.02.00) was then used for compound peak alignment. A filter was set to remove any metabolite signals that had missing peaks (ion intensity=1) in more than 15% of the samples in any group. Finally, the Agilent Formula Database (Agilent, 2010) was used for compound identification by matching the accurate mass spectrum to a database of metabolite compounds. Unpaired Student's t-test analysis of the data was performed to assess the differences of detected compound intensities between individuals with HCC and patients with HCV infection. Commercially available metabolites with low p-values (<0.05) and significant mean fold changes (FC<0.7 or FC>1.3) for the HCC/HCV ratio were selected as potential biomarker candidates. These metabolite ID's were verified in separate acquisitions using the standard compounds.

Selected biomarker candidates were then filtered to exclude those that had more than 15% missing intensity values (Rel. Ab.=1) within either the HCC or HCV infection groups. Biomarker candidates that were not excluded were then interpolated by having the missing intensity values replaced with the average of the non-trivial abundances within each group. The interpolated MS data of the selected statistically significant metabolites were imported into Matlab (R2008a, Mathworks, Natick, Mass.) installed with a PLS toolbox (version 4.1, Eigenvector Research, Inc., Wenatchee, Wash.) for PLS-DA analyses. The X matrix, consisting of the MS data, was mean centered prior to all statistical analyses. Depending on the group, each subject was assigned a "0" (i.e., HCC) and "1," (i.e., HCV infection) to serve as the (one-dimensional) Y matrix. Leave-one-out cross validation (CV) was chosen, and the number of latent variables (LVs) was selected according to the minimum root mean square error of CV procedure, which in this case was three. Predictions were made visually using a Y-predicted scatter plot with a cut-off value chosen to minimize errors in class membership. The R statistical package (version 2.8.0) was used to generate receiver operating characteristics (ROC) curves, calculate and compare sensitivity, specificity and area under the ROC curve (AUROC).

The LC-MS spectrum for each serum sample consisted of more than 4000 features of which nearly 800 peaks were assigned to metabolites using the Agilent database. Analytes with distinct chromatographic signatures that were missing in more than 15% of the samples from either group were omitted from further analysis. The use of this filter and the Agilent chemical library resulted in a total of 512 identified metabolites most common to both groups. To identify specific metabolites that best correlated with the different disease states the library-identified metabolites were analyzed using univariate analysis. The results, summarized in Table 2, below, showed that 51 metabolites varied significantly (p<0.05) between the two groups and 44 of these compounds had mean fold changes (FC<0.7, FC>1.3) for HCC/HCV infection.

TABLE 2

Identification information for LC-MS metabolites with p-values <0.05.

| | HCC vs HCV Infection | | |
|---|---|---|---|
| Metabolite | p-value[a] | FC[b] | FC[c] |
| Arachidonyl lysolecithin | 2.8E−06 | 2.31 | 0.43 |
| Dioleoylphosphatidylcholine | 1.0E−05 | 1.68 | 0.60 |
| Tazobactam | 9.4E−05 | 1.70 | 0.59 |
| 17beta-Estradiol 17-(beta-D-glucuronide) | 1.3E−04 | 2.40 | 0.42 |
| Verteporfin | 1.4E−04 | 1.55 | 0.64 |
| 3-Deoxyvitamin D3 | 2.2E−04 | 1.61 | 0.62 |
| Myristoyl L-a-lysophosphatidylcholine | 2.6E−04 | 2.34 | 0.43 |
| Tranexamic acid | 3.5E−04 | 1.70 | 0.59 |
| N4-Acetylsulfadoxine | 4.5E−04 | 1.66 | 0.60 |
| 2-Amino-3-methyl-1-butanol | 6.0E−04 | 0.59 | 1.71 |
| Pelletierine | 1.2E−03 | 1.70 | 0.59 |
| Dihydrocelastryl diacetate | 2.2E−03 | 1.57 | 0.64 |
| Tridemorph | 2.9E−03 | 1.37 | 0.73 |
| Uric acid | 3.0E−03 | 0.38 | 2.65 |
| Aceclidine | 3.4E−03 | 1.49 | 0.67 |
| 5,7-nonadienoic acid | 4.6E−03 | 1.46 | 0.69 |
| Fenofibrate | 4.7E−03 | 1.47 | 0.68 |
| 2R-aminohexadecanoic acid | 5.1E−03 | 1.95 | 0.51 |
| 3,4-Dehydrochlorambucil | 5.1E−03 | 1.65 | 0.61 |
| Xanthine | 5.2E−03 | 0.76 | 1.31 |
| dihydroergocristine | 7.1E−03 | 1.30 | 0.77 |
| 5-Hydroxytryptophan | 8.5E−03 | 1.28 | 0.78 |
| Capryloylglycine | 9.0E−03 | 1.36 | 0.73 |
| dodecanamide | 9.4E−03 | 1.26 | 0.79 |
| Indole-3-ethanol + 14.2 min | 1.2E−02 | 1.46 | 0.68 |
| 8-Amino-7-oxononanoate | 1.2E−02 | 1.48 | 0.68 |
| Ceramide (d18:1/22:0) | 1.3E−02 | 1.83 | 0.55 |
| N-methyl-Gabapentin | 1.3E−02 | 1.36 | 0.74 |
| Cholylglycine | 1.3E−02 | 0.40 | 2.47 |
| 3-O-Methyl-L-DOPA | 1.3E−02 | 0.69 | 1.46 |
| Enalapril | 1.4E−02 | 0.87 | 1.15 |
| 15-hydroxy-heneicosanoic acid | 1.4E−02 | 1.47 | 0.68 |
| Linolenoyl lysolecithin | 1.6E−02 | 1.54 | 0.65 |
| 8-Amino-7-oxononanoate | 1.6E−02 | 1.51 | 0.66 |
| 5-Hydroxytryptophan | 1.8E−02 | 0.60 | 1.68 |
| N-Lignoceroylsphingosine | 1.9E−02 | 2.74 | 0.36 |
| 1,2-Dipalmitoylphosphatidylcholine | 1.9E−02 | 1.43 | 0.70 |
| (9R,13R)-1a,1b-dihomo-jasmonic acid | 2.0E−02 | 1.24 | 0.81 |
| D-Leucic acid | 2.2E−02 | 0.70 | 1.42 |
| Glycolaldehyde | 2.3E−02 | 0.72 | 1.38 |
| 1-Methylguanine | 2.5E−02 | 0.67 | 1.49 |
| Maltose | 2.7E−02 | 0.53 | 1.88 |
| 3-Hydroxycapric acid | 3.1E−02 | 0.70 | 1.44 |
| Tricosanedioic acid | 3.2E−02 | 1.13 | 0.89 |
| Netilmicin | 3.3E−02 | 0.71 | 1.40 |
| Dacarbazine | 3.3E−02 | 0.64 | 1.56 |
| Cytosine | 3.4E−02 | 0.80 | 1.25 |
| 7-hydroxy-5-heptynoic acid | 3.6E−02 | 0.82 | 1.21 |
| Linoleamide | 3.8E−02 | 0.82 | 0.55 |
| Pyridoxine (Vitamin B6) | 4.2E−02 | 1.45 | 0.69 |
| Indole-3-ethanol + 12.4 min | 4.8E−02 | 1.38 | 0.72 |

[a]p-value determined from Student's t-test, only p-values <0.05 are displayed;
[b]FC: fold change between HCC and HCV;
[c]FC: fold change between HCV and HCC.

Commercially available metabolites that had previously been reported as relevant to liver diseases by other researchers utilizing methods other than LC-MS by as well as an observed m/z with an accuracy of 1 ppm or less against the Agilent database were chosen as characteristic metabolites. Table 3, below, summarizes the list of the five characteristic metabolites and reports their observed m/z values, database delta m/z values, retention times, p-values, and fold changes. Box and whisker plots of the integral peak areas for each characteristic metabolite are shown in FIG. 1A to FIG. 1E, and illustrate the systematic decrease in observed values for HCC patients compared to individuals with HCV.

TABLE 3

Identification information for characteristic LC-MS metabolites.

| Compound | Calculated m/z (Da) | Detected m/z (Da) | Delta m/z (ppm) | RT Detected (min) | p-Value | Fold Change |
|---|---|---|---|---|---|---|
| Uric Acid | 168.028 | 168.028 | 0.000 | 0.55 | 0.00300 | 2.65 |
| Cholyglycine | 465.309 | 465.309 | 0.000 | 9.90 | 0.01323 | 2.47 |
| 3-Hydroxycapric acid* | 188.141 | 188.142 | 0.001 | 8.90 | 0.03108 | 1.44 |
| D-Leucic acid* | 132.079 | 132.079 | 0.000 | 0.75 | 0.02248 | 1.42 |
| Xanthine | 152.033 | 152.033 | 0.000 | 0.65 | 0.00522 | 1.31 |

*Na adduct corrected

Figure 2A:
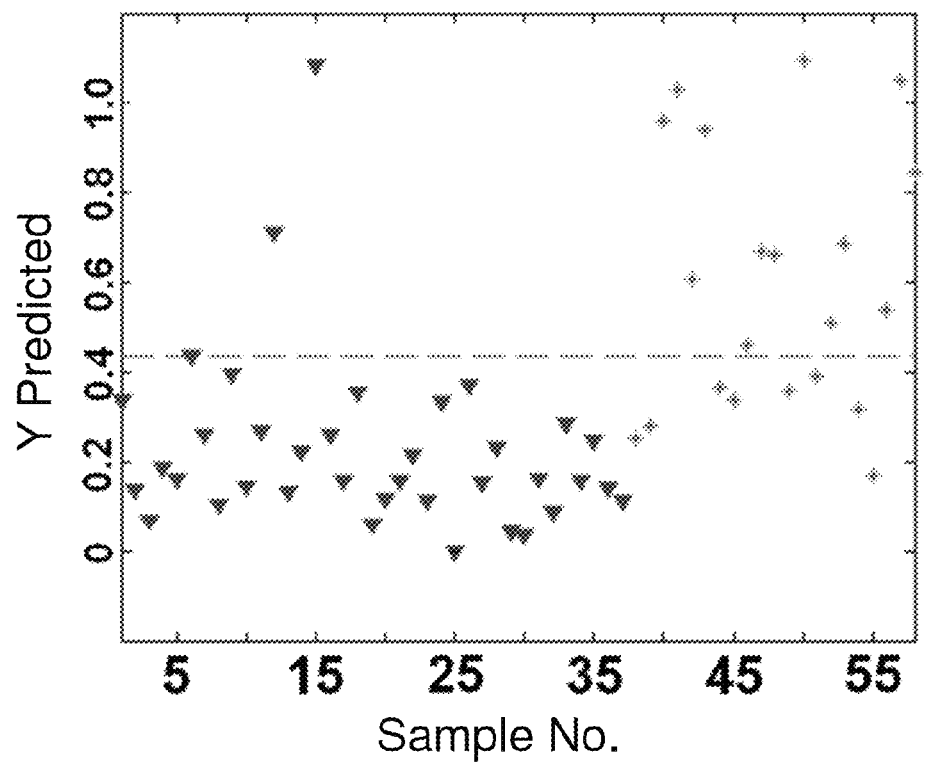
FIG. 2A and FIG. 2B show the results of metabolic profile analysis of characteristic metabolite biomarkers detected by LC-MS for PLS-DA model discrimination of individuals with HCC or HCV infection.
Figure 2B:
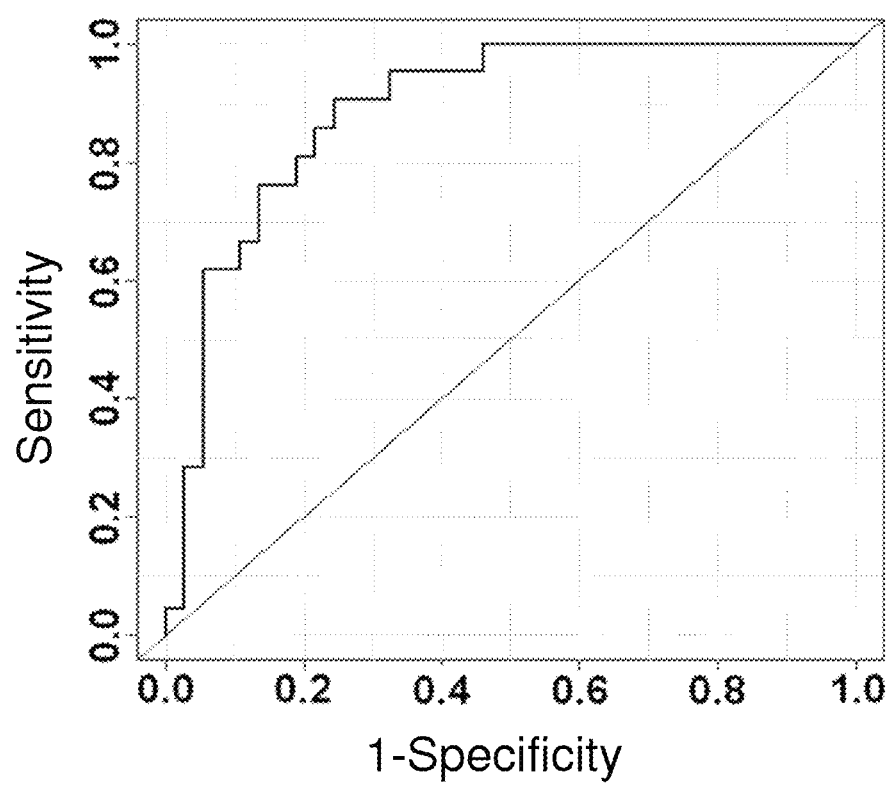

A PLS-DA model was built using the five characteristic metabolite integral peak area intensities to test the classification accuracy for the two patient groups, and the results are as shown in FIG. 2A and FIG. 2B. The model derived by the LC-MS detected metabolites provided a sensitivity and specificity of 92% and 62%, respectively, with a calculated AUROC of 0.89. Levels of the metabolites between HCC patients compared to individuals with HCV infection were compared using box-and-whisker plots. All characteristic metabolites showed that levels were elevated in individuals with HCV infection and were lower for those diagnosed with HCC.

This study was focused on identifying characteristic metabolites for the establishment of improved clinical biomarkers for HCC and insights into the altered metabolism in HCC compared to HCV infected patients. There were 44 metabolites with low p-values and significant fold changes. Five of these metabolite compounds were chosen as biomarker candidates due to their previously established correlations to impaired liver function. Comparison of the individual metabolites between the two patient groups showed clear differences as shown in FIG. 1A to FIG. 1E, with all five characteristic metabolites being decreased in individuals with HCC. The good discrimination between HCC and HCV infection based on the PLS-DA model that uses these specific metabolites indicate that LC-MS methodology can identify the early onset of liver cancer in HCV infection patients that might not be detectable by MRI or other risk management practices currently available.

Two of the five characteristic metabolites, uric acid and xanthine, are linked metabolically and are both involved in the purine degradation pathway. Xanthine is formed from guanine by guanine deaminase, hypoxanthine by xanthine oxidoreductase, or xanthosine by purine nucleoside phosphorylase (PNP). Uric acid is subsequently formed from xanthine by xanthine oxidase which plays an important role in human purine catabolism. Purine metabolism has already been shown to be altered in chemically induced transplantable hematomas in rats and that xanthine oxidoreductase activity decreases in individuals with cancer. The lower levels of both these purine pathway metabolites in HCC fit previous observations of reduced xanthine oxidoreductase activity. The presence of two metabolically linked metabolites that have a strong positive affiliation between the two patient groups supports the hypothesis that it is possible to monitor the perturbed metabolism of liver cancer via LC-MS.

The appearance of cholylglycine and 3-hydroxycapric acid have previously been used to gauge liver dysfunction from serum levels employing non-LC-MS techniques. Liver fatty acid oxidation performance can in part also be gauged by the output of the 3-hydroxy dicarboxylic acid family. In this case, the overproduction of both of these metabolites in the HCV infection patients may indicate that sustained accelerated metabolism in hepatic cells for long periods of time places individuals at risk for developing HCC. Comparing levels of these metabolites in a group of healthy individuals in future studies would be informative. This would address the question of whether HCV infection increases metabolism from the normal state and these increased levels only return to normal values after hepatic cells can no longer sustain that level of output after the onset of HCC.

There is less established evidence in the literature that directly links D-leucic acid with liver dysfunction. A complex relationship has been shown between mTOR ("mammalian target of rapamycin," an atypical serine/threonine kinase) activity and cancer, and that leucine or a leucine derivative maybe be involved in mTOR activity. D-leucic acid is also related to more general cellular mechanisms of cancer and the addition of this metabolite when creating a PLS-DA model increased the AUROC significantly, which was a primary driver for its retention.

The PLS-DA model built using the characteristic metabolite integral peak area intensities provided a sensitivity and specificity of 92% and 62% respectively, with a calculated AUROC of 0.89. This model was reasonably effective in identifying individuals with HCC however, the relatively high misclassification of individuals with HCV infection has two possible interpretations. Either these markers are not strong candidates to discriminate early onset HCC in individuals with HCV or these markers are so effective at discrimination that they are indicating which patients in the HCV group have developed early stage HCC, such as micro metastases. Collection of time-based serum samples from HCV patients where it is known which patients later developed HCC would address the apparent high false positive rate.

The results have shown that the metabolic profiling of serum using LC-MS along with multivariate statistical methods can provide a detailed picture of metabolic changes in HCC compared with HCV infection. HCC patients can quite easily be separated from patients inflected with HCV.

EXAMPLE 2

In this Example, we focus on identifying additional metabolic changes and altered metabolic pathways between HCC patients with underlying HCV and HCV patients who are at high risk of developing HCC. To extend the coverage of low concentration metabolites that distinguish HCV and HCC, we have chosen a targeted method based on LC-MS/MS metabolite profiling of serum. This multiplexed targeted LC-MS/MS approach has been shown to be quite robust and versatile in a variety of biomarker and systems biology studies. In this study, a number of significant changes were observed in several important and cancer related metabolic pathways. Utilizing multivariate statistical analysis we could combine the top performing metabolite biomarkers into a model that distinguishes between the two patient groups with excellent performance. Monitoring metabolites in HCV patients may provide improved understanding of the timing and pathogenesis of HCC, and when further developed allow identification HCV patients who are at high risk of liver cancer at an earlier stage.

Metabolic profiling of high risk and HCC patients was performed to better understand altered metabolic pathways and provide insights into the process of carcinogenesis. In this study 73 blood metabolites from HCC patients (N=30) and HCV infected patients (n=22) were measured using liquid chromatography resolved tandem mass spectrometry (LC-MS/MS). Protocols were first developed using 47 metabolites in positive MRM (multiple reaction monitoring) ion mode and 51 in negative MRM ion mode using standard compounds to optimize separation and fragmentation. Using this protocol, 73 serum metabolites were measured reliably in serum from HCV and HCC patients. Analysis of the data showed that while levels of a majority of the metabolites were similar in both HCC and HCV, 16 metabolites differed significantly between the two groups ($p \leq 0.05$). A partial least squares discriminant analysis (PLS-DA) model was developed using the 16 distinguishing biomarker candidates with leave-one-out cross-validation. The model distinguished the two groups with a sensitivity of 90% and specificity of 93%, and an area under the receiver operating characteristic curve (AUROC) of 0.96. Altered metabolic pathways including amino acid, fatty acid, purine and nucleotide metabolism could be identified based on the 16 significant metabolite biomarkers. These results can provide an improved method for identifying HCC patients within the at risk HCV infected population, and provide insights into the altered metabolic pathways between hepatocellular carcinoma and its related high risk liver disease.

Chemicals and reagents. Methanol (HPLC-grade) was obtained from Avantor Performance Materials (PA). Acetic acid ($\geq 99.7\%$) and standard metabolites (minimal 98% purity), were purchased from Sigma-Aldrich (St. Louis, Mo.). L-Proline-$^{13}C_5$, $^{15}N_1$ (97-99 atom % $^{13}C$, 97-99 atom % $^{15}N$) was purchased from Cambridge Isotope Laboratories (Andover, Mass.). High purity water was obtained from an EASYpure II UV water purification system (Barnstead International, Dubuque, Iowa).

Patients and Serum Samples. Patient serum samples were collected from the Indiana University/Lilly tissue bank through clinical collaboration following protocols approved by the Institutional Review Boards of both Indiana and Purdue Universities. Sample cohorts consisted of histologically proven HCC patients with underlying HCV (n=30; mean age 55.5±10.7) and HCV patients without HCC (n=22; mean age 52.2±8.1). Table 4, below, summarizes the demographic characteristics of the patient cohorts. Overnight fasted samples were collected to minimize confounding factors arising from diet. The blood samples were allowed to clot for 45 min; centrifuged at 2000 rpm for 10 min and the resulting sera were separated and aliquoted into separate tubes and frozen immediately at −70° C. The frozen samples were then shipped over dry ice to Purdue University (West Lafayette, Ind.), which were stored at −80° C. freezer until used for analysis.

TABLE 4

Demographic and Clinical Characteristics of the Patients

| | HCC | HCV |
| --- | --- | --- |
| Number of patients | 30 | 22 |
| Age (mean ± SD) | 54.5 ± 10.7 | 52.2 ± 8.1 |
| Gender (F/M) | 0.3 | 0.46 |
| Caucasian | 21 | 20 |
| African American | 1 | 2 |
| Hispanic | 3 | 0 |
| Unknown race/ethnicity | 4 | 0 |
| Middle Eastern | 1 | 0 |

Sample preparation and acquisition. Frozen patient sera were thawed at room temperature for 30 min Protein precipitation was performed by adding 600 μL methanol to 200 μL to each serum sample. The solution was vortexed vigorously for 1 min and then held for 20 min at −20° C. The samples were centrifuged at 14,000 rpm for 20 min (Eppendorf centrifuge, model 5804, Hauppauge, N.Y.), and the supernatant was collected and dried using a vacuum system (Vacufuge Plus, Eppendorf, Hauppauge, N.Y.). Each dried sample was reconstituted in 50 μL water/methanol (95:5) and then transferred to an LC sample vial. Labeled sample vials were placed in the autosampler in random order and kept at −4° C. throughout the analysis. A 10 μL sample injection was used for LC-MS/MS analysis in both positive and negative modes. $^{13}C_5$-$^{15}N$-proline was used as an internal reference. Further, to assess performance of the instrument and process reproducibility, a mixture of all the metabolites was used as a quality control sample and injected into the LC-MS/MS after every 25 patient samples, as well as before and after cleaning the ESI source; the ESI source was cleaned every 48 hrs. Duplicate sample runs were performed to account for technical reproducibility.

To evaluate sensitivity and linear dynamic ranges, we determined limits of detection (LODs) and dynamic ranges from a mixture of 39 standard metabolites at 20 different concentrations Table 5, below, summarizes those results.

LC-MS/MS system components and MS parameters. Mass spectrometric analyses were performed on an ABI Sciex API-3000 triple quadrupole mass spectrometer (AB SCIEX, Framingham, Mass.) equipped with an ESI turbo ion spray source operated in both positive and negative ion modes. The mass spectrometer was coupled to an Agilent 1100 series HPLC system consisting of two quaternary pumps, solvent degassers and a temperature-controlled column oven. A CTC PAL autosampler (LEAP Technologies, Carrboro, N.C.) equipped with multiple injection ports was used for sample loading, while a VICI 2-position switching valve (Valco Instruments, Houston, Tex.) allowed the MS inlet to be switched between the two pumps, one of which was used for separating metabolites detected as positive ions and the other as negative ions. The two pumps allowed for alternating separation and column reconditioning to increase throughput. Multiple reaction monitoring (MRM) mode was used to detect the multiple metabolites as they eluted off of the chromatographic column using a dwell time of 100 ms per metabolite. Nitrogen gas was used as curtain, collision, and nebulizer gas, with flow rates set at 12, 10, 12 (arbitrary units), respectively. The ion spray needle voltages used for MRM positive and negative modes were set at 3600 V and −3600 V, respectively. The LC-MS/MS system was controlled by Analyst 1.5 software (AB SCIEX, Framingham, Mass., USA).

Chromatography Conditions. Chromatography was performed under reverse phase conditions using an Eclipse XDB-C18 4.6×150, 5 μm column (Agilent Technologies, Santa Clara, Calif.). The flow rate, column temperature and sample injection volume were set to 400 μL/min, 45° C., and 10 μL, respectively. The optimized chromatography conditions were as follows: Solvent A: water with 0.1% acetic acid; Solvent B: methanol with 0.1% acetic acid. The elution gradient, 0 min: 5% B; 42 min: 95% B, was used to separate metabolites detected in negative MRM mode. For positive MRM mode, 0 min: 5% B; 35 min: 95% B were used. Before all injections, column cleaning and equilibration steps were applied.

TABLE 5

Limits Of Detection (LODs) And Dynamic Ranges Derived Using Standard Metabolite Mixtures

| | Metabolites | limits of detection (LODs)* (μM) | The linear dynamic range (μM) | (μM) | $R^2$ |
|---|---|---|---|---|---|
| 1 | Aconitic acid | 4.73E+00 | 1.56E−01 | 5.17E+01 | 0.98 |
| 2 | Alpha-Ketoglutarate | 1.70E+00 | 2.50E−04 | 2.63E+01 | 1.00 |
| 3 | Arginine | 1.56E+00 | 2.49E−04 | 6.23E−01 | 0.97 |
| 4 | Asparagine | 3.13E−02 | 2.50E−04 | 4.90E+00 | 0.98 |
| 5 | Azelaic acid | 1.07E−04 | 2.50E−04 | 3.69E+01 | 0.99 |
| 6 | Betaine | 1.25E−03 | 2.49E−04 | 3.49E+00 | 0.98 |
| 7 | Biotin | 2.50E−04 | 2.49E−04 | 1.88E+01 | 0.98 |
| 8 | Creatine | 2.51E−04 | 2.51E−04 | 3.70E+01 | 0.97 |
| 9 | Dopamine | 2.50E+00 | 2.50E−04 | 9.59E+00 | 0.99 |
| 10 | Fumaric acid | 2.75E−02 | 6.21E−02 | 5.23E+01 | 0.97 |
| 11 | Glutamic acid | 6.22E−03 | 1.24E+00 | 3.67E+01 | 0.98 |
| 12 | Glutaric acid | 2.75E−02 | 3.12E−02 | 2.63E+01 | 0.99 |
| 13 | Hippuric acid | 2.15E−04 | 2.50E−04 | 2.64E+01 | 0.99 |
| 14 | Homocysteine | 1.56E−01 | 6.24E−03 | 4.89E+00 | 0.98 |
| 15 | Hydroxy-L-Proline | 6.25E−01 | 2.50E−04 | 1.88E+01 | 0.99 |
| 16 | Hypoxanthine | 3.49E+00 | 6.24E−03 | 1.34E+01 | 0.99 |
| 17 | 3 Hydroxybutyric acid | 1.07E−04 | 2.50E−04 | 2.63E+01 | 1.00 |
| 18 | 4-Hydroxybenzoic acid | 5.00E−02 | 2.50E−04 | 1.88E+01 | 0.99 |
| 19 | 4-hydroxyphenylpyruvic acid | 1.70E+00 | 2.49E−04 | 5.14E+01 | 1 |
| 20 | 4-Pyridoxic acid | 1.72E−03 | 2.50E−04 | 1.88E+01 | 0.96 |
| 21 | Inosine | 3.12E−02 | 2.49E−04 | 4.88E+00 | 0.98 |
| 22 | Kynurenine | 2.70E−02 | 2.49E−04 | 2.62E+01 | 0.99 |
| 23 | Lactic acid | 2.40E+00 | 2.49E−04 | 5.15E+01 | 0.98 |
| 24 | Leucine | 4.98E−05 | 2.49E−04 | 1.88E+01 | 0.99 |
| 25 | Isoleucine | 1.56E−01 | 2.49E−04 | 3.67E+01 | 0.99 |
| 26 | Methionine | 1.56E−01 | 3.12E−02 | 1.88E+01 | 0.99 |
| 27 | Phenylalanine | 5.01E−05 | 1.25E−03 | 1.88E+01 | 0.99 |
| 28 | Malic acid | 1.70E+00 | 2.46E−04 | 5.08E+01 | 0.99 |
| 29 | Malonic acid | 1.07E−04 | 3.13E−02 | 2.64E+01 | 1.00 |
| 30 | Orotic acid | 1.72E+00 | 2.50E−04 | 5.16E+01 | 0.98 |
| 31 | Pantothenic acid | 3.40E−03 | 2.50E−04 | 2.63E+01 | 0.99 |
| 32 | Phenylalanine | 1.56E−01 | 1.25E−03 | 5.17E+01 | 0.99 |
| 33 | Proline | 5.00E−05 | 2.50E−04 | 1.88E+01 | 0.98 |
| 34 | Succinic acid | 1.07E−04 | 2.50E−04 | 2.64E+01 | 0.99 |
| 35 | Tryptophan | 6.83E−05 | 2.49E−04 | 3.67E+01 | 1.00 |
| 36 | Tyrosine | 2.33E−02 | 1.86E−04 | 1.40E+01 | 0.99 |
| 37 | Uridine | 1.56E−01 | 2.50E−04 | 4.89E+00 | 0.98 |
| 38 | Valine | 1.54E−01 | 2.50E−04 | 1.88E+01 | 1.00 |
| 39 | Xanthine | 2.00E−02 | 6.23E−03 | 1.88E+01 | 0.97 |

Limit of detection (LOD) was assessed based on S/N = 3

Chromatography Conditions. Chromatography was performed under reverse phase conditions using an Eclipse XDB-C18 4.6×150, 5 μm column (Agilent Technologies, Santa Clara, Calif.). The flow rate, column temperature and sample injection volume were set to 400 μL/min, 45° C., and 10 μL, respectively. The optimized chromatography conditions were as follows: Solvent A: water with 0.1% acetic acid; Solvent B: methanol with 0.1% acetic acid. The elution gradient, 0 min: 5% B; 42 min: 95% B, was used to separate metabolites detected in negative MRM mode. For positive MRM mode, 0 min: 5% B; 35 min: 95% B were used. Before all injections, column cleaning and equilibration steps were applied.

Compound Optimization Parameters. Information about each precursor ion m/z values (Q1) and product ion m/z values (Q3)□for MRM detection of the metabolites was obtained from previous studies. To decrease the chemical background noise and increase the intensity of metabolite peaks, pre-collision cell voltages including declustering potential (DP), focusing potential (FP), collision energy (CE), and collision cell exit potential (CXP) parameters for each metabolite were optimized. To this end, a 2 μM solution for each metabolite in 50:50 water:methanol was prepared and was directly infused into the mass spectrometer using a Harvard PHD 2000 Syringe Pump (Holliston, Mass.) at a flow rate of 15 μL/min. The optimized metabolite parameters were obtained and used for the appropriate MRM mode.

Data analysis. Peak intensities for the 73 measured metabolites were integrated using Analyst 1.5 software (AB SCIEX, Framingham, Mass.). Peak integrals for each metabolite averaged over duplicate sample runs were used for further analysis. The Student's t-test was used to evaluate statistical significance for metabolite intensity differences between HCC and HCV samples. Four metabolites that showed the lowest p-values between the two patient groups were then chosen for multivariate statistical analysis using partial least-squares discriminate analysis (PLS-DA). PLS-DA modeling was performed using Matlab (R2008a, Mathworks, Natick, Mass.) installed with the PLS toolbox (v4.1, Eigenvector Research, Wenatchee, Wash.). The X matrix, consisting of the MS data, was mean centered prior to all statistical analyses. Each subject was assigned either a "0" (for HCC) or "1" (for HCV) to serve as inputs to the one dimensional Y matrix. Leave-one-out cross validation (CV) was chosen, and the number of latent variables (3 in this case) was selected according to the minimum root mean square error of CV procedure. Class predictions were made visually using a Y-predicted scatter plot with a cut-off value chosen to minimize errors in class membership. The R statistical package (version 2.8.0) was used to generate receiver operator characteristic (ROC) curves and box-and-whisker plots, calculate sensitivity, specificity and area under the ROC curve (AUROC).

Figure 5:
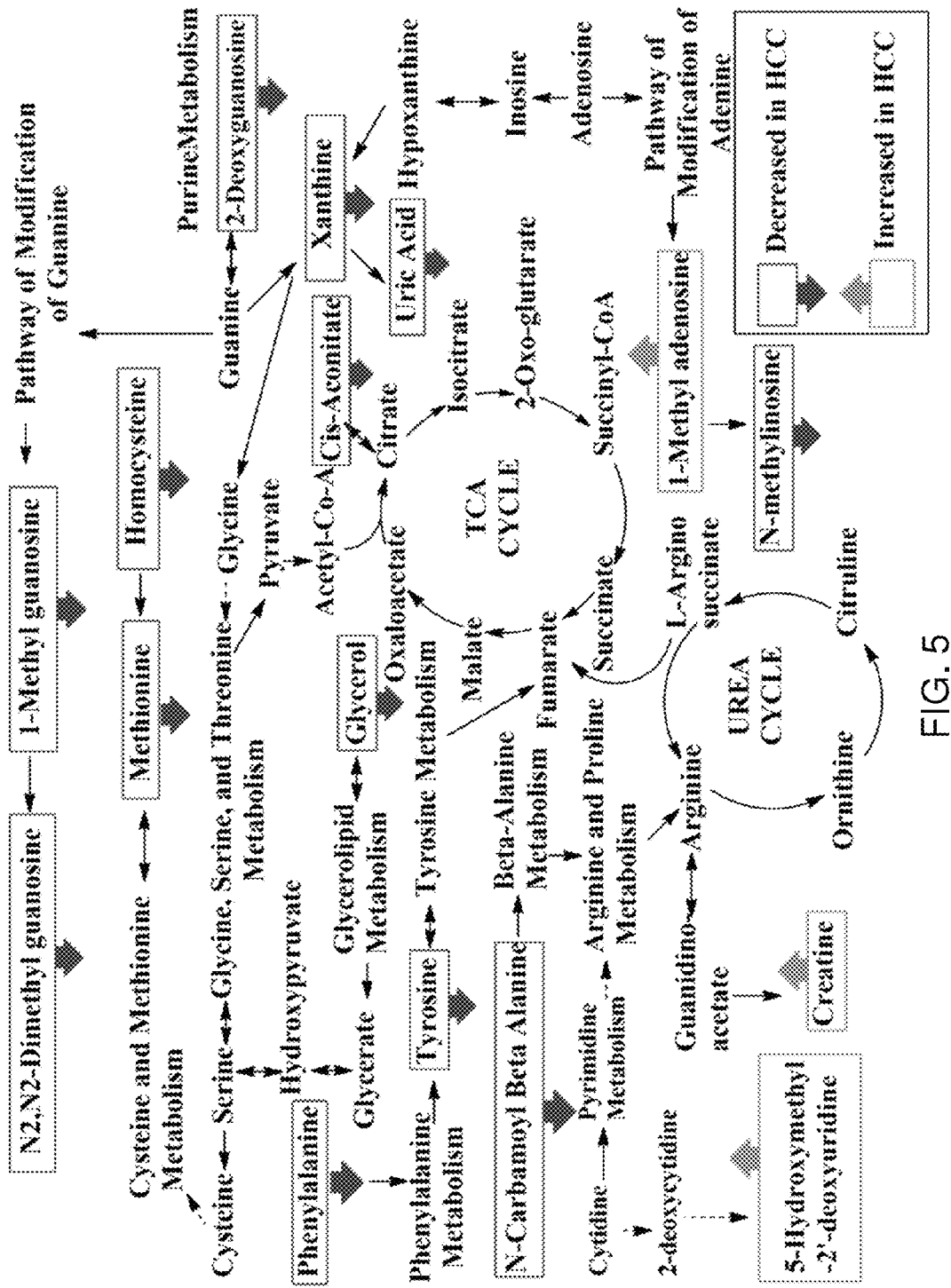
FIG. 5 shows diagrammatically the metabolism pathways for the biomarkers, with the 16 metabolite biomarkers indicated by a rectangular frame.

A schematic diagram of altered metabolic pathways was drawn based on established databases [www.genoe.jp; http://modomics.genesilico.pl/pathways/] to help understand the pathogenesis of the disease and indicate the relationship among the candidate biomarkers, and is shown in FIG. 5.

The data were also analyzed by selecting four metabolites based on variable importance in projection (VIP) scores derived using all 73 metabolites for comparison with the results obtained using 4 lowest p-value metabolites.

Mass spectrometric analyses were performed on a Sciex API-3000 triple quadrupole mass spectrometer equipped with a Turbo IonSpray source, ESI (Applied Biosystems, Carlsbad, Calif.) operated in the positive and negative ion modes and using multiple reaction monitoring (MRM). The mass spectrometer was coupled to two 1100 series Agilent LC systems, which consisted of a quaternary pump, a degasser (Agilent Technologies, Santa Clara, Calif.), a CTC PAL autosampler (LEAP Technologies, Carrboro, N.C.), temperature-controlled column oven (Agilent Technologies), and VICI 2-position switching valve (Valco Instruments, Houston, Tex.). This LC/MS/MS system was controlled by Analyst 1.5 software (Applied Biosystems-SCIEX). Nitrogen was used as an auxiliary gas with a flow rate 8.0 L/min Turbo gas temperature was set at 450° C. The ion spray needle voltage used in the MRM positive and negative modes was set at 3600 and −3600V, respectively. Nebulizer, curtain and collision gas pressures were set to 12 psi, 12 psi, 10 psi, respectively.

Targeted analysis using LC-MS/MS in MRM mode was performed on 73 metabolites that could be detected reliably in serum. Of these, 38 metabolites were detected in negative ion mode and 35 metabolites in positive ion mode. All 73 metabolites were detected in all HCC and HCV patient samples and could be measured quantitatively and reliably based on the achieved MS sensitivity, chromatographic conditions and good instrumental stability as observed from the CV of 13-20% for quality control samples. Table 6, below, provides an overview of the classes of compounds that were represented in the set of 73 metabolites that were detected.

Table 7, below, lists the metabolites, and provides the p-values of a comparison using Student's t test of the concentration in samples from HCC patients and from HCV patients.

TABLE 7

List of metabolites detected in positive and negative MRM modes

| Metabolites identified in the positive mode | p-value | # | Metabolites identified in the negative mode | p-value |
|---|---|---|---|---|
| Adenine | 0.62 | 1 | Aconitic acid | 0.029 |
| Allantoin | 0.16 | 2 | Adipic acid | 0.65 |
| Arginine | 0.16 | 3 | Allantoic acid | 0.37 |
| Argininosuccinic acid | 0.26 | 4 | Alpha-ketoglutaric acid | 0.76 |
| Asparagine | 0.14 | 5 | Ascorbic acid | 0.18 |
| Betaine | 0.45 | 6 | Azelaic acid | 0.28 |
| Choline | 0.87 | 7 | 2-Aminoadipic acid | 0.33 |
| Creatine | 0.029 | 8 | Biotin | 0.83 |
| Dimethylglycine | 0.1 | 9 | Citrulline | 0.21 |
| 2-Deoxyguanosine | 0.015 | 10 | 2-Dehydro-D-gluconic acid | 0.046 |
| Dopamine | 0.32 | 11 | Deoxythymidine 5-monophosphate | 0.4 |
| Glutamic acid | 0.4 | 12 | Fumaric acid | 0.73 |
| Glycerol | 0.018 | 13 | Glutaric acid | 0.06 |
| Guanidinoacetic acid | 0.69 | 14 | Glycocholic acid | 0.085 |
| Homocysteine | 0.036 | 15 | Hippuric acid | 0.16 |
| Hydroxy-L-proline | 0.68 | 16 | Homovanillic acid | 0.74 |
| 3-Hydroxyanthranilic acid | 0.47 | 17 | 3-Hydroxybutyric acid | 0.35 |
| 5-Hydroxymethyl-2'-deoxyuridine | 0.00088 | 18 | 3-Hydroxy-2-methylbutanoic acid | 0.24 |
| Inosine | 0.49 | 19 | 4-hydroxy phenylpyruvic acid | 0.4 |
| Isoleucine | 0.085 | 20 | 4-Hydroxybenzoic acid | 0.15 |
| Leucine | 0.35 | 21 | Hypoxanthine | 0.72 |
| Methionine | 0.0032 | 22 | Kynurenine | 0.11 |
| 1-Methyladenosine | 0.011 | 23 | Lactic acid | 0.17 |
| 1-Methylguanosine | 0.0078 | 24 | Maleic acid | 0.48 |
| 1-Methylinosine | 0.0075 | 25 | Malic acid | 0.39 |
| N-Alpha-acetylornithine | 0.1 | 26 | Malonic acid | 0.32 |
| N-Carbamoyl-beta alanine | 0.016 | 27 | N-Acetyl glycine | 0.87 |
| $N^2,N^2$-Dimethylguanosine | 0.0018 | 28 | Orotic acid | 0.74 |
| Phenylalanine | 0.013 | 29 | Orotidine-5-monophoshate | 0.56 |
| Proline | 0.2 | 30 | Oxaloacetic acid | 0.26 |
| Tryptophan | 0.36 | 31 | p-Aminobenzoic acid | 0.24 |
| Tyrosine | 0.016 | 32 | Pantothenic acid | 0.58 |
| Uridine | 0.1 | 33 | 4-pyridoxic acid | 0.45 |
| Valine | 0.91 | 34 | Quinolinic acid | 0.4 |
| Xanthine | 0.011 | 35 | Suberic acid | 0.098 |
| | | 36 | Succinic acid | 0.29 |
| | | 37 | Uric acid | 0.0069 |
| | | 38 | Xanthurenic acid | 0.92 |

TABLE 6

Molecular class assignments for the 73 metabolites detected by LC-MS/MS.

| Class[a] | Number | Percentage |
|---|---|---|
| Amino acids | 26 | 36 |
| Organic acids | 22 | 30 |
| Nucleosides and nucleotides | 9 | 12 |
| Purines and its derivatives | 5 | 7 |
| Amino ketones | 3 | 4 |
| Others | 8 | 11 |

Ref.: Wishart, D. S., et al (2007, 2009, 2013), www.hmdb.ca

Figure 3A:
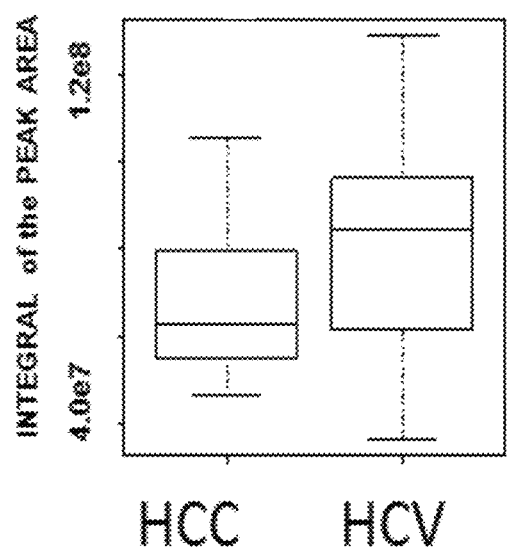
FIG. 3A-FIG. 3P show box-and-whisker plots comparing the groups "HCC" and "HCV" for several biomarkers, in which the y axis for each plot indicates integral of the peak area for that compound.
Figure 3B:
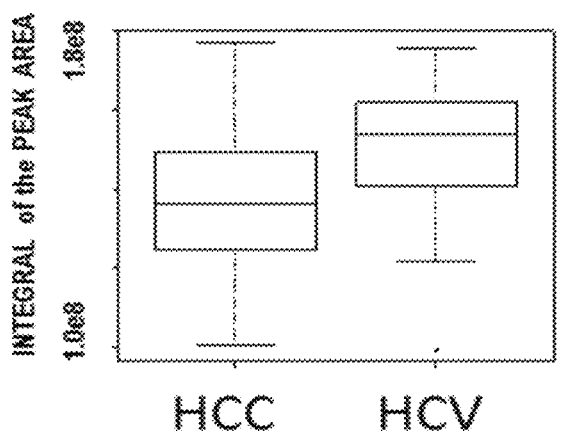
FIG. 3B, phenylalanine.
Figure 3C:
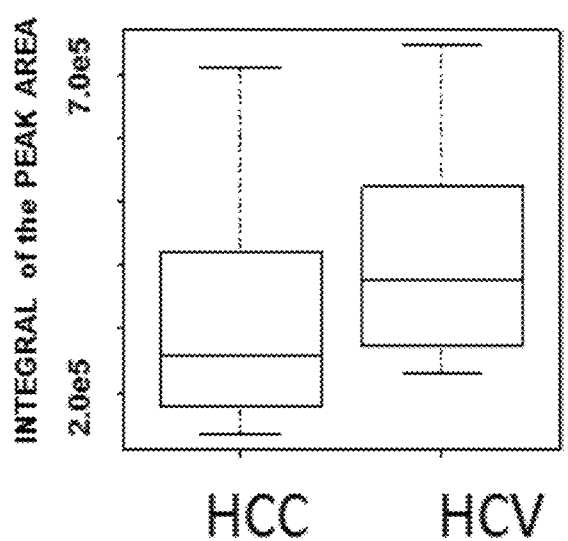
FIG. 3C, glycerol.
Figure 3D:
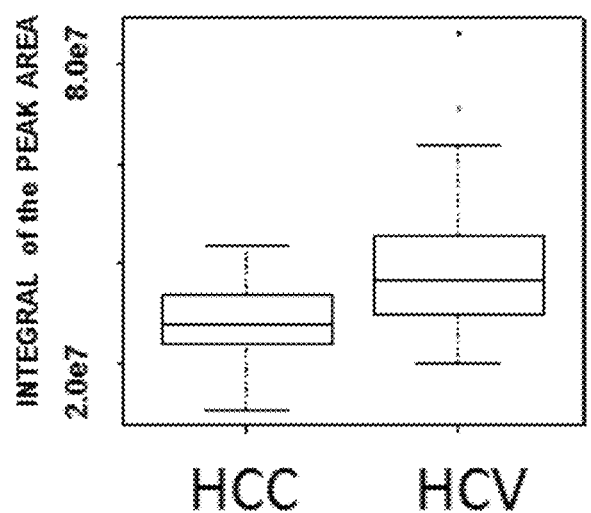
FIG. 3D, methionine.
Figure 3E:
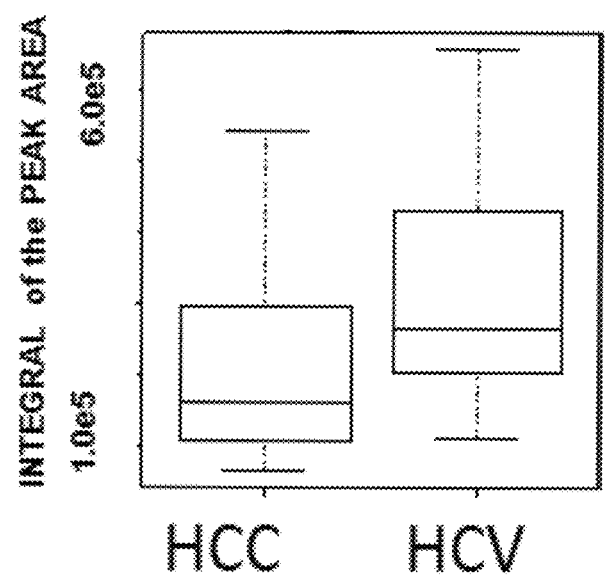
Figure 3F:
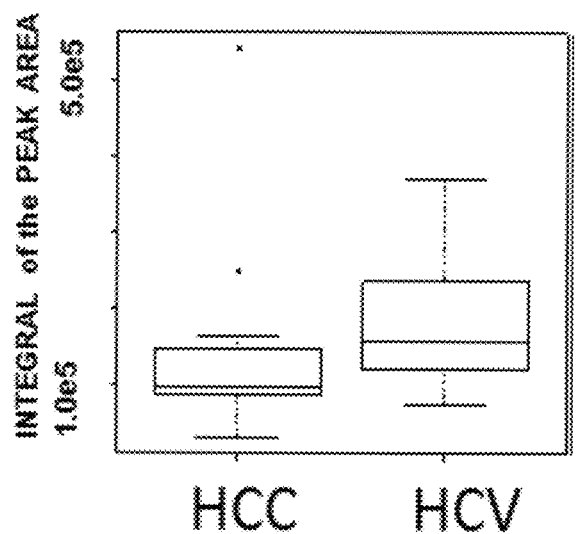
FIG. 3F, N-carbamoyl-beta-alanine.
Figure 3G:
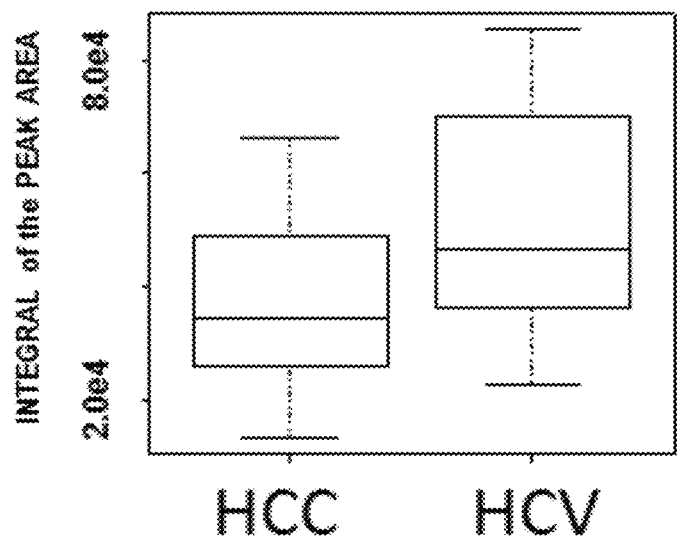
FIG. 3G, xanthine.
Figure 3H:
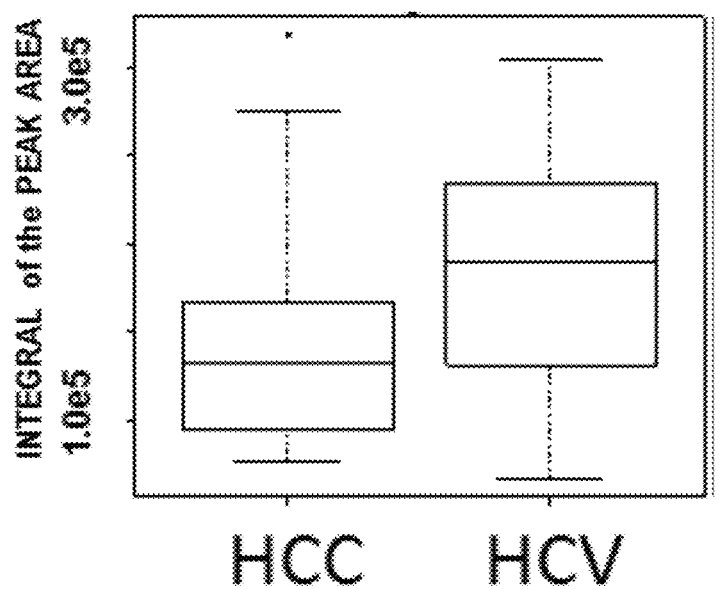
FIG. 3H, homocysteine.
Figure 3I:
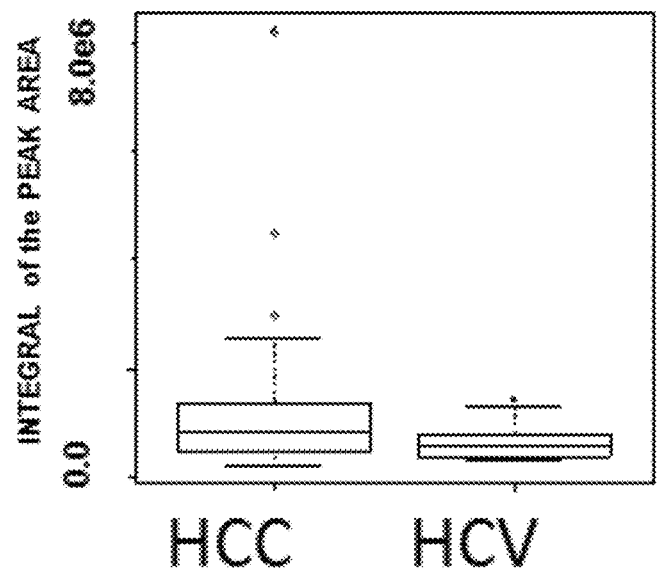
FIG. 3I, creatine.
Figure 3J:
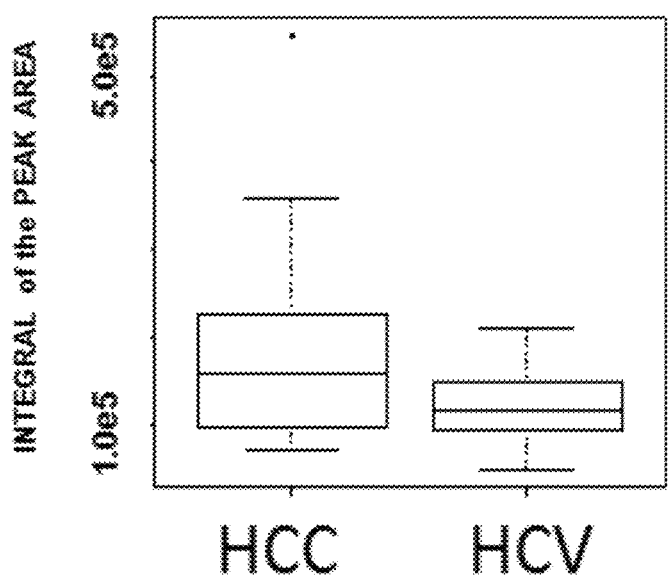
Figure 3K:
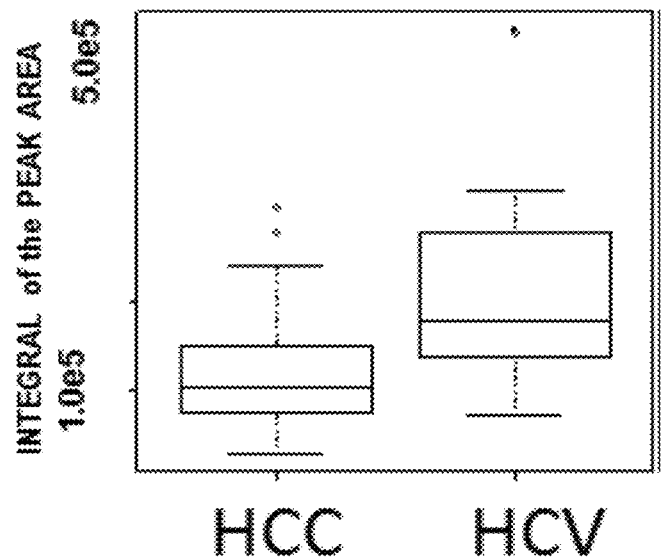
FIG. 3K, $N^2,N^2$-dimethylguanosine.
Figure 3L:
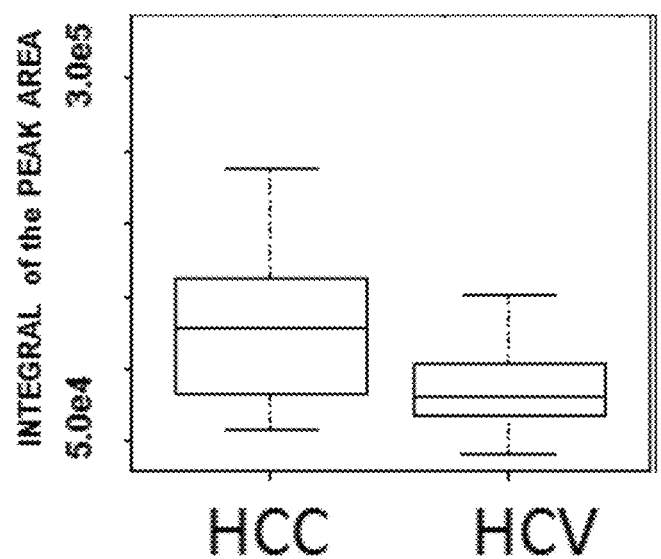
FIG. 3L, hydroxymethyl-2'-deoxyuridine.
Figure 3M:
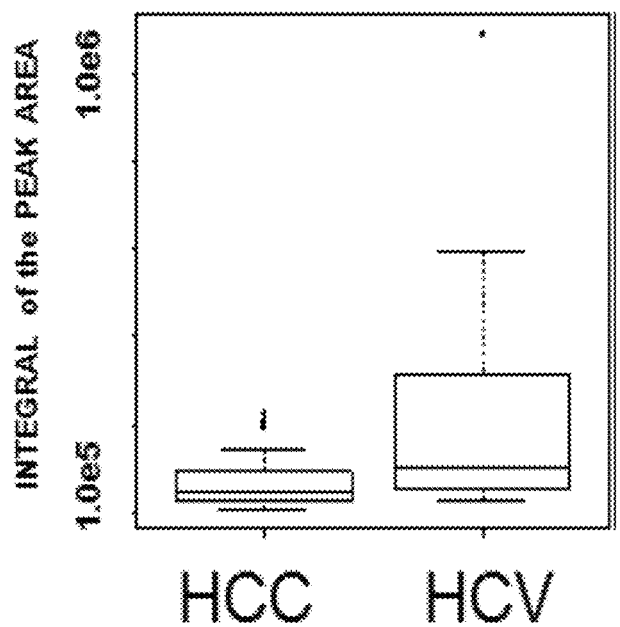
FIG. 3M. 2-deoxyguanosine.
Figure 3N:
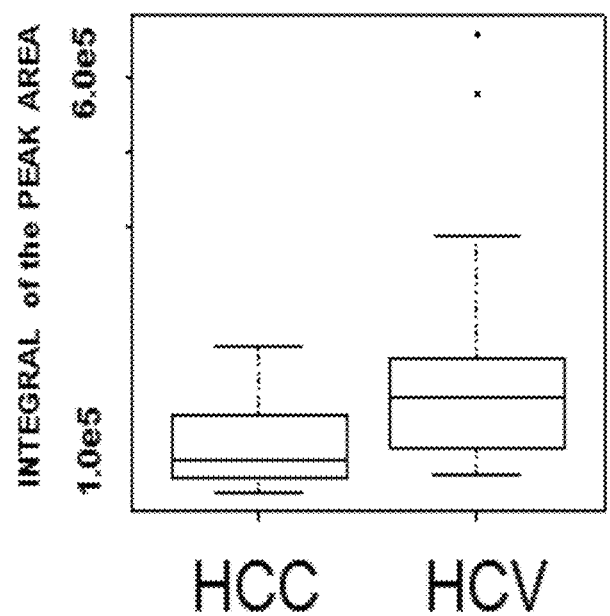
FIG. 3N, N-methylinosine.
Figure 3O:
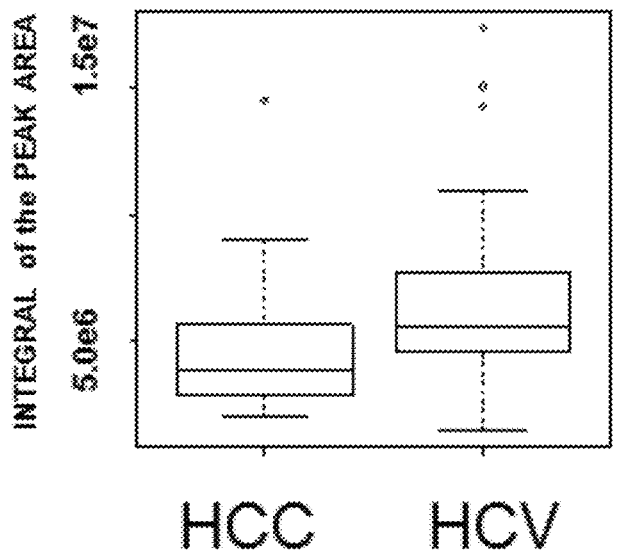
FIG. 3O, Aconitic acid.
Figure 3P:
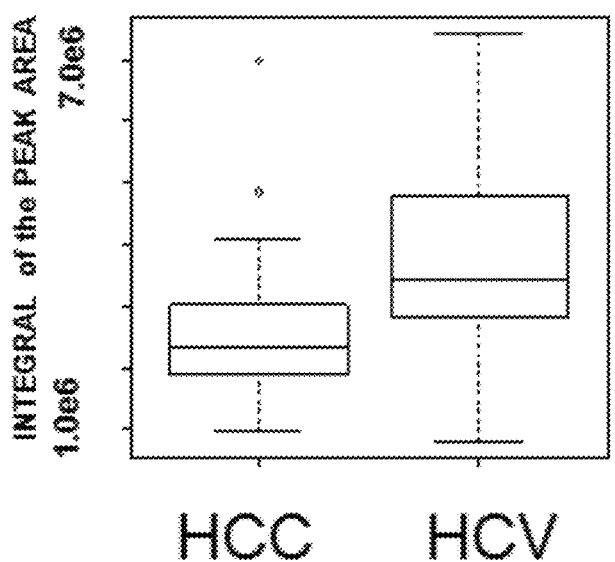

Initial data analysis based on the averaged peak areas of duplicate sample runs indicated 16 metabolites (tyrosine, phenylalanine, glycerol, 1-methylguanosine, methionine, N-carbamoyl-β alanine, xanthine, homocysteine, creatine, 1-methyladenosine, $N^2,N^2$-dimethylguanosine, 5-hydroxymethyl-2'-deoxyuridine, 2-deoxyguanosine, 1-methylinosine, aconitic acid and uric acid) had statistically significant differences in the samples of HCC and HCV patients, as indicated by p<0.05 using the Student's t-test. These metabolites varied in their levels by a factor of up to 3.3 between HCC and HCV, and all except three, creatine, 1-methyladenosine and 5-hydroxymethyl-2'-deoxyuridine were down regulated in HCC compared to HCV. Table 8, below, summarizes the results. While a number of these compounds have been observed previously as potential markers for either liver cancer or hepatitis compared to normal patient sera, to the best of our knowledge four metabolites (N-carbamoyl-beta-alanine, 5-hydroxymethyl-2'-deoxyuridine, 2-deoxyguanosine, and aconitic acid) have not been previously reported as a potential makers. The box-and-whisker plots shown in FIG. 3A to FIG. 3P indicate the discrimination power for these 16 metabolites in terms of their ability to separate sera from patients with HCC and with HCV infection. Of these 16 identified markers, 13 decreased and three increased in HCC compared to HCV infection (Table 8 below).

TABLE 8

Comparison of 16 Biomarker Candidates Found in HCC and HCV Infection

| Metabolites | HCC cf HCV infection | p-value | Fold Change (HCC/HCV) | MRM Mode |
|---|---|---|---|---|
| 5-Hydroxymethyl-2'-deoxyuridine | increase | 0.00088 | 1.5 | Positive |
| $N^2,N^2$-Dimethylguanosine | decrease | 0.0018 | 0.5 | Positive |
| Methionine | decrease | 0.0032 | 0.7 | Positive |
| Uric acid | decrease | 0.0069 | 0.7 | Negative |
| 1-Methylinosine | decrease | 0.0075 | 0.5 | Positive |
| 1-Methylguanosine | decrease | 0.0078 | 0.6 | Positive |
| 1-Methyladenosine | increase | 0.011 | 1.4 | Positive |
| Xanthine | decrease | 0.011 | 0.8 | Positive |
| Phenylalanine | decrease | 0.013 | 0.9 | Positive |
| 2-Deoxyguanosine | decrease | 0.015 | 0.3 | Positive |
| Tyrosine | decrease | 0.016 | 0.8 | Positive |
| N-Carbamoyl-Beta Alanine | decrease | 0.016 | 0.7 | Positive |
| Glycerol | decrease | 0.018 | 0.8 | Positive |
| Aconitic acid | decrease | 0.029 | 0.7 | Negative |
| Creatine | increase | 0.029 | 2.1 | Positive |
| Homocysteine | decrease | 0.036 | 0.8 | Positive |

Figure 4A:
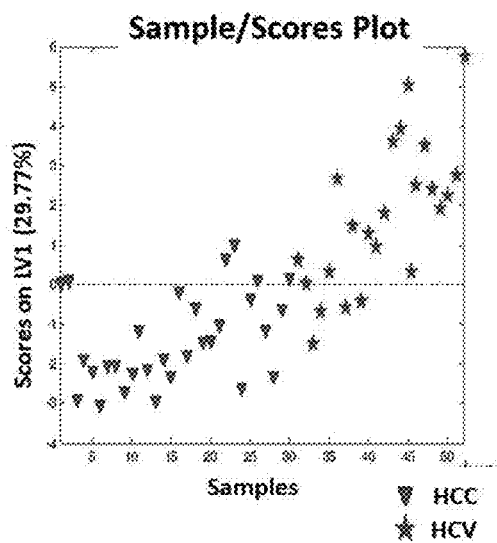
FIG. 4A and FIG. 4B show the results of the PLS-DA model from the 16 metabolite biomarkers and the ROC curve generated from the PLS-DA model.
Figure 4B:
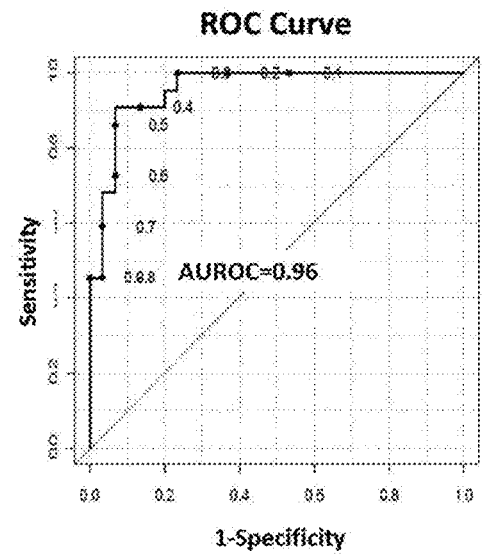

To improve the ability of these metabolites to differentiate HCC and HCV patients, a PLS-DA model was developed using the 16 biomarker candidates, and utilizing leave-one-out cross validation, as should in FIG. 4A and FIG. 4B. The model shows a clear separation between HCC and HCV patients with a sensitivity of 90% and specificity of 93%. The ROC curve for the model prediction derived from PLS-DA using HCC versus HCV shows an AUROC of 0.96.

Figure 4C:
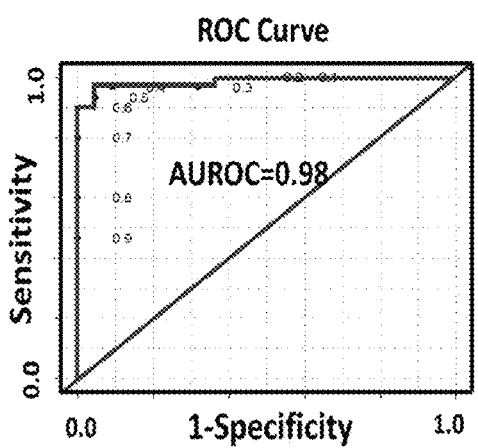
FIG. 4C shows a ROC curve generated from the PLS-DA model of four metabolites with lowest p-values between HCC and HCV: methionine, 5-hydroxymethyl-2'-deoxyuridine, $N^2,N^2$-dimethylguanosine and uric acid.

From the set of these identified metabolites that distinguish between HCC and HCV at the p<0.05 level, a smaller group of potential metabolic biomarkers were selected based on the low p-values for each compound. A PLS-DA model was built to test classification accuracy and predictive power. A group of four metabolites (methionine, 5-hydroxymethyl-2'-deoxyuridine, $N^2,N^2$-dimethylguanosine and uric acid) with the lowest p-values (p≤0.0032) provided high classification accuracy. The median level for 5-hydroxymethyl-2'-deoxyuridine increased in HCC by factor of 1.5, while the levels for the other three metabolites decreased. A PLS-DA model using this panel of four metabolic biomarkers was constructed using leave-one-out cross validation. The model showed an excellent separation between HCC and HCV patients with a sensitivity of 97% and specificity of 95%. The ROC curve shown in FIG. 4C for the prediction model has an AUROC of 0.98.

Figure 4D:
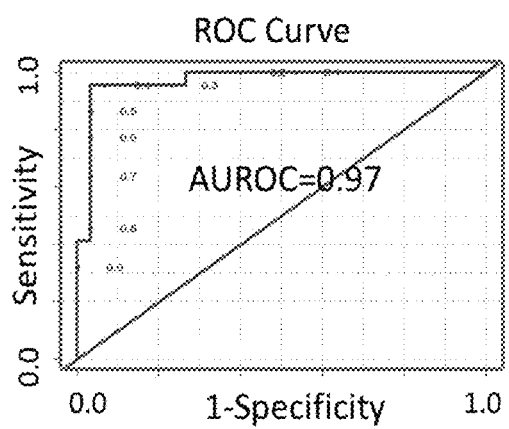
FIG. 4D shows a ROC curve generated from the PLS-DA model of the four metabolites (methionine, 5-hydroxymethyl-2'-deoxyuridine, $N^2,N^2$-dimethylguanosine and methyladenosine) selected based on variable importance in projection (VIP) analysis of metabolites using 73 metabolites. The AUROC is slight lower (0.97) compared to the area obtained from the analysis of four lowest p value metabolites (compare to FIG. 4C).

Variable importance in projection (VIP) analysis of metabolites using all 73 metabolites provided 4 metabolites (methionine, 5-hydroxymethyl-2'-deoxyuridine, $N^2,N^2$-dimethylguanosine and 1-methyladenosine) to have the highest VIP scores. While three of the metabolites (methionine, 5-hydroxymethyl-2'-deoxyuridine, $N^2,N^2$-dimethylguanosine) selected using VIP analysis were the same, one metabolite (1-methyladenosine) was different from those selected based on lowest p-values. A PLS-DA model developed using these 4 metabolites provided similar results to those derived using the 4 metabolites with the lowest p-values, but the AUROC was slightly lower (0.97 versus 0.98), FIG. 4D.

In general, panels of metabolic biomarkers are identified by the following method.

1. Identifying metabolite species that are present in the samples from both the samples from the HCC patients and the samples from the HCV patients.

2. Selecting the identified metabolite species for which the amount or peak area in the biofluid samples from the HCC patients and biofluid samples from the HCV patients is different at the level of p<0.05. The selection may be based on Student's t-test, variable importance in projection (VIP), or other suitable statistical measure.

3. Grouping the selected identified metabolite species to produce an identified panel of a plurality of metabolite species using the average p-value of the metabolic species grouped to form the panel as criterion for the initial ranking of an identified panel. In certain embodiments the average p-value of the metabolite species of an identified panel is in the range of 0.003 to 0.03.

4. Constructing a statistical model, such as a PLS-DA model, using the identified panel of metabolite species.

5. Evaluating the strength of the model, including the assessment of sensitivity, specificity, AUROC using ROC curves. The steps of identifying, selecting and grouping can be repeated to identify further panels of metabolite species.

Using this method, the sixteen metabolite species of Table 8 were combined in various panels characterized by the average p-value of the component metabolite species, and are presented in Table 9, below. Table 9 also includes the panels that have been identified and modeled in Examples 1, 2 and 3.

TABLE 9

Exemplary Panels of Metabolic Biomarkers

| Panel Members | Panel Member Compounds | Average p-value per member |
|---|---|---|
| 3 | choline, valine, creatine | 1.60E−02 |
| 4 | *5-hydroxymethyl-2'-deoxyuridine*, $N^2,N^2$-dimethylguanosine, methionine, uric acid | 3.20E−03 |
| 4 | *5-Hydroxymethyl-2'-deoxyuridine*, $N^2,N^2$-Dimethylguanosine, Methionine, 1-Methylguanosine | 3.35E−03 |
| 4 | *5-hydroxymethyl-2'-deoxyuridine*, $N^2,N^2$-dimethylguanosine, methionine, 1-methylinosine | 3.35E−03 |
| 4 | *5-hydroxymethyl-2'-deoxyuridine*, $N^2,N^2$-dimethylguanosine, methionine, xanthine | 4.22E−03 |

TABLE 9-continued

Exemplary Panels of Metabolic Biomarkers

| Panel Members | Panel Member Compounds | Average p-value per member |
|---|---|---|
| 4 | *5-hydroxymethyl-2'-deoxyuridine*, $N^2,N^2$-dimethylguanosine, methionine, 1-methyladenosine | 4.22E−03 |
| 4 | *5-hydroxymethyl-2'-deoxyuridine*, $N^2,N^2$-dimethylguanosine, methionine, phenylalanine | 4.72E−03 |
| 4 | $N^2,N^2$-dimethylguanosine, methionine, uric acid, 1-methylinosine | 4.85E−03 |
| 4 | $N^2,N^2$-dimethylguanosine, methionine, uric acid, 1-methylguanosine | 4.93E−03 |
| 4 | *5-hydroxymethyl-2'-deoxyuridine*, $N^2,N^2$-dimethylguanosine, methionine, phenylalanine | 4.72E−03 |
| 4 | *5-hydroxymethyl-2'-deoxyuridine*, $N^2,N^2$-dimethylguanosine, methionine, 2-deoxyguanosine | 5.22E−03 |
| 4 | *5-hydroxymethyl-2'-deoxyuridine*, $N^2,N^2$-dimethylguanosine, methionine, tyrosine | 5.47E−03 |
| 4 | *5-hydroxymethyl-2'-deoxyuridine*, $N^2,N^2$-dimethylguanosine, methionine, n-carbamoyl-beta alanine | 5.47E−03 |
| 4 | $N^2,N^2$-dimethylguanosine, methionine, uric acid, 1-methyladenosine | 5.73E−03 |
| 4 | $N^2,N^2$-dimethylguanosine, methionine, uric acid, xanthine | 5.73E−03 |
| 4 | *5-hydroxymethyl-2'-deoxyuridine*, $N^2,N^2$-dimethylguanosine, methionine, glycerol | 5.97E−03 |
| 4 | $N^2,N^2$-dimethylguanosine, methionine, uric acid, phenylalanine | 6.23E−03 |
| 4 | $N^2,N^2$-dimethylguanosine, methionine, uric acid, *2-deoxyguanosine* | 6.73E−03 |
| 4 | $N^2,N^2$-dimethylguanosine, methionine, uric acid, tyrosine | 6.93E−03 |
| 4 | $N^2,N^2$-dimethylguanosine, methionine, uric acid, *N-carbamoyl-beta alanine* | 6.98E−03 |
| 4 | $N^2,N^2$-dimethylguanosine, methionine, uric acid, glycerol | 7.48E−03 |
| 4 | *5-hydroxymethyl-2'-deoxyuridine, 2-deoxyguanosine, N-carbamoyl-beta alanine*, $N^2,N^2$-dimethylguanosine | 8.42E−03 |
| 4 | methionine, uric acid, xanthine, phenylalanine | 8.53E−03 |
| 4 | *5-hydroxymethyl-2'-deoxyuridine*, $N^2,N^2$-dimethylguanosine, methionine, aconitic acid | 8.72E−03 |
| 4 | *5-hydroxymethyl-2'-deoxyuridine*, $N^2,N^2$-dimethylguanosine, methionine, creatine | 8.72E−03 |
| 4 | *5-hydroxymethyl-2'-deoxyuridine, 2-deoxyguanosine, N-carbamoyl-beta alanine,* methionine | 8.77E−03 |
| 4 | methionine, uric acid, phenylalanine, *2-deoxyguanosine* | 9.78E−03 |
| 4 | *5-hydroxymethyl-2'-deoxyuridine, 2-deoxyguanosine, N-carbamoyl-beta alanine,* uric acid | 9.70E−03 |
| 4 | methionine, uric acid, phenylalanine, tyrosine | 9.78E−03 |
| 4 | $N^2,N^2$-dimethylguanosine, methionine, uric acid, aconitic acid | 1.02E−02 |
| 4 | $N^2,N^2$-dimethylguanosine, methionine, uric acid, creatine | 1.02E−02 |
| 4 | *5-hydroxymethyl-2'-deoxyuridine*, $N^2,N^2$-dimethylguanosine, methionine, homocysteine | 1.05E−02 |
| 4 | *5-hydroxymethyl-2'-deoxyuridine, 2-deoxyguanosine, N-carbamoyl-beta alanine,* 1-methyladenosine | 1.07E−02 |
| 4 | *5-hydroxymethyl-2'-deoxyuridine, 2-deoxyguanosine, N-carbamoyl-beta alanine,* xanthine | 1.07E−02 |
| 4 | $N^2,N^2$-dimethylguanosine, methionine, uric acid, homocysteine | 1.20E−02 |
| 4 | *5-hydroxymethyl-2'-deoxyuridine, 2-deoxyguanosine, N-carbamoyl-beta alanine,* tyrosine | 1.20E−02 |
| 4 | *5-hydroxymethyl-2'-deoxyuridine, 2-deoxyguanosine, N-carbamoyl-beta alanine,* glycerol | 1.25E−02 |
| 4 | *5-hydroxymethyl-2'-deoxyuridine, 2-deoxyguanosine, N-carbamoyl-beta alanine,* creatine | 1.25E−02 |
| 4 | methionine, uric acid, phenylalanine, homocysteine | 1.48E−02 |
| 4 | *5-hydroxymethyl-2'-deoxyuridine, 2-deoxyguanosine, N-carbamoyl-beta alanine, aconitic acid* | 1.52E−02 |
| 4 | *5-hydroxymethyl-2'-deoxyuridine, 2-deoxyguanosine, N-carbamoyl-beta alanine,* homocysteine | 1.70E−02 |
| 5 | methionine, uric acid, xanthine, phenylalanine, tyrosine | 1.00E−02 |
| 5 | uric acid, xanthine, cholyglycine, D-leucic acid, 3-hydroxycapric acid | 1.50E−02 |
| 5 | *5-hydroxymethyl-2'-deoxyuridine*, $N^2,N^2$-dimethylguanosine, methionine, uric acid, 1-methylguanosine | 4.12E−03 |
| 5 | *5-hydroxymethyl-2'-deoxyuridine*, $N^2,N^2$-dimethylguanosine, methionine, uric acid, 1-methylinosine | 4.06E−03 |
| 6 | *5-hydroxymethyl-2'-deoxyuridine*, $N^2,N^2$-dimethylguanosine, methionine, uric acid, 1-methylinosine, 1-methylguanosine | 4.68E−03 |
| 7 | *5-hydroxymethyl-2'-deoxyuridine*, $N^2,N^2$-dimethylguanosine, methionine, uric acid, 1-methylinosine, 1-methylguanosine, 1-methyladenosine | 5.58E−03 |
| 8 | *5-hydroxymethyl-2'-deoxyuridine*, $N^2,N^2$-dimethylguanosine, methionine, uric acid, 1-methylinosine, 1-methylguanosine, 1-methyladenosine, xanthine | 6.26E−03 |

TABLE 9-continued

Exemplary Panels of Metabolic Biomarkers

| Panel Members | Panel Member Compounds | Average p-value per member |
|---|---|---|
| 9 | *5-hydroxymethyl-2'-deoxyuridine*, $N^2,N^2$-dimethylguanosine, methionine, uric acid, 1-methylinosine, 1-methylguanosine, 1-methyladenosine, xanthine, phenylalanine | 7.01E−03 |
| 10 | *5-hydroxymethyl-2'-deoxyuridine*, $N^2,N^2$-dimethylguanosine, methionine, uric acid, 1-methylinosine, 1-methylguanosine, 1-methyladenosine, xanthine, phenylalanine *2-deoxyguanosine* | 7.81E−03 |
| 10 | methionine, uric acid, xanthine, phenylalanine, tyrosine, *N-carbamoyl-beta alanine*, glycerol, *aconitic acid*, creatine, homocysteine | 1.78E−02 |
| 11 | *5-hydroxymethyl-2'-deoxyuridine*, $N^2,N^2$-dimethylguanosine, methionine, uric acid, 1-methylinosine, 1-methylguanosine, 1-methyladenosine, xanthine, phenylalanine, *2-deoxyguanosine*, tyrosine | 8.55E−03 |
| 12 | *5-hydroxymethyl-2'-deoxyuridine*, $N^2,N^2$-dimethylguanosine, methionine, uric acid, 1-methylinosine, 1-methylguanosine, 1-methyladenosine, xanthine, phenylalanine, *2-deoxyguanosine*, tyrosine, *N-carbamoyl-beta alanine* | 9.17E−03 |
| 13 | *5-hydroxymethyl-2'-deoxyuridine*, $N^2,N^2$-dimethylguanosine, methionine, uric acid, 1-methylinosine, 1-methylguanosine, 1-methyladenosine, xanthine, phenylalanine *2-deoxyguanosine*, tyrosine, *N-carbamoyl-beta alanine*, glycerol | 9.85E−03 |
| 14 | *5-hydroxymethyl-2'-deoxyuridine*, $N^2,N^2$-dimethylguanosine, methionine, uric acid, 1-methylinosine, 1-methylguanosine, 1-methyladenosine, xanthine, phenylalanine, *2-deoxyguanosine*, tyrosine, *N-carbamoyl-beta alanine*, glycerol, *aconitic acid* | 1.12E−02 |
| 14 | methionine, uric acid, 1-methylinosine, 1-methylguanosine, 1-methyladenosine, xanthine, phenylalanine, *2-deoxyguanosine*, tyrosine, *N-carbamoyl-beta alanine*, glycerol, *aconitic acid*, creatine, homocysteine | 1.57E−02 |
| 15 | *5-hydroxymethyl-2'-deoxyuridine*, $N^2,N^2$-dimethylguanosine, methionine, uric acid, 1-methylinosine, 1-methylguanosine, 1-methyladenosine, xanthine, phenylalanine, *2-deoxyguanosine*, tyrosine, *N-carbamoyl-beta alanine*, glycerol, *aconitic acid*, creatine | 1.24E−02 |
| 16 | *5-hydroxymethyl-2'-deoxyuridine*, $N^2,N^2$-dimethylguanosine, methionine, uric acid, 1-methylinosine, 1-methylguanosine, 1-methyladenosine, xanthine, phenylalanine, *2-deoxyguanosine*, tyrosine, *N-carbamoyl-beta alanine*, glycerol, *aconitic acid*, creatine, homocysteine | 1.39E−02 |
| 21 | *5-hydroxymethyl-2'-deoxyuridine*, $N^2,H^2$-dimethylguanosine, methionine, uric acid, 1-methylinosine, 1-methylguanosine, 1-methyladenosine, xanthine, phenylalanine, *2-deoxyguanosine*, tyrosine, *N-carbamoyl-beta alanine*, glycerol, *aconitic acid*, creatine, homocysteine, valine, cholyglycine, d-leucic acid, creatinine, 3-hydroxycapric acid | NA |

A schematic diagram of disturbed metabolic pathways is provided in FIG. 5. In the figure, metabolites that showed statistically significant alterations in intensity in this example are shown in rectangular boxes. Three up-regulated metabolites are shown with an upward pointing arrow. A number of altered metabolic pathways including the beta-alanine pathway (metabolite: N-carbamoyl-beta-alanine), glycolipid (glycerol), amino acid (phenylalanine, tyrosine, creatine, cysteine, methionine, homocysteine), purine (xanthine and uric acid), and nucleoside pathways (1-methyladenosine, 1-methylinosine, 2-deoxyguanosine, 1-methylguanosine and $N^2,N^2$-dimethylguanosine) were identified as being affected due to HCC, based on the 16 metabolites with altered levels. To the best of our knowledge, four of these 16 metabolites (N-carbamoyl-beta-alanine, 5-hydroxymethyl-2'-deoxyuridine, 2-deoxyguanosine, and aconitic acid) have not been previously reported as being associated with the development of liver cancer, and are indicated in bold italics in Table 9, above. The remaining twelve of the sixteen metabolites have been reported as potential biomarkers for liver cancer and hepatitis in other studies.

EXAMPLE 3

Hepatocellular carcinoma (HCC) accounts for most liver cancer cases worldwide. Infection with hepatitis C virus (HCV) is considered a major risk factor for liver cancer. To identify cancer risk, metabolic profiling of serum samples from patients with HCC (n=40) and HCV (n=22) was performed by $^1$H nuclear magnetic resonance spectroscopy. Multivariate statistical analysis showed a distinct separation of the two patient cohorts indicating a distinct metabolic difference between HCC and HCV based on signals from lipids and individual metabolites. Univariate analysis showed that three metabolites (choline, valine and creatinine) were significantly altered in HCC. A PLS-DA model based on these three metabolites showed a sensitivity of 80%, specificity of 71%, and area under the receiver operating curve of 0.83, outperforming the clinical marker alpha-fetoprotein (AFP). The robustness of the model was indicated by Monte-Carlo cross validation (MCCV). This study discloses a panel of metabolic biomarkers that is useful for HCC screening in HCV patients, many of whom have high risk for developing liver cancer.

This study focused on a particularly challenging patient cohort, those HCC patients with underlying HCV. It is extremely difficult to differentiate HCC patients with underlying HCV from HCV patients for several reasons: 1) mediators associated with inflammation often overlap with those associated with cancer and therefore teasing out cancer specific differences is difficult; 2) changes associated with fibrosis also overlap with cancer and the majority of HCV patients do not develop cancer until the liver has become severely fibrotic; and 3) confirmation of cancer requires pathologic evidence that is not possible in cases where resection or transplant is not performed or occult disease is present, but under the detection of the most sophisticated tests. Patients with HCV were of particular interest for this study since they represent the largest cohort of HCC patients in the US and are at the highest risk for developing HCC during their lifetimes.

Profiles of metabolites in blood serum were constructed using NMR spectroscopy, LC-MS, and statistical analysis methods. The metabolite biomarkers discovered were selected to build a predictive model that was then used to test the classification accuracy.

Serum samples from 40 HCC patients with underlying HCV and cirrhosis collected before radiation or chemotherapy treatments, and 22 HCV patients with cirrhosis were studied. Most of these patients are Caucasians. Metabolite profiles were performed using $^1$H NMR and analyzed statistically using several approaches including partial least squares discriminant analysis (PLS-DA). A good model could be built based on the entire NMR spectrum as well as on only three metabolite biomarkers, and these results were internally cross-validated. This study is the first to identify good serum metabolite biomarkers by NMR to distinguish HCC patients from a population of patients with HCV and cirrhosis in the U.S.

Chemicals. Deuterium oxide ($D_2O$, 99.9% D) and sodium azide ($NaN_3$) were purchased from Cambridge Isotope Laboratories, Inc. (Andover, Mass.). The sodium salt of trimethylsilylpropionic acid-d4 (TSP), used as the internal standard, was from Sigma-Aldrich (Milwaukee, Wis.). All chemical reagents were analytical grade and used without further purification.

Serum Sample Collection and Storage. Human serum samples (n=62) were obtained from the Indiana University/Lilly tissue bank, and consisted of two cohorts: HCC patients (n=40) with underlying HCV, and HCV patients (n=22) without HCC. A summary of sample information can be seen in Table 10, below. Frozen samples were transported to Purdue University under dry ice and then kept at −80° C. until analysis. The study was approved by the Institutional Review Boards at both Purdue University and Indiana University School of Medicine.

TABLE 10

Summary Of Demographic And Clinical Information For Subjects Recruited For The Study.

|  | HCC | HCV |
|---|---|---|
| Samples | 40 | 22 |
| Average Age | 54.6 ± 9.8 | 52.2 ± 8.1 |
| Gender (F/M) | 0.21 | 0.46 |

TABLE 10-continued

Summary Of Demographic And Clinical Information For Subjects Recruited For The Study.

|  | HCC | HCV |
|---|---|---|
| Ethnicity |  |  |
| Caucasian | 32 | 20 |
| African American | 1 | 2 |
| Hispanic | 3 | 0 |
| Unknown | 4 | 0 |

Sample preparation and acquisition of NMR spectra. Samples were prepared by mixing 400 μL serum with 5 μL sodium azide (0.01% w/v) and 130 μL $D_2O$. The solution (530 μL) was then transferred to a 5-mm NMR tube. A 60 μL, 0.5 mM TSP solution contained in a capillary insert was used as an internal standard. For the 1D NMR experiments, the spectra were acquired at 298 K on a Bruker Avance-500 spectrometer equipped with a TXI gradient cryoprobe, using standard 1D NOESY and 1D CPMG (Carr-Purcell-Meiboom-Gill) pulse sequence coupled with water presaturation. For each spectrum, 128 transients were collected with 16 k time domain data points and using a spectral width of 6,000 Hz. All spectra were Fourier transformed using a 1.0 Hz exponential line broadening. Each acquired spectrum was then phased, baseline corrected and aligned with reference to alanine ($\delta$=1.479 ppm) using Bruker Topspin 3.0 software.

Statistical Analysis. After excluding the spectral region $\delta$ 4.7-5.2 ppm containing the residual water resonance, each spectrum was binned to 4096 points (bin size 0.003 ppm), and then normalized to the area of the TSP signal at 0.0 ppm. The spectral data from both the CPMG and NOESY experiments were initially mean centered and subjected to orthogonal-signal-corrected (OSC) partial least squares (PLS) analysis using Matlab (R2008a; Mathworks, Natick, Mass.) and the PLS Toolbox (version 4.11, Eigenvector Research Inc.).

In a second, more targeted analysis, a total of nineteen metabolites were identified in the CPMG spectra by comparing their chemical shifts and multiplicities with the Human Metabolome Data Base. The individual spectral regions for each of the nineteen metabolite signals were then integrated. After autoscaling, these peak integrals for both the HCC patients (n=40) and HCV patients (n=22) were subjected to principal component analysis (PCA) as well as partial least squares discriminant analysis (PLS-DA) with 7-fold internal cross-validation for model building. A receiver operating characteristics (ROC) curve was used to evaluate the performance of that model. Monte Carlo Cross Validation (MCCV) with 200 iterations was used to assess the model robustness using Matlab, PLS Toolbox version 4.11 and privately developed software. For each of the iterations, the whole dataset was randomly divided into the training set (60% of the whole data set) and a testing set (40%). A PLS-DA model was built on the training set with 7-fold internal cross-validation to predict the validation set. The internal cross-validation prediction on the training set and the external prediction of the validation set were combined as the predicting result for each MCCV run. The overall true positive and true negative numbers were summarized, after which the sensitivity and specificity were calculated and compared with the results of a permutation analysis. In the permutation, the sample classification was randomly permuted and 200 MCCV iterations were performed as above.

Third, feature selection using the Student's t-test was performed for each metabolite between the HCC and HCV cohorts to focus the analysis on the most important metabolites for classification. Three significant metabolites (valine, creatinine and choline) with low (uncorrected, see below) p-values (<0.05) were selected as potential biomarkers. A new PLS-DA model was built, followed by MCCV and permutation with 200 iterations. Except for using three metabolite signals instead of nineteen, all the other procedures are the same as above. PCA analysis was also performed on these three biomarkers.

Figure 6A:
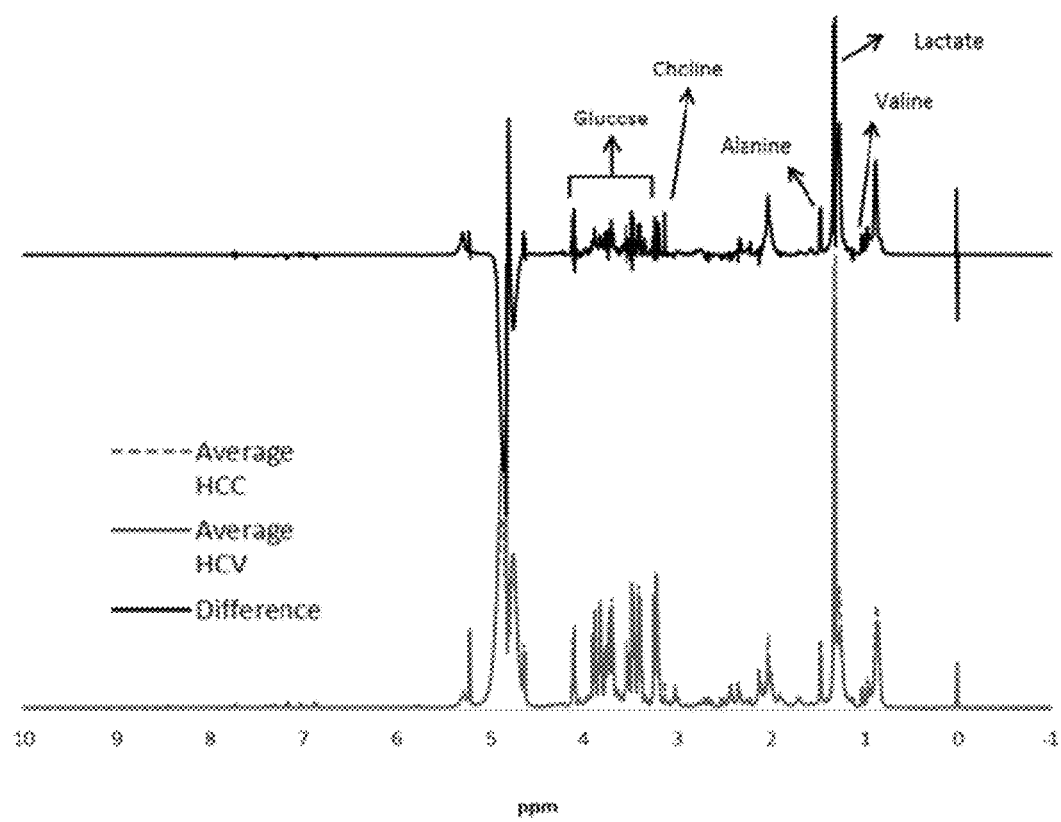
FIG. 6A shows the averaged CPMG spectra (bottom) for the HCC patients (dashed line, n=40) and HCV patients (solid line n=22), along with the difference spectrum (top, solid line). Major differences in metabolites are indicated in the difference spectrum.
Figure 6B:
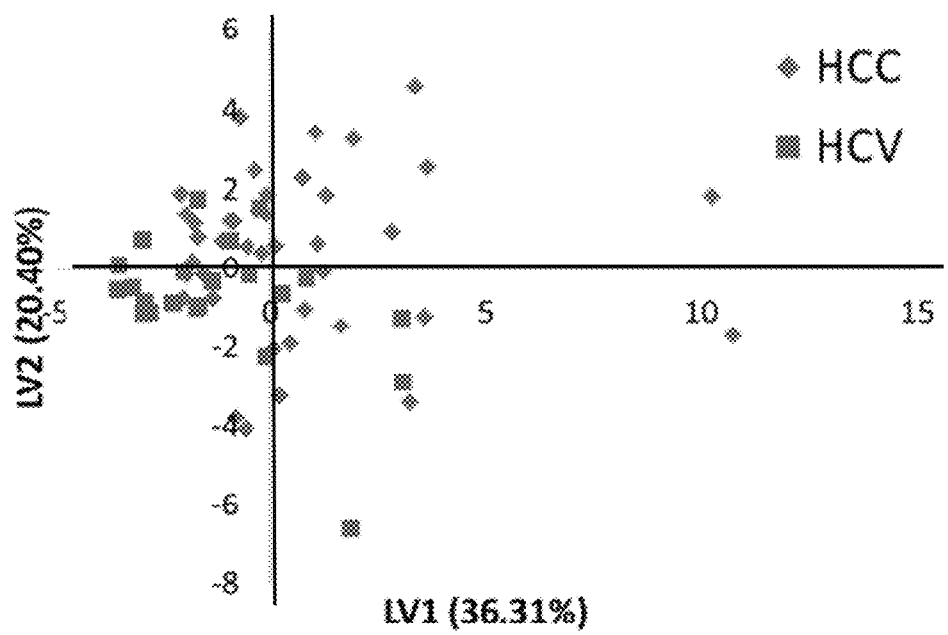
FIG. 6B shows the score plot for the OSC-PLS (orthogonal-signal-corrected partial least squares) analysis of the $^1$H CPMG NMR spectra for all samples.
Figure 6C:
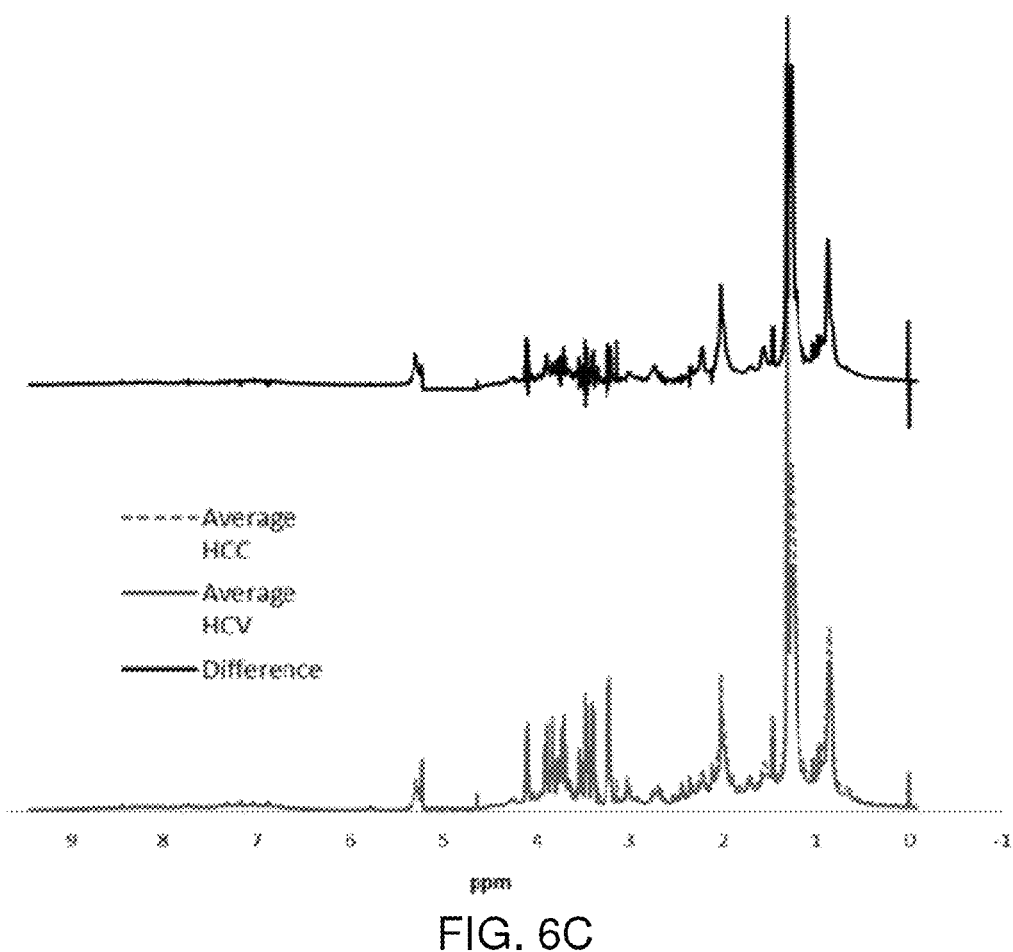
FIG. 6C shows the averaged NOESY spectra (bottom) for the HCC patients (dashed line, n=40) and HCV patients (solid line n=22), along with the difference spectrum (top, solid line). Major differences in metabolites are indicated in the difference spectrum.

The CPMG and NOESY spectra, averaged over the samples from each of the HCC and HCV patient cohorts (lower trace), along with a difference spectrum (upper trace), are shown in FIG. 6A and FIG. 6C, respectively. FIG. 6A shows the averaged CPMG spectra (bottom) for the HCC patients (dashed line, n=40) and HCV patients (solid line n=22), along with the difference spectrum (top, solid line). Major differences in metabolites are indicated in the difference spectrum. We can observe clear changes in the CPMG spectra from several of the metabolite signals, including those from glucose, valine, alanine, lactate and choline. The changes from NOESY spectra are also clear, with most contributions coming from broad lipid signals. FIG. 6C shows the averaged NOESY spectra (bottom) for the HCC patients (dashed line, n=40) and HCV patients (solid line n=22), along with the difference spectrum (top, solid line). Major differences in metabolites are indicated in the difference spectrum. However, the large variation between samples makes it difficult to give any solid conclusion.

Figure 7:
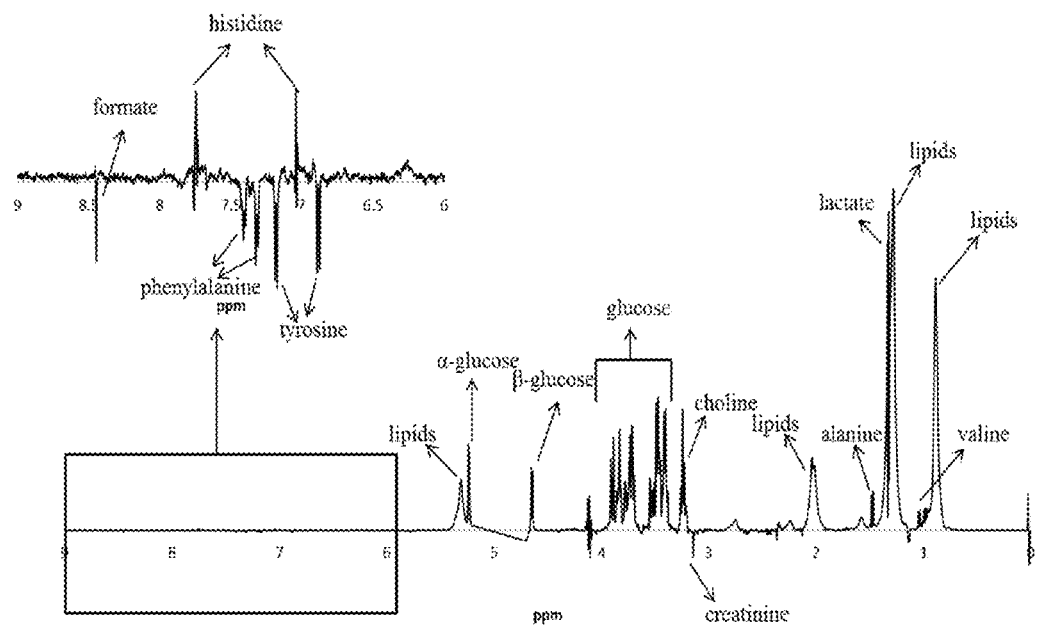
FIG. 7 shows the loadings plot along LV1 for OSC-PLS analysis of all CPMG spectral data.

The metabolic differences in both the NOESY and CPMG spectra between HCC and HCV patients can be identified using OSC-PLS analysis. The score plot for OSC-PLS analysis of the CPMG spectra is shown in FIG. 6B. The two patient cohorts are separated and clustered in different areas of this score plot, with a few HCC samples (diamonds) overlapping the region of HCV samples (squares). The AUC for separation along LV1 was 0.71, with moderate sensitivity (0.74) but poor specificity (0.60). FIG. 7 shows the loadings plot along LV1 for OSC-PLS analysis of all CPMG spectral data. The loading plot indicates that a number of peaks contribute to the separation.

Figure 6D:
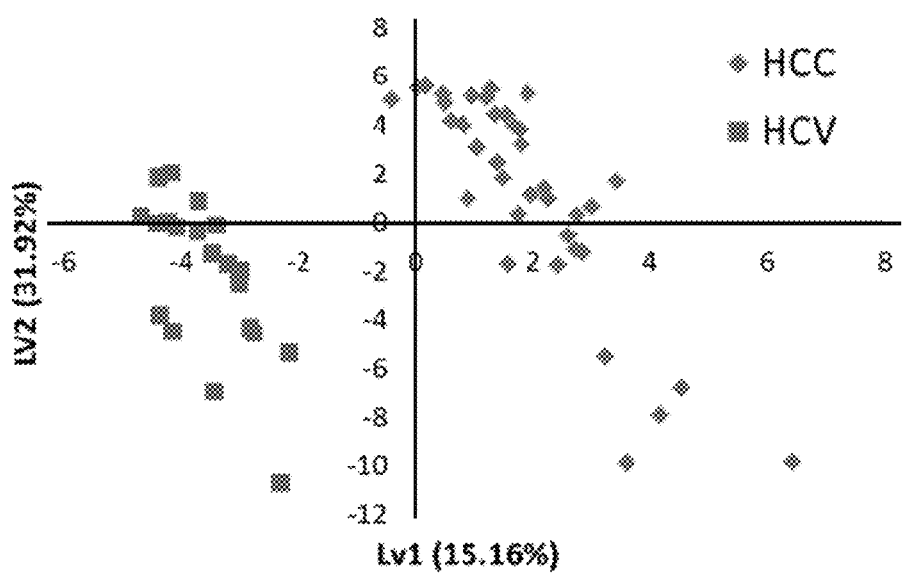
FIG. 6D shows the score plot for the OSC-PLS analysis of the NOESY spectra for all samples.
Figure 8A:
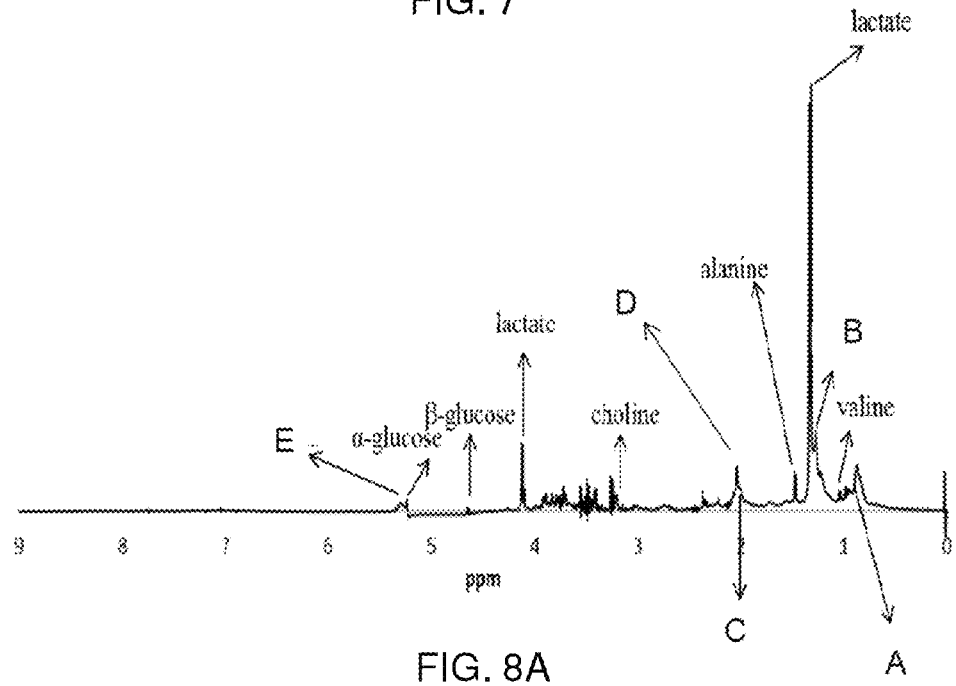
FIG. 8A shows the loadings plot along LV1 for OSC-PLS analysis of all NOESY spectral data. See Table 11 for further characterization of the peaks labeled A-E.
Figure 8B:
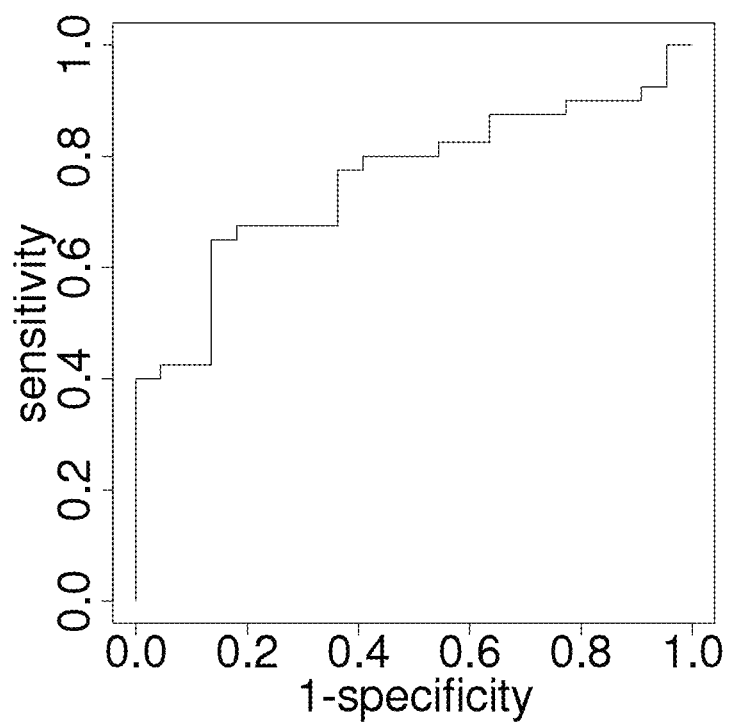
FIG. 8B shows the ROC plot for the prediction result, with AUC of 0.75, of the PLS-DA model based on the five peaks labeled A-E in FIG. 8A.

The score plot from the OSC-PLS analysis of the NOESY spectra, FIG. 6D, shows an even better separation between the two patient cohorts. The loading plot shows mostly lipid peaks. FIGS. 8A and 8B show the loadings plot along LV1 for OSC-PLS analysis of all NOESY spectral data. Five specific NOESY peaks that distinguish HCV and HCC at p<0.05 are identified in listed in Table 11, below. A PLS-DA model using these five specific NOESY peaks performs reasonably well. As shown in FIG. 8B, the ROC curve indicates a sensitivity of 65% with a specificity of 85%, and an overall area under the curve (AUROC) of 0.75. These results indicate the utility of such lipid moieties as metabolic biomarkers.

TABLE 11

NOESY Moiety Peaks That Distinguish HCV and HCC, p <0.05

| FIG. 8A Peak | ppm | Moiety | Assignment | p-value |
|---|---|---|---|---|
| A | 0.80-0.92 | lipid (mainly LDL) | $CH_3(CH_2)_n$ | 0.005 |
|   |   | lipid (mainly VLDL) | $CH_3CH_2CH_2C=$ |   |

TABLE 11-continued

NOESY Moiety Peaks That Distinguish HCV and HCC, p <0.05

| FIG. 8A Peak | ppm | Moiety | Assignment | p-value |
|---|---|---|---|---|
| B | 1.18-1.31 | lipid (mainly LDL) | $(CH_2)_n$ | 0.04 |
|   |   | lipid (mainly VLDL) | $CH_2CH_2CH_2CO$ |   |
| C | 1.94-1.99 | lipid | $CH_2C=C$ | 0.003 |
| D | 2.02-2.06 | glycoprotein | $NHCOCH_3$ | 0.0002 |
| E | 5.25-5.38 | unsaturated lipid | $CH=CHCH_2CH=CH=CHCH_2CH_2$ | 0.02 |

Considering the contribution to the loading plots from many low-lying and unidentified metabolite peaks, as well as noise, a more targeted approach was also pursued. Individual peaks from nineteen known metabolites (See Table 12, below) were integrated and analyzed to reduce the contribution from chemical noise and to focus the analysis on known molecular species to provide more mechanistic information.

TABLE 12

Assignments Of 19 Metabolites

| Metabolite | Chemical shift (ppm) | multiplicity |
|---|---|---|
| alanine | 1.48 | d |
| arginine | 1.68 | m |
| asparagine | 2.94 | m |
| CHOLINE | 3.2 | d |
| citrate | 2.53 | d |
| CREATININE | 3.03 | s |
| formate | 8.44 | s |
| glucose | 5.23 | d |
| glutamine | 2.45 | m |
| histidine | 7.05 | d |
| isoleucine | 0.92 | t |
| lactate | 4.1 | q |
| leucine | 0.94 | t |
| lysine | 1.89 | m |
| phenylalanine | 7.36 | m |
| proline | 4.08 | dd |
| threonine | 4.25 | m |
| tyrosine | 6.94 | m |
| VALINE | 1.03 | d |

Figure 9A:
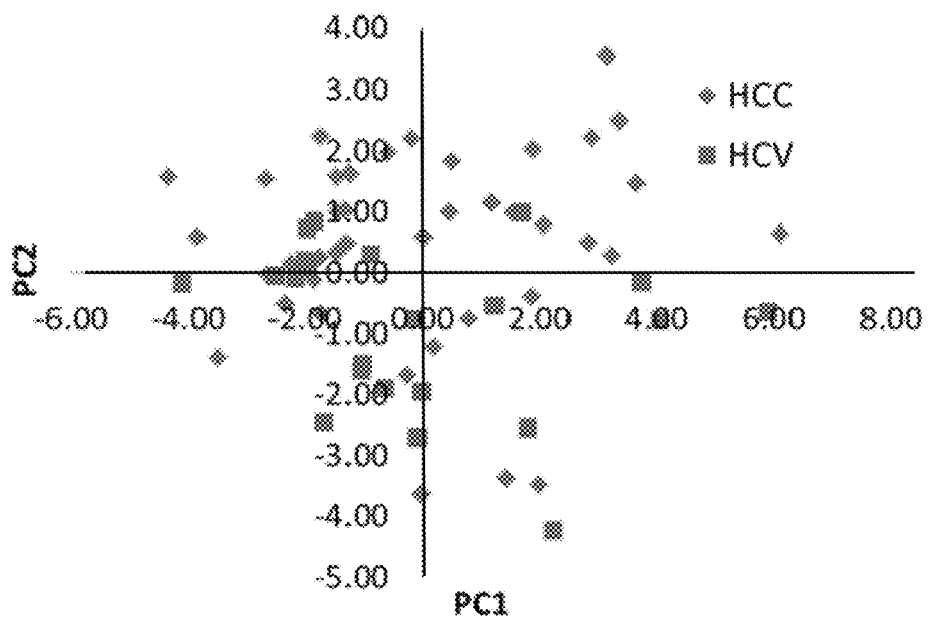
FIG. 9A shows the score plot of the PCA analysis based on nineteen identified metabolites in the spectra of the HCC and HCV samples.
Figure 9B:
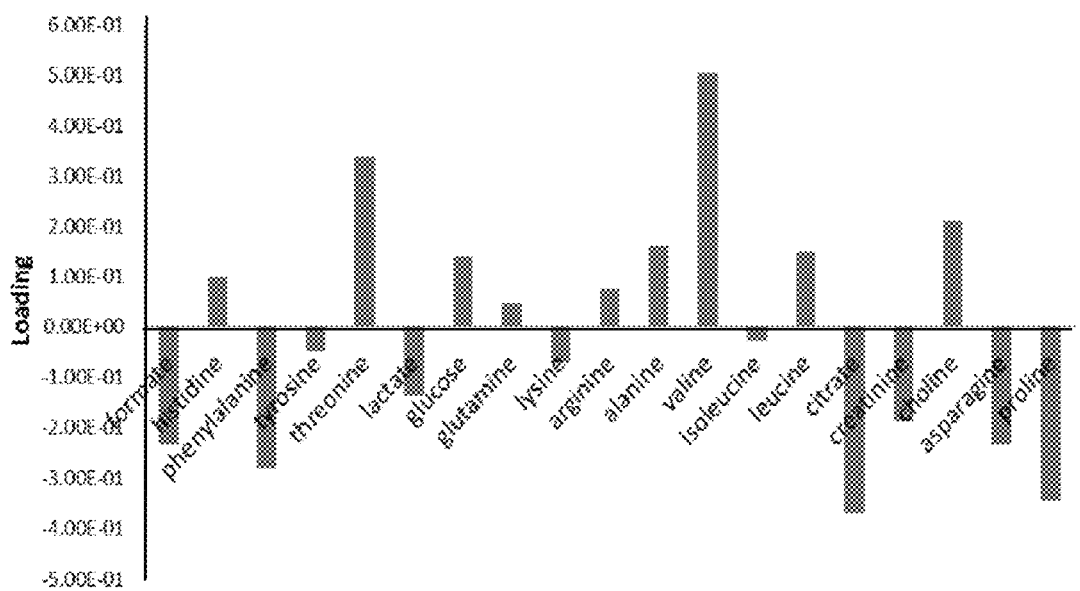
FIG. 9B shows the loading on PC2 of the PCA analysis based on nineteen identified metabolites in the spectra of the HCC and HCV samples.
Figure 10A:
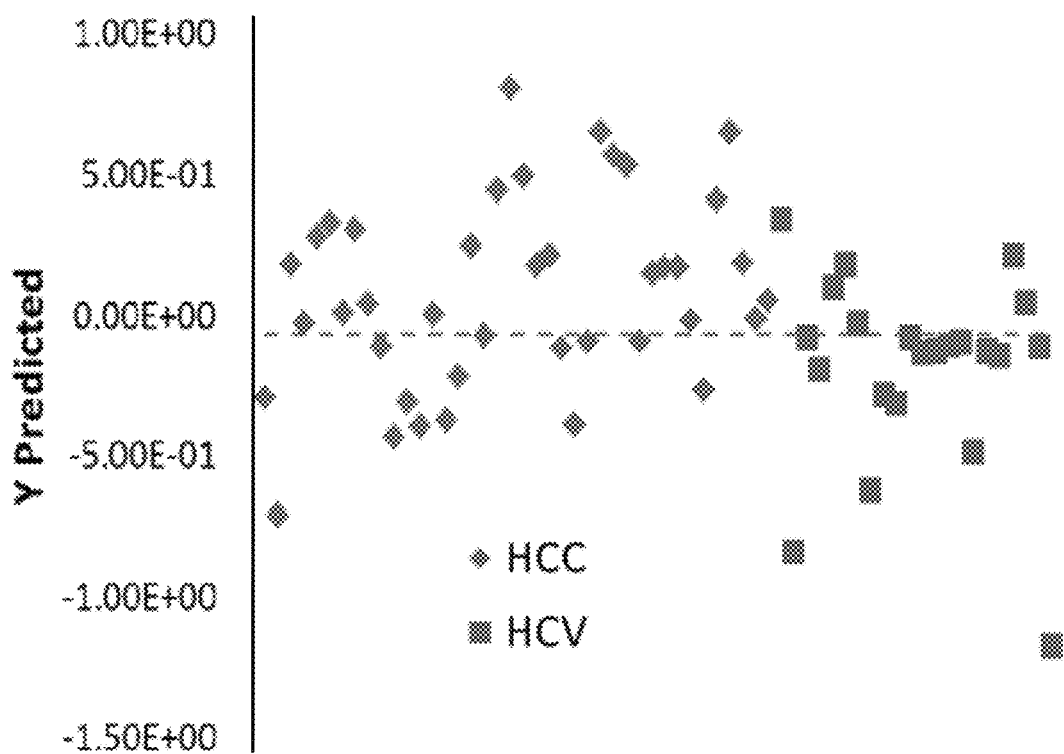
FIG. 10A shows the cross-validation predicted class values of the PLS-DA model based on nineteen identified metabolites in the spectra of the HCC and HCV samples.
Figure 10B:
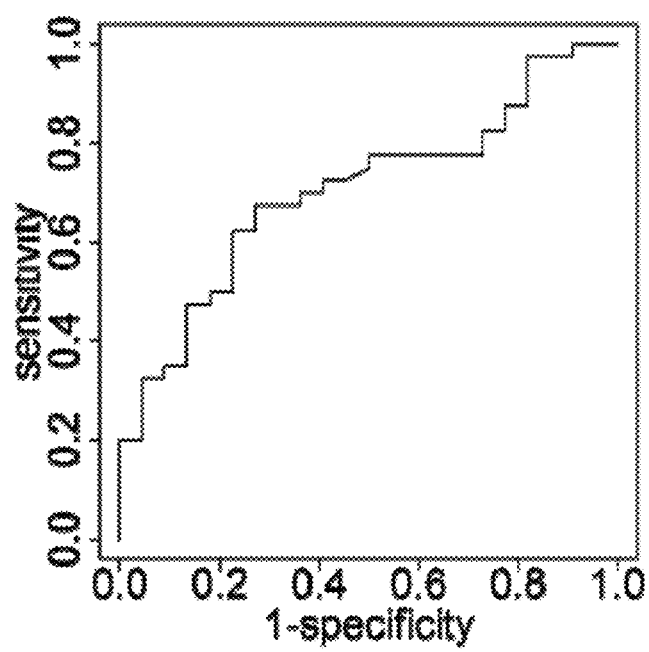
FIG. 10B shows the ROC curve for the prediction result, with AUC of 0.71, of the PLS-DA model based on nineteen identified metabolites in the spectra of the HCC and HCV samples.

Initially, PCA analysis was performed on the nineteen metabolites to see the data clustering. The results are shown in FIG. 9A and FIG. 9B. FIG. 9A shows the score plot of the PCA analysis based on nineteen identified metabolites in the spectra of the HCC and HCV samples. FIG. 9B shows the loading on PC2 of the PCA analysis based on nineteen identified metabolites in the spectra of the HCC and HCV samples. As anticipated, clear separation of the two groups was not observed in the PCA results. A PLS-DA model was built based on these metabolite signals to investigate classification and discrimination. FIG. 10A shows the cross-validation predicted class values of the PLS-DA model based on nineteen identified metabolites in the spectra of the HCC and HCV samples. FIG. 10B shows the ROC curve for the prediction result, with AUC of 0.71, of the PLS-DA model based on nineteen identified metabolites in the spectra of the HCC and HCV samples. The two sample classes are somewhat separated by this model, but a number of misclassifications again are found.

Figure 11:
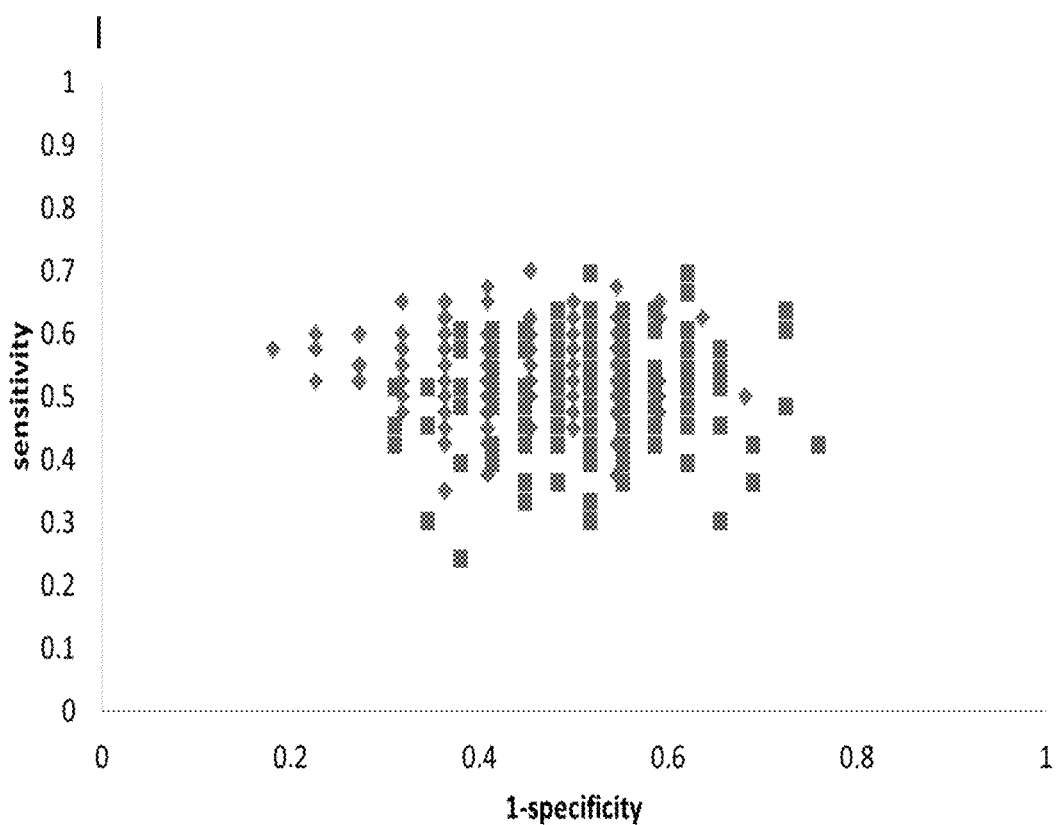
FIG. 11 shows the MCCV results (200 iterations) shown in ROC space for PLS-DA models based on the nineteen metabolites used to discriminate HCC from HCV. Each diamond represents an iteration of the true model; each square represents an iteration of the permutation model.

The model was further tested by MCCV, and the results of the classification confusion matrix are shown in Table 13, below. The low sensitivity (54%) and specificity (58%) that result from the MCCV procedure indicate that the model is not very strong. However, this model is still better than the permutation result (these data are provided in Table 12 as the values in parentheses). The sensitivity and specificity of the permutation test are only 50% and 48%, respectively, which is essentially a random result, as anticipated. The sensitivity and specificity results for both the true model and permutation test from 200 iterations are also plotted in FIG. 11. FIG. 11 shows the MCCV results (200 iterations) shown in ROC space for PLS-DA models based on the nineteen metabolites used to discriminate HCC from HCV. Each diamond represents an iteration of the true model; each square represents an iteration of the permutation model. Although not very impressive, there is still some separation, which indicates that the predictive model is better than a random one.

TABLE 13

Confusion matrix calculated from PLS-DA using 19 serum metabolites for the HCC (n = 40) and HCV (n = 22) patients using 200 MCCV iterations. The numbers in parentheses are the results from permutation analysis.

| | | Predicted class | |
|---|---|---|---|
| True class | Total number of samples | HCC | HCV |
| HCC | 8000 (8000) | 4345 (4027) | 3565 (3973) |
| HCV | 4400 (4400) | 1865 (2280) | 2535 (2120) |

Figure 12:
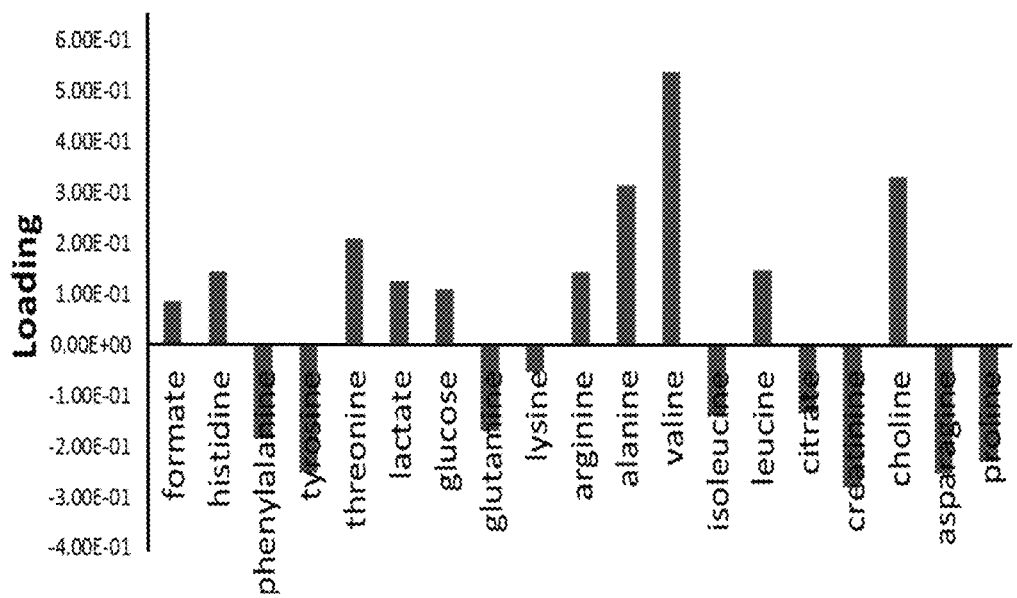
FIG. 12 shows the loadings plot of the nineteen metabolites for PLS-DA.
Figure 13A:
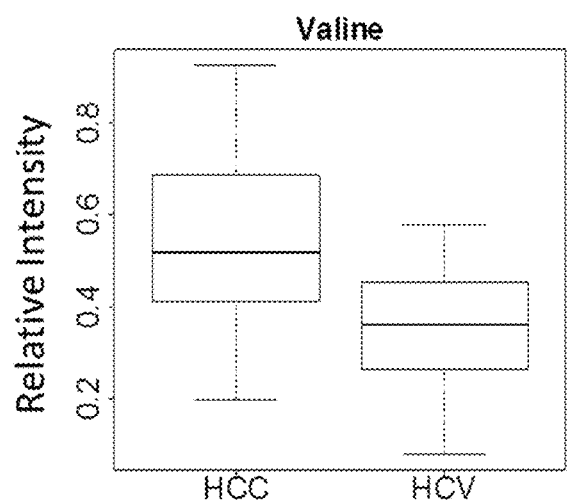
FIG. 13A, FIG. 13B and FIG. 13C are box and whisker plots for metabolite biomarkers valine (FIG. 13A), creatinine (FIG. 13B), and choline (FIG. 13C), in all the samples of this study (HCC vs HCV).
Figure 13B:
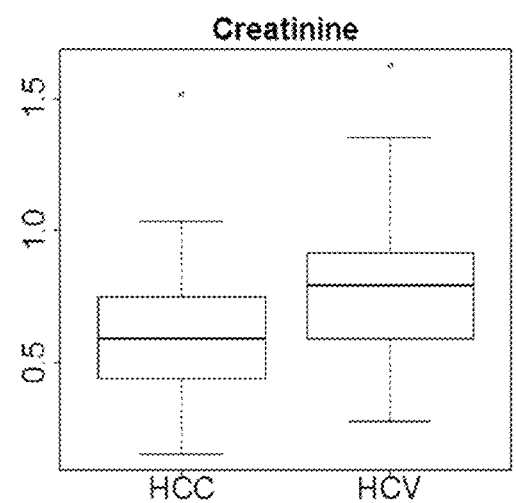
Figure 13C:
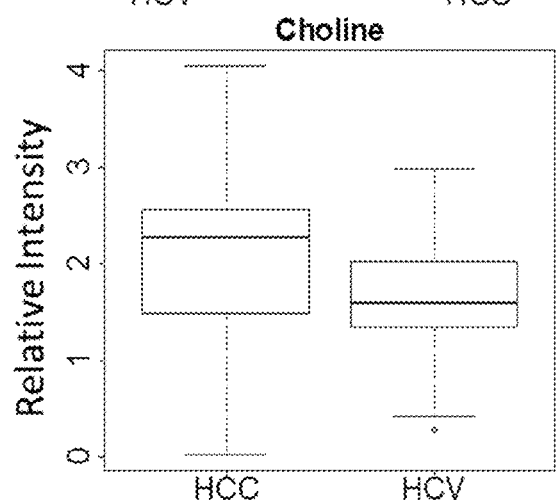

Analysis of the PLS-DA loading plots in FIG. 12 indicated that only a few metabolites, such as valine, choline, alanine, creatinine and asparagine, contributed to the separation. Feature selection was therefore used to further filter the metabolite signals and focus the analysis on the true differences between the two patient cohorts. P-values from the unpaired Student's t-test were calculated for all nineteen metabolites, and those metabolites with p<0.05 were selected. Only three metabolites (choline, valine, and creatinine) passed this filter, and the p-values, fold changes, NMR chemical shifts and multiplicities for the three metabolites are listed in Table 14, below. Box-plots of the intensity data for the three metabolites FIG. 13A, FIG. 13B and FIG. 13C indicate that choline and valine are up-regulated in HCC, while creatinine is down-regulated.

Figure 14A:
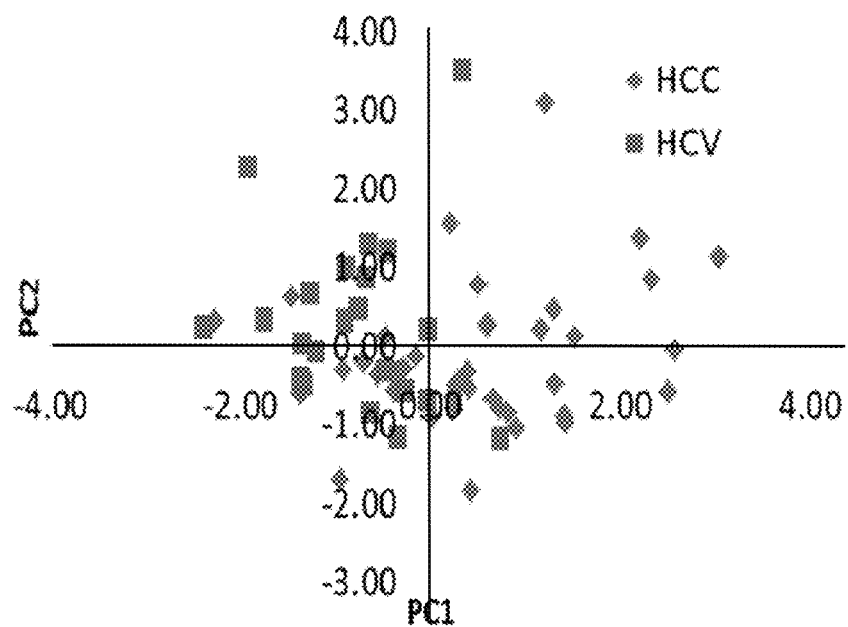
FIG. 14A shows the score plot of the PCA analysis based on the three identified metabolites in the spectra of the HCC and HCV samples.
Figure 14B:
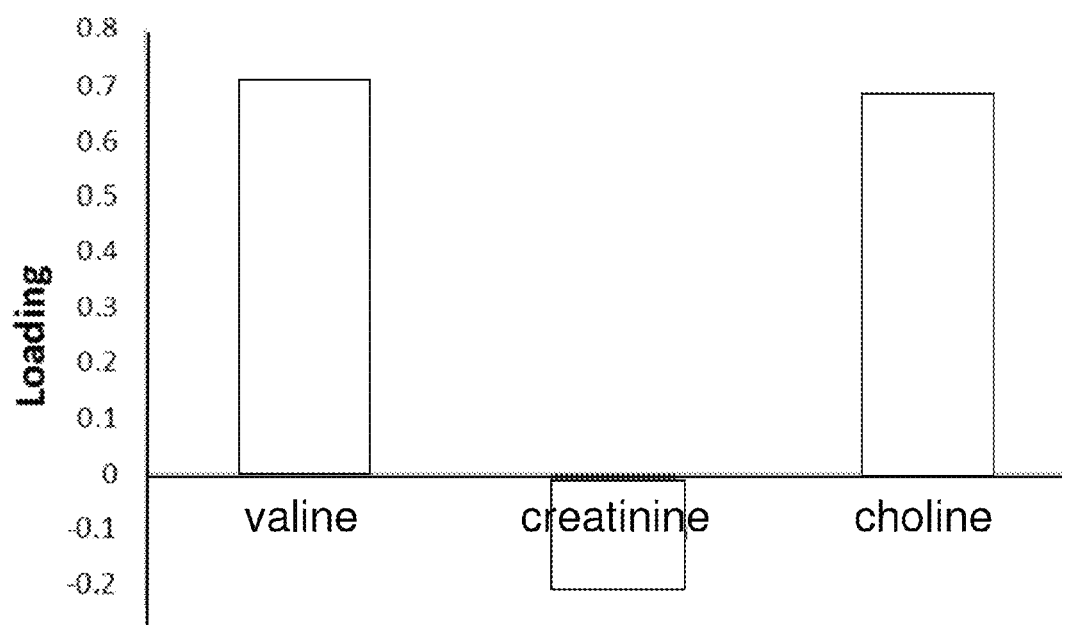
FIG. 14B shows the loading on PC1 of the PCA analysis based on the three identified metabolites in the spectra of the HCC and HCV samples.

FIG. 14A shows the score plot of the PCA analysis based on the three identified metabolites in the spectra of the HCC and HCV samples. FIG. 14B shows the loading on PC1 of the PCA analysis based on the three identified metabolites in the spectra of the HCC and HCV samples.

Figure 15A:
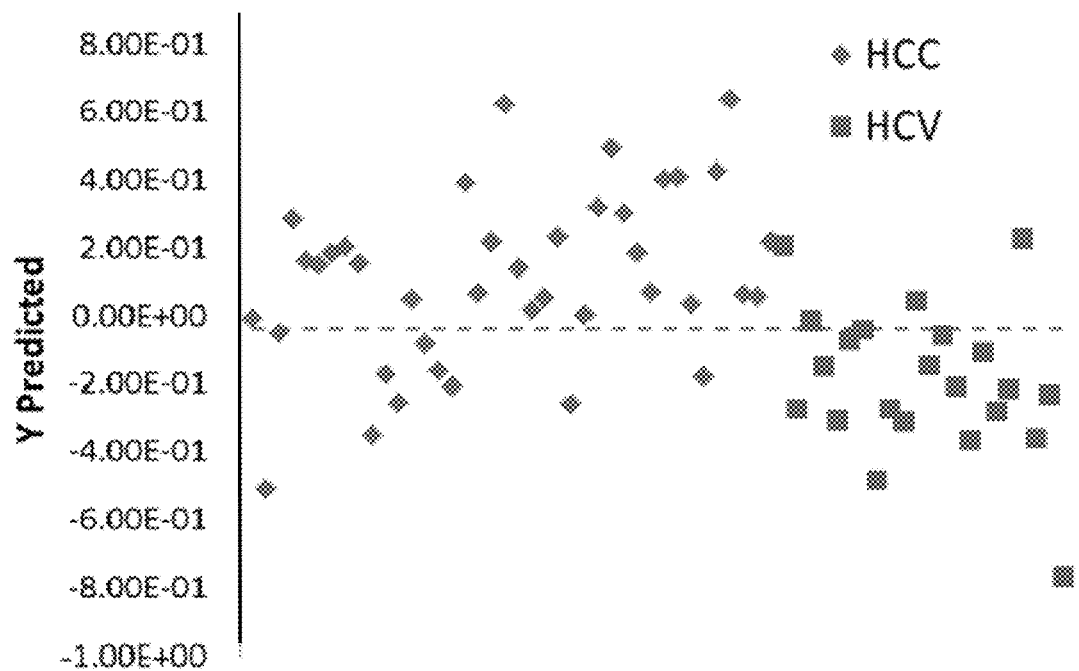
FIG. 15A shows the cross-validation predicted class values of the PLS-DA model based on the three identified metabolites in the spectra of the HCC and HCV samples.
Figure 15B:
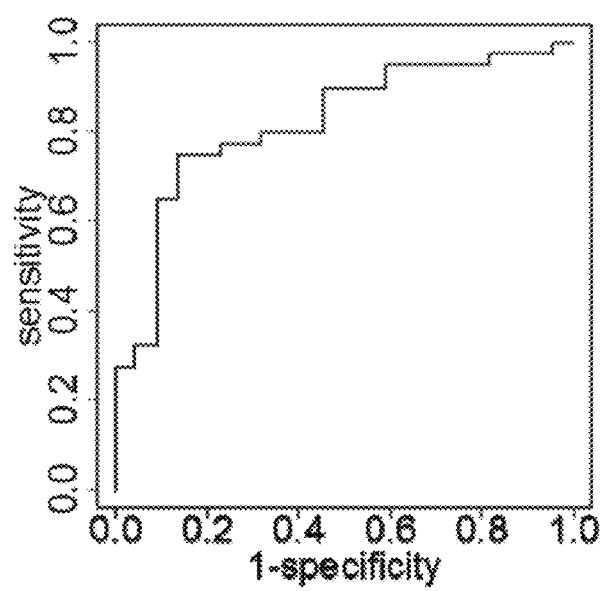
FIG. 15B shows the ROC curve for the prediction result, with AUC of 0.83, of the PLS-DA model based on nineteen identified metabolites in the spectra of the HCC and HCV samples.

A new PLS-DA model was built based on the three metabolites, and the cross validation prediction results are shown in FIG. 15A and FIG. 15B. FIG. 15A shows the cross-validation predicted class values of the PLS-DA model based on the three identified metabolites in the spectra of the HCC and HCV samples. FIG. 15B shows the ROC curve for the prediction result, with AUC of 0.83, of the PLS-DA model based on nineteen identified metabolites in the spectra of the HCC and HCV samples. A much better result can be seen both in the classification and the ROC curve. The new AUC is 0.83, indicating that this is an improved model. A sensitivity of 80% can be obtained with a specificity of 71%, outperforming the clinical marker AFP, which has a sensitivity of 41% to 65% and specificity of 80% to 94% when using AFP level>20 µg/L as the cutoff for HCC vs HCV. PCA analysis on these three markers showed some separation along PC1 as shown in FIG. 14A.

TABLE 14

Summary Of Three Metabolites Having Low p-values

| Metabolite | Chemical Shift (ppm) | Multiplicity | p-value (HCC vs HCV) | Fold change |
|---|---|---|---|---|
| Choline | 3.20 | s | 0.0200 | 1.32 |
| Valine | 1.03 | d | $5.67 \times 10^{-6}$ | 1.53 |
| Creatinine | 3.03 | s | 0.0279 | −1.28 |

Notes:
p-values were calculated using the Student's unpaired t-test for peak integrals with local baseline correction and incorporating spectral normalization using TSP. A positive fold change indicates up-regulation in HCC; while a negative fold change indicates up-regulation in HCV.

Figure 16:
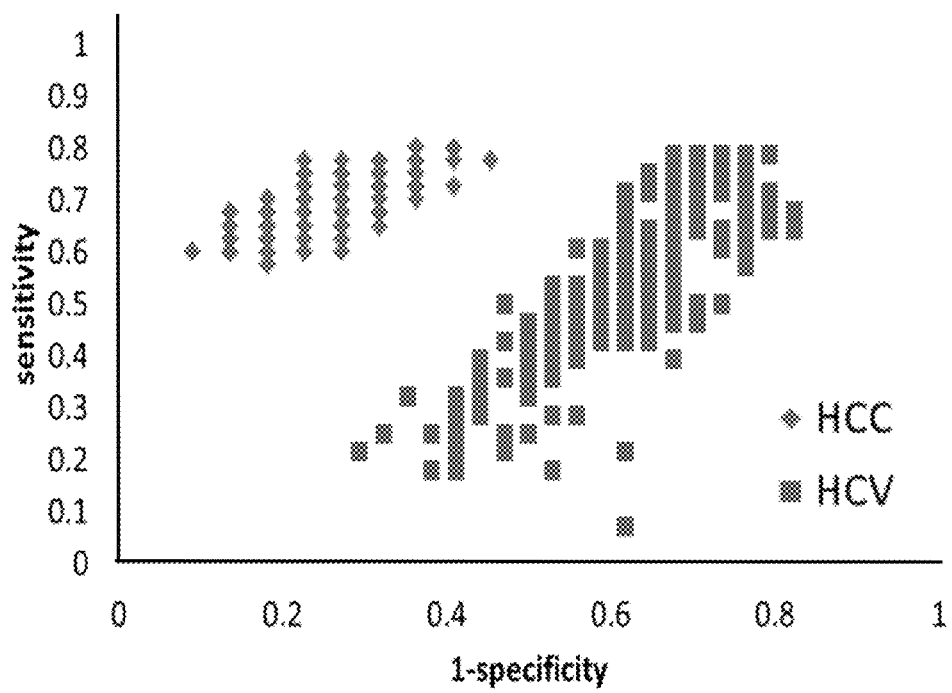
FIG. 16 shows the MCCV results (200 iterations) shown in ROC space for PLS-DA models based on the three metabolites used to discriminate HCC from HCV. Each diamond represents an iteration of the true model; each square represents an iteration of the permutation model.

To better evaluate the robustness of this model, the same MCVV and permutation were used again, and the results can be found in Table 15. This time, the average sensitivity and specificity are 71% and 73% for the true model, a significant increase over the results of the model based on nineteen metabolites. As expected, the permutation results show essentially a random distribution (sensitivity=54% and specificity=39%). To better visualize the difference, the results of the MCCV procedure are plotted in FIG. 16. FIG. 16 shows the MCCV results (200 iterations) shown in ROC space for PLS-DA models based on the three metabolites used to discriminate HCC from HCV. Each diamond represents an iteration of the true model; each square represents an iteration of the permutation model. The true model results cluster towards the top-left corner of the plot, representing good sensitivity and specificity. The permutation results are spread about the center of the plot and are well separated from the true model.

TABLE 15

Confusion matrix calculated from PLS-DA using three serum biomarkers for the HCC (n = 40) and HCV (n = 22) patients using 200 MCCV iterations. The numbers in parentheses are the results from permutation analysis.

| | | Predicted class | |
|---|---|---|---|
| True class | Total number of samples | HCC | HCV |
| HCC | 8000 (8000) | 5674 (4349) | 2326 (3651) |
| HCV | 4400 (4400) | 1195 (2735) | 3205 (1665) |

A metabolite profiling approach was applied to identify biomarker candidates for distinguishing HCC patients within an HCV population. The effectiveness of current HCC surveillance methods such as alpha-fetoprotein (AFP) and abdominal ultrasound (US) are limited by low sensitivity and specificity. The effectiveness of these surveillance methods in reducing HCC mortality remains modest. Improved detection methods, such as blood-based biomarkers are needed to improve this situation.

The metabolite biomarkers disclosed herein to enhance the detection of HCC. The entire $^1$H NMR spectrum can be used to develop a metabolite profile with good sensitivity and specificity. This approach is based on the combination of a large number of metabolite signals, many of which have not yet been identified. The use of feature selection, based on the Student's t-test resulted in three relatively strong biomarker candidates. The uncorrected p-values were used because each of these biomarker candidates has been shown to be involved in cancer metabolism and to avoid possible false negatives. In the case of creatinine, a gender difference in the two patient cohorts may be reducing its significance. The resulting PLS-DA model based on these three metabolites performs at least as well as the model based on the entire CPMG NMR spectrum. In contrast, the use of nineteen metabolites without the use of feature selection performs much more poorly. The OSC-PLS analysis of the full NOESY spectra showed a clear separation between HCC and HCV patients.

Figure 17:
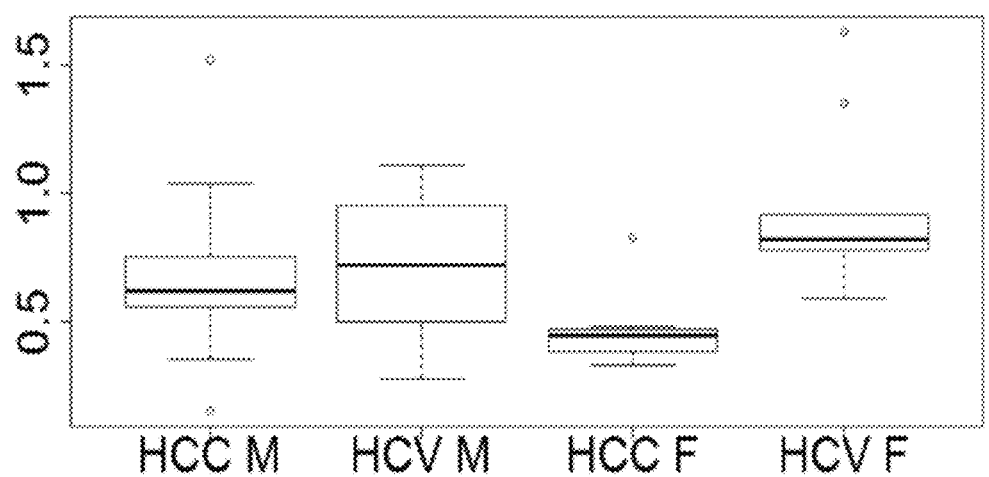
FIG. 17 shows box and whisker plots for creatinine in the HCC and HCV groups for both male (M) and female (F) patients.

An investigation of age and gender effects on the model was also performed to evaluate possible confounding effects. The averages and standard deviations of the age distributions in HCC and HCV groups are quite similar, indicating that there is no confounding effect to be anticipated due to age. However, the gender distribution differs significantly between the two groups. We therefore performed a Student's t-test for the three biomarkers between the male and female patients in each of the two patient cohorts. All p-values were above 0.05 (Table 16, below), indicating that any gender effect can be neglected for these metabolites in this study. The results also show that the disease effect on creatinine levels dominated any gender effect; creatinine increased overall, in males compared with females, and in females with HCV compared to those with HCC. Interestingly, the increase in creatinine levels for females was highly significant (Table 17, below). FIG. 17 shows box and whisker plots for creatinine in the HCC and HCV groups for both male (M) and female (F) patients.

TABLE 16 p-values of male vs female comparisons in the two different sample cohorts for the three metabolite biomarkers

| Metabolite | p-value in HCC (Male vs Female) | p-value in HCV (Male vs Female) |
|---|---|---|
| Choline | 0.53 | 0.41 |
| Valine | 0.55 | 0.06 |
| Creatinine | 0.06 | 0.12 |

TABLE 17 p-values for HCC vs HCV in both male and female patient populations for three metabolic biomarkers.

| Metabolite | p-value in male (HCC vs HCV) | p-value in female (HCC vs HCV) |
|---|---|---|
| Choline | 0.03 | 0.05 |
| Valine | 0.002 | 0.0007 |
| Creatinine | 0.5 | 0.003 |

Creatinine was found to decrease in the samples from HCC patients compared to those from patients with HCV without cancer, showing differences between the two diseased states. Other studies have focused on differences between diseased states (cirrhosis or cancer) compared to normal controls. Creatinine levels have been reported to be generally higher in males than in females and correlate with muscle mass. In this study, we found that the HCC patient group, which does have a significantly larger number of males compared to the HCV group, exhibits a lower concentration of creatinine, indicating a pathological role for creatinine, Among female patients alone the creatinine difference between HCV to HCC is quite significant, better gender-matched cohorts might well increase the significance of creatinine as a biomarker for HCC.

In this study, valine and choline were found to be up-regulated in HCC patients. In studies comparing HCC to normal controls, the elevation of valine has been observed in HCC tissue and blood, as well as the serum of HBV infected cirrhosis patients. An important step of valine catabolism occurs largely in the liver, involving oxidative decarboxylation of branched-chain α-keto acids generated from valine and other branched-chain amino acids in extrahepatic tissues. Previous studies showed that methacrylyl-coenzyme A (MC-CoA), a toxic compound generated in valine catabolism, is less detoxified in HCC or cirrhosis patients. MC-CoA induces a change of valine metabolism resulting in increased serum valine. Changes in valine levels have been found in some digestive system cancers, such as oral cancer and gastric cancer.

Changes in choline metabolism have also been related with HCC previously in studies comparing HCC patients and normal controls. The Lin group found decreased choline in HCC and cirrhosis patient sera compared with normal sera, although they did not compare HCC and cirrhotic patients. In HCC tissue, choline was found up-regulated, which is consistent with previous in vivo MRS studies. Generally, choline is an essential metabolite in the synthesis of phospholipids for cancer cell membranes. Choline is also is associated with many cancer types. For example, it has shown to be associated with colorectal cancer, high grade gliomas, and breast cancer. Thus, the metabolism of the membrane phospholipids caused by accelerated cell proliferation could be a reason for elevated choline in the sera of HCC patients.

$^1$H NMR metabolic profiling of serum samples has been shown to differentiate HCC from HCV patients in this study. In addition to a good separation based on broad lipid signals in the NMR spectra, three metabolites, creatinine, valine and choline, were found to differentiate the two disease groups, and each metabolite has some precedence as a potential HCC biomarker in human serum or urine. These metabolites are readily detected in serum by a number of analytical methods, indicating that upon further validation they could be translated into clinical practice.

Technical and scientific terms used herein have the same meaning as is commonly understood by one of skill in the art to which this disclosure belongs. It should be noted that the terms "first," "second," and the like herein do not denote any order or importance, but rather are used to distinguish one element from another. The terms "a" and "an" herein do not denote a limitation of quantity, but rather denote the presence of at least one of the referenced items. The terms "bottom" and "top" are used herein, unless otherwise noted, merely for convenience of description, and are not limited to anyone position or spatial orientation. In addition, the modifier "about" used in connection with a quantity is inclusive of the stated value and has the meaning dictated by the context (e.g., includes the degree of error associated with measurement of the particular quantity). Unless otherwise noted, the ends of a range are included in the range of values, e.g. "integers from 3 to 7" includes the values 3, 4, 5, 6, and 7.

While the disclosure has been described with reference to an exemplary embodiment, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims.

What is claimed is:

1. A method of determining evidence of hepatocellular carcinoma in a sample of biofluid, comprising the steps of:
measuring the concentration of a selected metabolite species in a sample of a biofluid from a subject, wherein each metabolite species is a component of an identified panel of three to sixteen metabolite species selected from the group consisting of 5-hydroxymethyl-2'-deoxyuridine, $N^2,N^2$-dimethylguanosine, methionine, uric acid, 1-methylinosine, 1-methylguanosine, 1-methyladenosine, xanthine, phenylalanine, 2-deoxyguanosine, tyrosine, N-carbamoyl-beta alanine, glycerol, aconitic acid, creatine, homocysteine, valine, cholyglycine, D-leucic acid, creatinine, 3-hydroxycapric acid and identifiable parts thereof,
wherein a change in the concentration of at least one metabolite species is characteristic of a transition from infection with hepatitis C virus to hepatocellular carcinoma thereby determining evidence of hepatocellular carcinoma.

2. The method of claim 1 further comprising the steps of:
comparing the measured concentrations of each metabolite species in the biofluid sample to the prediction of a statistical model.

3. The method of claim 1 wherein the panel is selected from the group consisting of:
a. the panel consisting of uric acid; cholylglycine, 3-hydroxycapric acid, D-leucic acid, and xanthine,
b. the panel consisting of choline, creatinine and valine
c. the panel consisting of 5-hydroxymethyl-2'-deoxyuridine, $N^2,N^2$-dimethylguanosine, methionine, uric acid;
d. the panel consisting of 5-hydroxymethyl-2'-deoxyuridine, $N^2,N^2$-dimethylguanosine, methionine, 1-nethylguanosine;
e. the panel consisting of 5-hydroxymethyl-2'-deoxyuridine, N $N^2,N^2$-dimethylguanosine, methionine, 1-methylinosine;
f. the panel consisting of 5-hydroxymethyl-2'-deoxyuridine, $N^2,N^2$-dimethylguanosine, methionine, xanthine;
g. the panel consisting of 5-hydroxymethyl-2'-deoxyuridine, $N^2,N^2$-dimethylguanosine, methionine, 1-methyladenosine;
h. the panel consisting of 5-hydroxymethyl-2'-deoxyuridine, $N^2,N^2$-dimethylguanosine, methionine, phenylalanine;
i. the panel consisting of $N^2,N^2$-dimethylguanosine, methionine, uric acid, 1-methylinosine;
j. the panel consisting of $N^2,N^2$-dimethylguanosine, methionine, uric acid, 1-methylguanosine;
k. the panel consisting of 5-hydroxymethyl-2'-deoxyuridine, $N^2,N^2$-dimethylguanosine, methionine, phenylalanine;
l. the panel consisting of 5-hydroxymethyl-2'-deoxyuridine, $N^2,N^2$-dimethylguanosine, methionine, 2-deoxyguanosine;
m. the panel consisting of 5-hydroxymethyl-2'-deoxyuridine, $N^2,N^2$-dimethylguanosine, methionine, tyrosine;
n. the panel consisting of 5-hydroxymethyl-2'-deoxyuridine, $N^2,N^2$-dimethylguanosine, methionine, n-carbamoyl-beta alanine;
o. the panel consisting of $N^2,N^2$-dimethylguanosine, methionine, uric acid, 1-methyladenosine;
P. the panel consisting of $N^2,N^2$-dimethylguanosine, methionine, uric acid, xanthine;
q. the panel consisting of 5-hydroxymethyl-2'-deoxyuridine, $N^2,N^2$-dimethylguanosine, methionine, glycerol;
r. the panel consisting of $N^2,N^2$-dimethylguanosine, methionine, uric acid, phenylalanine;
s. the panel consisting of $N^2,N^2$-dimethylguanosine, methionine, uric acid, 2-deoxyguanosine;
t. the panel consisting of $N^2,N^2$-dimethylguanosine, methionine, uric acid, tyrosine; and
u. the panel consisting of $N^2,N^2$-dimethylguanosine, methionine, uric acid, N-carbamoyl-beta alanine;
v. the panel consisting of $N^2,N^2$-dimethylguanosine, methionine, uric acid, glycerol;
w. the panel consisting of 5-hydroxymethyl-2'-deoxyuridine, 2-deoxyguanosine, N-carbamoyl-beta alanine, $N^2,N^2$-dimethylguanosine;
x. the panel consisting of methionine, uric acid, xanthine, phenylalanine;
y. the panel consisting of 5-hydroxymethyl-2'-deoxyuridine, $N^2,N^2$-dimethylguanosine, methionine, aconitic acid;
z. the panel consisting of 5-hydroxymethyl-2'-deoxyuridine, $N^2,N^2$-dimethylguanosine, methionine, creatine;
aa. the panel consisting of 5-hydroxymethyl-2'-deoxyuridine, 2-deoxyguanosine, N-carbamoyl-beta alanine, methionine;
bb. the panel consisting of methionine, uric acid, phenylalanine, 2-deoxyguanosine;
cc. the panel consisting of 5-hydroxymethyl-2'-deoxyuridine, 2-deoxyguanosine, N-carbamoyl-beta alanine, uric acid;
dd. the panel consisting of methionine, uric acid, phenylalanine, tyrosine;
ee. the panel consisting of $N^2,N^2$-dimethylguanosine, methionine, uric acid, aconitic acid;
ff. the panel consisting of $N^2,N^2$-dimethylguanosine, methionine, uric acid, creatine;
gg. the panel consisting of 5-hydroxymethyl-2'-deoxyuridine, $N^2,N^2$-dimethylguanosine, methionine, homocysteine;
hh. the panel consisting of 5-hydroxymethyl-2'-deoxyuridine, 2-deoxyguanosine, N-carbamoyl-beta alanine, 1-methyladenosine;
ii. the panel consisting of 5-hydroxymethyl-2'-deoxyuridine, 2-deoxyguanosine, N-carbamoyl-beta alanine, xanthine;
jj. the panel consisting of $N^2,N^2$-dimethylguanosine, methionine, uric acid, homocysteine;
kk. the panel consisting of 5-hydroxymethyl-2'-deoxyuridine, 2-deoxyguanosine, N-carbamoyl-beta alanine, tyrosine;
ll. the panel consisting of 5-hydroxymethyl-2'-deoxyuridine, 2-deoxyguanosine, N-carbamoyl-beta alanine, glycerol;
mm. the panel consisting of 5-hydroxymethyl-2'-deoxyuridine, 2-deoxyguanosine, N-carbamoyl-beta alanine, creatine;
nn. the panel consisting of methionine, uric acid, phenylalanine, homocysteine
oo. the panel consisting of 5-hydroxymethyl-2'-deoxyuridine, 2-deoxyguanosine, N-carbamoyl-beta alanine, aconitic acid;
pp. the panel consisting of 5-hydroxymethyl-2'-deoxyuridine, 2-deoxyguanosine, N-carbamoyl-beta alanine, homocysteine;
qq. the panel consisting of methionine, uric acid, xanthine, phenylalanine, tyrosine;
rr. the panel consisting of 5-hydroxymethyl-2'-deoxyuridine, $N^2,N^2$-dimethylguanosine, methionine, uric acid, 1-methylguanosine ss. the panel consisting of 5-hydroxymethyl-2'-deoxyuridine, $N^2,N^2$-dimethylguanosine, methionine, uric acid, 1-methylinosine;
tt. the panel consisting of 5-hydroxymethyl-2'-deoxyuridine, $N^2,N^2$-dimethylguanosine, methionine, uric acid, 1-methylinosine, 1-methylguanosine;
uu. the panel consisting of 5-hydroxymethyl-2'-deoxyuridine, $N^2,N^2$-dimethylguanosine, methionine, uric acid, 1-methylinosine, 1-methylguanosine, 1-methyladenosine;
vv. the panel consisting of 5-hydroxymethyl-2'-deoxyuridine, $N^2,N^2$-dimethylguanosine, methionine, uric acid, 1-methylinosine, 1-methylguanosine, 1-methyladenosine, xanthine;
ww. the panel consisting of 5-hydroxymethyl-2'-deoxyuridine, $N^2,N^2$-dimethylguanosine, methionine, uric acid, 1-methylinosine, 1-methylguanosine, 1-methyladenosine, xanthine, phenylalanine;
xx. the panel consisting of 5-hydroxymethyl-2'-deoxyuridine, $N^2,N^2$-dimethylguanosine, methionine, uric acid, 1-methylinosine, 1-methylguanosine, 1-methyladenosine, xanthine, phenylalanine, 2-deoxyguanosine;
yy. the panel consisting of methionine, uric acid, xanthine, phenylalanine, tyrosine, n-carbamoyl-beta alanine, glycerol, aconitic acid, creatine, homocysteine;
zz. the panel consisting of 5-hydroxymethyl-2'-deoxyuridine, $N^2,N^2$-dimethylguanosine, methionine, uric acid, 1-methylinosine, 1-methylguanosine, 1-methyladenosine, xanthine, phenylalanine, 2-deoxyguanosine, tyrosine;
aaa. the panel consisting of 5-hydroxymethyl-2'-deoxyuridine, $N^2,N^2$-dimethylguanosine, methionine, uric acid, 1-methylinosine, 1-methylguanosine, 1-methyladenosine, xanthine, phenylalanine, 2-deoxyguanosine, tyrosine, N-carbamoyl-beta alanine;
bbb. the panel consisting of 5-hydroxymethyl-2'-deoxyuridine, $N^2,N^2$-dimethylguanosine, methionine, uric acid, 1-methylinosine, 1-methylguanosine, 1-methyladenosine, xanthine, phenylalanine, 2-deoxyguanosine, tyrosine, N-carbamoyl-beta alanine, glycerol;
ccc. 5-hydroxymethyl-2'-deoxyuridine, $N^2,N^2$-dimethylguanosine, methionine, uric acid, 1-methylinosine, 1-methylguanosine, 1-methyladenosine, xanthine, phenylalanine, 2-deoxyguanosine, tyrosine, N-carbamoyl-beta alanine, glycerol, aconitic acid;
ddd. the panel consisting of methionine, uric acid, 1-methylinosine, 1-methylguanosine, 1-methyladenosine, xanthine, phenylalanine, 2-deoxyguanosine, tyrosine, N-carbamoyl-beta alanine, glycerol, aconitic acid, creatine, homocysteine;
eee. the panel consisting of 5-hydroxymethyl-2'-deoxyuridine, $N^2,N^2$-dimethylguanosine, methionine, uric acid, 1-methylinosine, 1-methylguanosine, 1-methyladenosine, xanthine, phenylalanine, 2-deoxyguanosine, tyrosine, N-carbamoyl-beta alanine, glycerol, aconitic acid, creatine;
fff. the panel consisting of 5-hydroxymethyl-2'-deoxyuridine, $N^2,N^2$-dimethylguanosine, methionine, uric acid, 1-methylinosine, 1-methylguanosine, 1-methyladenosine, xanthine, phenylalanine, 2-deoxyguanosine, tyrosine, N-carbamoyl-beta alanine, glycerol, aconitic acid, creatine, homocysteine;
ggg. the panel consisting of 5-hydroxymethyl-2'-deoxyuridine, $N^2,N^2$-dimethylguanosine, methionine, uric acid, 1-methylinosine, 1-methylguanosine, 1-methyladenosine, xanthine, phenylalanine, 2-deoxyguanosine, tyrosine, N-carbamoyl-beta alanine, glycerol, aconitic acid, creatine, homocysteine, valine, cholyglycine, d-leucic acid, creatinine, 3-hydroxycapric acid.

4. The method of claim 1 wherein the panel comprises metabolite species that have been identified by a plurality of methods selected from nuclear magnetic resonance (NMR) spectrometry, gas chromatography-mass spectrometry (GC-MS), liquid chromatography-mass spectrometry (LC-MS), correlation spectroscopy (COSy), nuclear Overhauser effect spectroscopy (NOESY), rotating frame nuclear Overhauser effect spectroscopy (ROESY), LC-TOF-MS, LC-MS/MS, and capillary electrophoresis-mass spectrometry.

5. The method of claim 1 wherein the panel comprises metabolite species that have been identified by nuclear magnetic resonance (NMR) spectrometry and liquid chromatography-mass spectrometry (LC-MS).

6. The method of claim 1 wherein the components of the panel are selected by the steps of identifying metabolite species that are present in the biofluid samples from hepatocellular carcinoma (HCC) subjects and the samples from subjects infected with hepatitis C virus (HCV); selecting the identified metabolite species the difference in concentration in the biofluid samples from the HCC subjects and the biofluid samples from the HCV subjects is significant at the level of $p<0.05$; and grouping the identified metabolite species to produce an identified panel of metabolite species wherein the average p-value of the metabolite species of a panel is in the range of 0.003 to 0.03.

7. The method of claim 1 wherein the sample comprises a biofluid selected from blood, plasma, serum, sweat, saliva, sputum or urine.

8. The method of claim 7, wherein the biofluid is serum.

9. The method of claim 1, wherein the panel is selected from the group consisting of: the panel of 5-hydroxymethyl-2'-deoxyuridine, $N^2,N^2$-dimethylguanosine, methionine, n-carbamoyl-beta alanine; and the panel of $N^2,N^2$-dimethylguanosine, methionine, uric acid, xanthine.

\* \* \* \* \*